US009365629B2

(12) United States Patent
Parmeggiani et al.

(10) Patent No.: US 9,365,629 B2
(45) Date of Patent: Jun. 14, 2016

(54) DESIGNED ARMADILLO REPEAT PROTEINS

(75) Inventors: Fabio Parmeggiani, Seattle, WA (US); Riccardo Pellarin, Zürich (CH); Anders Peter Larsen, Salt Lake City, UT (US); Gautham Varadamsetty, Zürich (CH); Michael Tobias Stumpp, Geroldswill (CH); Andreas Plückthun, Zürich (CH)

(73) Assignee: University of Zurich, Zurich (CH)

( * ) Notice: Subject to any disclaimer, the term of this patent is extended or adjusted under 35 U.S.C. 154(b) by 940 days.

(21) Appl. No.: 12/733,836

(22) PCT Filed: Sep. 23, 2008

(86) PCT No.: PCT/EP2008/062671

§ 371 (c)(1), (2), (4) Date: Mar. 23, 2010

(87) PCT Pub. No.: WO2009/040338

PCT Pub. Date: Apr. 2, 2009

(65) Prior Publication Data

US 2011/0224100 A1 Sep. 15, 2011

(30) Foreign Application Priority Data

Sep. 24, 2007 (EP) .................................... 07117059

(51) Int. Cl.

*C40B 40/10* (2006.01)
*C07K 14/47* (2006.01)
*C12N 15/10* (2006.01)

(52) U.S. Cl.

CPC ........ *C07K 14/4703* (2013.01); *C12N 15/1044* (2013.01)

(58) Field of Classification Search

None

See application file for complete search history.

(56) References Cited

U.S. PATENT DOCUMENTS

2004/0132028 A1 7/2004 Stumpp et al.
2006/0115813 A1* 6/2006 Yang et al. ........................ 435/6
2006/0117402 A1* 6/2006 Kim et al. ..................... 800/278

FOREIGN PATENT DOCUMENTS

WO 02/20565 3/2002

OTHER PUBLICATIONS

International Search Report issued Dec. 23, 2008 in International (PCT) Application No. PCT/EP2008/062671 along with the Written Opinion.

F. Parmeggiani et al., "Designed Armadillo Repeat Proteins as General Peptide-Binding Scaffolds: Consensus Design and Computational Optimization of the Hydrophobic Core", Journal of Molecular Biology, vol. 376, No. 5, pp. 1282-1304, Mar. 2008.

P. Forrer et al., "A Novel Strategy to Design Binding Molecules Harnessing the Modular Nature of Repeat Proteins", FEBS Letters, vol. 539, No. 1-3, pp. 2-6, Mar. 27, 2003.

P. Forrer et al., "Consensus Design of Repeat Proteins", ChemBioChem, A European Journal of Chemical Biology, vol. 5, No. 2, pp. 183-189, Feb. 6, 2004.

H. K. Binz et al., "High-Affinity Binders Selected from Designed Ankyrin Repeat Protein Libraries", Nature Biotechnology, vol. 22, No. 5, pp. 575-582, May 5, 2004.

J. C. Coates, "Armadillo Repeat Proteins: Beyond the Animal Kingdom", Trends in Cell Biology, vol. 13, No. 9, pp. 463-471, Sep. 9, 2003.

* cited by examiner

*Primary Examiner* — Christopher M Gross

(74) *Attorney, Agent, or Firm* — Finnegan, Henderson, Farabow, Garrett & Dunner

(57) ABSTRACT

The invention relates to collections of target-specific designed binding proteins based on armadillo repeat proteins, and to a method of generating them. Designed armadillo repeat proteins are based on consensus sequences of single armadillo repeat units. These repeat proteins can be used as scaffolds for peptide recognition. Such a scaffold provides a binding mode that is in principle the same for every small recognizable unit, e.g. an amino acid or dipeptide, allowing a precise and modular recognition of a peptide in extended conformation. The method allows to generate a series of modules recognizing these simple units, and to combine such building blocks to create a binding site for any desired peptide target without performing additional selections.

14 Claims, 10 Drawing Sheets

SEQUENCE LISTING

```
<160> NUMBER OF SEQ ID NOS: 121

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: consensus sequence

<400> SEQUENCE: 1

Asn Glu Gln Ile Gln Ala Val Ile Asp Ala Gly Ala Leu Pro Val Leu
1               5                   10                  15

Val Glu Leu Leu Ser Ser Pro Asp Asn Lys Ile Gln Lys Glu Ala Leu
            20                  25                  30

Trp Ala Leu Ser Asn Ile Thr Ser Gly Gly
        35                  40


<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: consensus sequence

<400> SEQUENCE: 2

Glu Ala Asn Lys Leu Ala Ile Arg Glu Ser Gly Gly Ile Pro Ala Leu
1               5                   10                  15

Val Arg Leu Leu Ser Ser Asn Asn Glu Lys Ile Leu Glu Ala Ala Thr
            20                  25                  30

Gly Thr Leu His Asn Leu Ala Leu His Gly
        35                  40


<210> SEQ ID NO 3
<211> LENGTH: 42
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: consensus sequence

<400> SEQUENCE: 3
```

```
Asn Glu Gln Ile Gln Ala Val Ile Asp Ala Gly Gly Leu Pro Ala Leu
1               5                   10                  15

Val Gln Leu Leu Ser Ser Pro Asn Glu Lys Ile Leu Lys Glu Ala Ala
            20                  25                  30

Trp Ala Leu Ser Asn Leu Ala Ser Gly Gly
        35                  40


<210> SEQ ID NO 4
<211> LENGTH: 42
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: consensus sequence

<400> SEQUENCE: 4

Asn Glu Gln Ile Gln Ala Val Ile Asp Ala Gly Ala Leu Pro Ala Leu
1               5                   10                  15

Val Gln Leu Leu Ser Ser Pro Asn Glu Lys Ile Leu Lys Glu Ala Leu
            20                  25                  30

Trp Ala Leu Ser Asn Ile Ala Ser Gly Gly
        35                  40


<210> SEQ ID NO 5
<211> LENGTH: 32
<212> TYPE: PRT
<213> ORGANISM: Saccharomyces cerevisiae

<400> SEQUENCE: 5

Glu Leu Pro Gln Met Thr Gln Gln Leu Asn Ser Asp Asp Met Gln Glu
1               5                   10                  15

Gln Leu Ser Ala Thr Val Lys Phe Arg Gln Ile Leu Ser Arg Asp Gly
            20                  25                  30


<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: derived capping repeat

<400> SEQUENCE: 6

Ser Leu Asn Glu Leu Val Lys Gln Leu Asn Ser Asp Asp Gln Lys Gln
1               5                   10                  15

Leu Lys Glu Ala Ala Gln Lys Leu Arg Gln Leu Ala Ser Asp Gly
            20                  25                  30


<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: derived capping repeat

<400> SEQUENCE: 7

Asn Glu Gln Lys Gln Ala Val Lys Glu Ala Gly Ala Leu Glu Lys Leu
```

```
1               5                   10                  15

Glu Gln Leu Gln Ser His Glu Asn Glu Lys Ile Gln Lys Glu Ala Gln
            20                  25                  30

Glu Ala Leu Glu Lys Gln Phe Ser His
        35                  40


<210> SEQ ID NO 8
<211> LENGTH: 43
<212> TYPE: PRT
<213> ORGANISM: Saccharomyces cerevisiae

<400> SEQUENCE: 8

Asp Asn Ile Asn Glu Asn Ala Asp Phe Ile Glu Lys Ala Gly Gly Met
1               5                   10                  15

Glu Lys Ile Phe Asn Cys Gln Gln Asn Glu Asn Asp Lys Ile Tyr Glu
            20                  25                  30

Lys Ala Tyr Lys Ile Ile Glu Thr Tyr Phe Gly
        35                  40


<210> SEQ ID NO 9
<211> LENGTH: 40
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: modified capping repeat

<400> SEQUENCE: 9

Asn Glu Asn Ala Asp Phe Ile Glu Lys Ala Gly Gly Met Glu Lys Ile
1               5                   10                  15

Phe Asn Ala Gln Gln Asn Glu Asn Asp Lys Ile Tyr Glu Lys Ala Tyr
            20                  25                  30

Lys Ile Ile Glu Thr Tyr Phe Gly
        35                  40


<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

cgggatccac acgtgcaatt cctg                                            24


<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

gcggtaccat tagtcctcag acattcgg                                        28


<210> SEQ ID NO 12
<211> LENGTH: 30
<212> TYPE: DNA
<213> ORGANISM: Artificial Sequence
<220> FEATURE:
```

<223> OTHER INFORMATION: Description of Artificial Sequence: Synthetic primer

<400> SEQUENCE: 12
cgggatccca tcacttctga catgattgag 30

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gcggtaccat tacccgaagt aatgctcaat aag 33

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
cggataacaa tttcacacag 20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gttctgaggt cattactg 18

<210> SEQ ID NO 16
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ccagggatcc gaactgccgc agatgaccca gcagctgaac tctg 44

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
cggtagcaga cagctgttcc tgcatgtcgt cagagttcag ctgctggg 48

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gaacagctgt ctgctaccgt taaattccgt cagatcctgt ctcgtgatgg 50

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
ttcctggtac cctaaggtct caaccatcac gagacaggat ctg 43

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ccagggatcc tctctgaacg aactggttaa acagctgaac tccg 44

<210> SEQ ID NO 21
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
ctgagcagct tctttcagct gtttctggtc gtcggagttc agctgtttaa ccag 54

<210> SEQ ID NO 22
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
cagctgaaag aagctgaaag aagctgctca gaaactgcgt cagctggctt ccgatgg 57

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
ttcctggtac cctaaggtct caaccatcgg aagccagctg 40

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ccagggatcc taggaagacc ttggtgacaa catcaacg 38

<210> SEQ ID NO 25
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gccaccagcc ttctcgatga agtccgcgtt ctcgttgatg ttgtcaccaa gg 52

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
cgagaaggct ggtggcatgg agaagatctt caactgccag cagaacg 47

<210> SEQ ID NO 27
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
gctttctcgt agatcttgtc gttctcgttc tgctggcagt tg 42

<210> SEQ ID NO 28
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
cgacaagatc tacgagaaag cttacaagat catcgaaacc tacttcggc 49

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
ttcctggtac ctcattagcc gaagtaggtt tcgatg 36

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ccagggatcc taggaagacc ttggtaacga gaacgcgg 38

<210> SEQ ID NO 31
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gccaccagcc ttctcgatga agtccgcgtt ctcgttacca agg 43

<210> SEQ ID NO 32
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
cgagaaggct ggtggcatgg agaagatctt caacgctcag cagaacg 47

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gctttctcgt agatcttgtc gttctcgttc tgctgagcgt tg 42

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
ccagggatcc taggaagacc ttggtaacga acagaaacag gc 42

<210> SEQ ID NO 35
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gtttctccag agcaccagct tctttaacag cctgtttctg ttcgttacc 49

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
gctggtgctc tggagaaact ggaacagctg cagtcccacg ag 42

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
cctgagcttc tttctggatc ttctcgttct cgtgggactg cagc 44

<210> SEQ ID NO 38
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gatccagaaa gaagctcagg aagctctgga gaagcagttc tccc 44

<210> SEQ ID NO 39
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
ttcctggtac ctcattagtg ggagaactgc ttctccag 38

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ccagggatcc taggaagacc ttggtaacga acagatcc 38

<210> SEQ ID NO 41
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
accggcagag caccagcgtc gataacagcc tggatctgtt cgttaccaag g 51

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 42

```
ctggtgctct gccggttctg gttgaactgc tgtcctctcc ggac                    44


<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

ccacagagct tctttctgga tcttgttgtc cggagaggac agcag                   45


<210> SEQ ID NO 44
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

tccagaaaga agctctgtgg gctctgtcta acatcacttc tggtggttga gacc         54


<210> SEQ ID NO 45
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

ttcctggtac cctaaggtct caaccaccag aagtg                              35


<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

ccagggatcc taggaagacc ttggtgaagc                                    30


<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

ccaccagatt cacggatagc cagtttgtta gcttcaccaa ggtcttcc                48


<210> SEQ ID NO 48
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

ctatccgtga atctggtggt atcccggctc tggttcgtct gctgtcctc               49
```

<210> SEQ ID NO 49
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
tagcagcttc caggatcttc tcgttgttag aggacagcag acgaacc 47

<210> SEQ ID NO 50
<211> LENGTH: 55
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
aagatcctgg aagctgctac tggcactctg cacaacctgg ctctgcatgg ttgag 55

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
ttcctggtac cctaaggtct caaccatgca gagcc 35

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
ccagggatcc taggaagacc ttggtaacga acaaatcc 38

<210> SEQ ID NO 53
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
agccggcaga ccaccagcat cgataacagc ttggatttgt tcgttaccaa gg 52

<210> SEQ ID NO 54
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
ggtggtctgc cggctctggt tcaactgctg tcctctccga acg 43

```
<210> SEQ ID NO 55
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55

ccaagcagct tctttcagga tcttctcgtt cggagaggac agc                     43


<210> SEQ ID NO 56
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56

cctgaaagaa gctgcttggg ctctgtctaa cctggcttct ggtggttgag              50


<210> SEQ ID NO 57
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

ttcctggtac cctaaggtct caaccaccag aagccag                            37


<210> SEQ ID NO 58
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

agccggcaga gcaccagcat cgataacagc ttggatttgt tcgttaccaa gg           52


<210> SEQ ID NO 59
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

agccggaaca gcaccagcat cgataacagc ttggatttgt tcgttaccaa gg           52


<210> SEQ ID NO 60
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

agccgggata gcaccagcat cgataacagc ttggatttgt tcgttaccaa gg           52
```

<210> SEQ ID NO 61
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
ggtgctctgc cggctctggt tcaactgctg tcctctccga acg 43

<210> SEQ ID NO 62
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
ggtgctgttc cggctctggt tcaactgctg tcctctccga acg 43

<210> SEQ ID NO 63
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
ggtgctatcc cggctctggt tcaactgctg tcctctccga acg 43

<210> SEQ ID NO 64
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
ccacagagct tctttcagca gcttctcgtt cggagaggac agc 43

<210> SEQ ID NO 65
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
ccaaacagct tctttcagca gcttctcgtt cggagaggac agc 43

<210> SEQ ID NO 66
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ccacagagct tctttcagaa ccttctcgtt cggagaggac agc 43

<210> SEQ ID NO 67

<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
ccaagcagct tctttcagca gcttctcgtt cggagaggac agc 43

<210> SEQ ID NO 68
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
ccacagagct tctttcagga tcttctcgtt cggagaggac agc 43

<210> SEQ ID NO 69
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
ctgaaagaag ctctgtgggc tctgtctaac ctggcttctg gtggttgag 49

<210> SEQ ID NO 70
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
ctgaaagaag ctgtttgggc tctgtctaac ctggcttctg gtggttgag 49

<210> SEQ ID NO 71
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
ctgaaagaag ctgcttgggt tctgtctaac ctggcttctg gtggttgag 49

<210> SEQ ID NO 72
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
ctgaaagaag ctctgtgggt tctgtctaac ctggcttctg gtggttgag 49

<210> SEQ ID NO 73
<211> LENGTH: 49

<212> TYPE: DNA
<213> ORGANISM: Artificial Sequence
<220> FEATURE:
<223> OTHER INFORMATION: Description of Artificial Sequence: Synthetic primer

<400> SEQUENCE: 73
ctgaaagaag ctgtttgggt tctgtctaac ctggcttctg gtggttgag 49

<210> SEQ ID NO 74
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ctgaaagaag ctgcttgggc tctgtctaac atcgcttctg gtggttgag 49

<210> SEQ ID NO 75
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
ctgaaagaag ctctgtgggc tctgtctaac atcgcttctg gtggttgag 49

<210> SEQ ID NO 76
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 76
ctgaaagaag ctctgtgggt tctgtctaac atcgcttctg gtggttgag 49

<210> SEQ ID NO 77
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 77
ttcctggtac cctaaggtct caaccaccag aagcgat 37

<210> SEQ ID NO 78
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
ttcctggtac cctaaggtct cattcgttac catcacgaga caggatctg 49

<210> SEQ ID NO 79
<211> LENGTH: 42
<212> TYPE: DNA

<213> ORGANISM: Artificial Sequence
<220> FEATURE:
<223> OTHER INFORMATION: Description of Artificial Sequence: Synthetic
primer

<400> SEQUENCE: 79
ccagggatcc tctagatagg aagacctcga acagaaacag gc 42

<210> SEQ ID NO 80
<211> LENGTH: 49
<212> TYPE: DNA
<213> ORGANISM: Artificial Sequence
<220> FEATURE:
<223> OTHER INFORMATION: Description of Artificial Sequence: Synthetic
primer

<400> SEQUENCE: 80
gtttctccag agcaccagct tctttaacag cctgtttctg ttcgaggtc 49

<210> SEQ ID NO 81
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 81
ccagggatcc taggaagacc tcgaacaaay ccaagctgtt atcg 44

<210> SEQ ID NO 82
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 82
ccagggatcc taggaagacc tcgaacaava acaagctgtt atcg 44

<210> SEQ ID NO 83
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 83
ccagggatcc taggaagacc tcgaacaacr ccaagctgtt atcg 44

<210> SEQ ID NO 84
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 84
ccagagccgg cagagcacca gcatcgataa cagcttg 37

<210> SEQ ID NO 85
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
ctgccggctc tggttcaact gctgtcctct c 31

<210> SEQ ID NO 86
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
tttcaggatc ttctcgttcg gagaggacag cag 33

<210> SEQ ID NO 87
<211> LENGTH: 65
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: MOD_RES
<222> LOCATION: (17)..(19)
<223> OTHER INFORMATION: n is a, c, g, or t
<220> FEATURE:
<221> NAME/KEY: MOD_RES
<222> LOCATION: (26)..(28)
<223> OTHER INFORMATION: n is a, c, g, or t
<220> FEATURE:
<221> NAME/KEY: MOD_RES
<222> LOCATION: (35)..(37)
<223> OTHER INFORMATION: n is a, c, g, or t
<220> FEATURE:
<221> NAME/KEY: MOD_RES
<222> LOCATION: (47)..(52)
<223> OTHER INFORMATION: n is a, c, g, or t

<400> SEQUENCE: 87
cgagaagatc ctgaaannng ctctgnnngc tctgnnnaac atcgctnnnn nnggtaacga 60
atgag 65

<210> SEQ ID NO 88
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
ttcctggtac cctaaggtct cattcgttac c 31

<210> SEQ ID NO 89
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
ccagggatcc taggaagacc tcgaac 26

<210> SEQ ID NO 90
<211> LENGTH: 173
<212> TYPE: DNA
<213> ORGANISM: Artificial Sequence
<220> FEATURE:
<223> OTHER INFORMATION: Description of Artificial Sequence: Synthetic construct
<220> FEATURE:
<223> OTHER INFORMATION: Type C module DNA

<400> SEQUENCE: 90
ccagggatcc taggaagacc ttggtaacga acaaatccaa gctgttatcg atgctggtgg 60
tctgccggct ctggttcaac tgctgtcctc tccgaacgag aagatcctga aagaagctgc 120
ttgggctctg tctaacctgg cttctggtgg ttgagacctt agggtaccag gaa 173

<210> SEQ ID NO 91
<211> LENGTH: 128
<212> TYPE: DNA
<213> ORGANISM: Artificial Sequence
<220> FEATURE:
<223> OTHER INFORMATION: Description of Artificial Sequence: Synthetic construct
<220> FEATURE:
<223> OTHER INFORMATION: Ny capping module DNA

<400> SEQUENCE: 91
ccagggatcc gaactgccgc agatgaccca gcagctgaac tctgacgaca tgcaggaaca 60
gctgtctgct accgttaaat tccgtcagat cctgtctcgt gatggttgag accttagggt 120
accaggaa 128

<210> SEQ ID NO 92
<211> LENGTH: 165
<212> TYPE: DNA
<213> ORGANISM: Artificial Sequence
<220> FEATURE:
<223> OTHER INFORMATION: Description of Artificial Sequence: Synthetic construct
<220> FEATURE:
<223> OTHER INFORMATION: Ca capping module DNA

<400> SEQUENCE: 92
ccagggatcc taggaagacc ttggtaacga acagaaacag gctgttaaag aagctggtgc 60
tctggagaaa ctggaacagc tgcagtccca cgagaacgag aagatccaga aagaagctca 120
ggaagctctg gagaagcagt tctcccacta atgaggtacc aggaa 165

<210> SEQ ID NO 93
<211> LENGTH: 169
<212> TYPE: PRT
<213> ORGANISM: Artificial Sequence
<220> FEATURE:
<223> OTHER INFORMATION: Description of Artificial Sequence: Synthetic construct
<220> FEATURE:
<223> OTHER INFORMATION: Repeat protein YC2A

<400> SEQUENCE: 93

```
Met Arg Gly Ser His His His His His His Gly Ser Glu Leu Pro Gln
1               5                   10                  15

Met Thr Gln Gln Leu Asn Ser Asp Asp Met Gln Glu Gln Leu Ser Ala
            20                  25                  30

Thr Val Lys Phe Arg Gln Ile Leu Ser Arg Asp Gly Asn Glu Gln Ile
        35                  40                  45

Gln Ala Val Ile Asp Ala Gly Gly Leu Pro Ala Leu Val Gln Leu Leu
```

-continued

```
    50                  55                  60

Ser Ser Pro Asn Glu Lys Ile Leu Lys Glu Ala Ala Trp Ala Leu Ser
65                  70                  75                  80

Asn Leu Ala Ser Gly Gly Asn Glu Gln Ile Gln Ala Val Ile Asp Ala
                85                  90                  95

Gly Gly Leu Pro Ala Leu Val Gln Leu Leu Ser Ser Pro Asn Glu Lys
            100                 105                 110

Ile Leu Lys Glu Ala Ala Trp Ala Leu Ser Asn Leu Ala Ser Gly Gly
        115                 120                 125

Asn Glu Gln Lys Gln Ala Val Lys Glu Ala Gly Ala Leu Glu Lys Leu
    130                 135                 140

Glu Gln Leu Gln Ser His Glu Asn Glu Lys Ile Gln Lys Glu Ala Gln
145                 150                 155                 160

Glu Ala Leu Glu Lys Gln Phe Ser His
                165
```

<210> SEQ ID NO 94
<211> LENGTH: 522
<212> TYPE: DNA
<213> ORGANISM: Artificial Sequence
<220> FEATURE:
<223> OTHER INFORMATION: Description of Artificial Sequence: Synthetic construct
<220> FEATURE:
<223> OTHER INFORMATION: DNA coding for repeat protein YC2A

<400> SEQUENCE: 94

```
atgagaggat cgcatcacca tcaccatcac ggatccgaac tgccgcagat gacccagcag     60

ctgaactccg acgacatgca ggaacagctg tctgctaccg ttaaattccg tcagatcctg    120

tctcgtgatg gtaacgaaca aatccaagct gttatcgatg ctggtggtct gccggctctg    180

gttcaactgc tgtcctctcc gaacgagaag atcctgaaag aagctgcttg ggctctgtct    240

aacctggctt ctggtggtaa cgaacaaatc caagctgtta tcgatgctgg tggtctgccg    300

gctctggttc aactgctgtc ctctccgaac gagaagatcc tgaaagaagc tgcttgggct    360

ctgtctaacc tggcttctgg tggtaacgaa cagaaacagg ctgttaaaga agctggtgct    420

ctggagaaac tggaacagct gcagtcccac gagaacgaga agatccagaa agaagctcag    480

gaagctctgg agaagcagtt ctcccactaa tgaggtaccc cg                       522
```

<210> SEQ ID NO 95
<211> LENGTH: 134
<212> TYPE: DNA
<213> ORGANISM: Artificial Sequence
<220> FEATURE:
<223> OTHER INFORMATION: Description of Artificial Sequence: Synthetic construct
<220> FEATURE:
<223> OTHER INFORMATION: NyLib capping module DNA

<400> SEQUENCE: 95

```
ccagggatcc gaactgccgc agatgaccca gcagctgaac tctgacgaca tgcaggaaca     60

gctgtctgct accgttaaat tccgtcagat cctgtctcgt gatggtaacg aatgagacct    120

tagggtacca ggaa                                                       134
```

<210> SEQ ID NO 96
<211> LENGTH: 173
<212> TYPE: DNA
<213> ORGANISM: Artificial Sequence
<220> FEATURE:

```
<223> OTHER INFORMATION: Description of Artificial Sequence: Synthetic
      construct
<220> FEATURE:
<223> OTHER INFORMATION: Library module DNA
<220> FEATURE:
<221> NAME/KEY: MOD_RES
<222> LOCATION: (29)..(31)
<223> OTHER INFORMATION: n is a, c, g, or t
<220> FEATURE:
<221> NAME/KEY: MOD_RES
<222> LOCATION: (107)..(109)
<223> OTHER INFORMATION: n is a, c, g, or t
<220> FEATURE:
<221> NAME/KEY: MOD_RES
<222> LOCATION: (116)..(118)
<223> OTHER INFORMATION: n is a, c, g, or t
<220> FEATURE:
<221> NAME/KEY: MOD_RES
<222> LOCATION: (125)..(127)
<223> OTHER INFORMATION: n is a, c, g, or t
<220> FEATURE:
<221> NAME/KEY: MOD_RES
<222> LOCATION: (137)..(142)
<223> OTHER INFORMATION: n is a, c, g, or t

<400> SEQUENCE: 96

ccagggatcc taggaagacc tcgaacaann ncaagctgtt atcgatgctg gtgctctgcc     60

ggctctggtt caactgctgt cctctccgaa cgagaagatc ctgaaannng ctctgnnngc    120

tctgnnnaac atcgctnnnn nnggtaacga atgagacctt agggtaccag gaa           173


<210> SEQ ID NO 97
<211> LENGTH: 165
<212> TYPE: DNA
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: CaLib capping module DNA

<400> SEQUENCE: 97

ccagggatcc tctagatagg aagacctcga acagaaacag gctgttaaag aagctggtgc     60

tctggagaaa ctggaacagc tgcagtccca cgagaacgag aagatccaga aagaagctca    120

ggaagctctg gagaagcagt tctcccacta atgaggtacc aggaa                    165


<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: NLS peptide

<400> SEQUENCE: 98

Lys Lys Lys Arg Lys Val
1               5


<210> SEQ ID NO 99
<211> LENGTH: 32
<212> TYPE: DNA
<213> ORGANISM: Artificial Sequence
<220> FEATURE:
<223> OTHER INFORMATION: Description of Artificial Sequence: Synthetic
      construct
<220> FEATURE:
<223> OTHER INFORMATION: flag tag of plasmid pRDV
```

<400> SEQUENCE: 99
ccatggcgga ctacaaagat gacgatgaca aa 32

<210> SEQ ID NO 100
<211> LENGTH: 32
<212> TYPE: DNA
<213> ORGANISM: Artificial Sequence
<220> FEATURE:
<223> OTHER INFORMATION: Description of Artificial Sequence: Synthetic construct
<220> FEATURE:
<223> OTHER INFORMATION: MRGS tag of plasmid pRDVhisCAG

<400> SEQUENCE: 100
tcatgcgagg gtcgcatcac catcaccatc ac 32

<210> SEQ ID NO 101
<211> LENGTH: 6
<212> TYPE: PRT
<213> ORGANISM: Artificial Sequence
<220> FEATURE:
<223> OTHER INFORMATION: Description of Artificial Sequence: Synthetic construct
<220> FEATURE:
<223> OTHER INFORMATION: cro peptide

<400> SEQUENCE: 101

Pro Arg Thr Ser Ser Phe
1 5

<210> SEQ ID NO 102
<211> LENGTH: 70
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Xaa is Arg, Asn, Asp, Cys, Glu, Gln, His, Lys, Ser, Thr or Tyr
<220> FEATURE:
<221> NAME/KEY: MOD_RES
<222> LOCATION: (2)..(2)
<223> OTHER INFORMATION: Xaa is any naturally occurring amino acid
<220> FEATURE:
<221> NAME/KEY: MOD_RES
<222> LOCATION: (3)..(3)
<223> OTHER INFORMATION: Xaa is Arg, Asn, Asp, Cys, Glu, Gln, His, Lys, Ser, Thr or Tyr
<220> FEATURE:
<221> NAME/KEY: MOD_RES
<222> LOCATION: (4)..(5)
<223> OTHER INFORMATION: Xaa is any naturally occurring amino acid
<220> FEATURE:
<221> NAME/KEY: MOD_RES
<222> LOCATION: (6)..(7)
<223> OTHER INFORMATION: Xaa is Ala, Gly, Ile, Leu, Met, Phe, Pro, Trp or Val
<220> FEATURE:
<221> NAME/KEY: MOD_RES
<222> LOCATION: (8)..(10)
<223> OTHER INFORMATION: Xaa is any naturally occurring amino acid
<220> FEATURE:
<221> NAME/KEY: MOD_RES
<222> LOCATION: (11)..(11)
<223> OTHER INFORMATION: Xaa is any naturally occurring amino acid or is absent
<220> FEATURE:
<221> NAME/KEY: MOD_RES
<222> LOCATION: (13)..(13)
<223> OTHER INFORMATION: Xaa is any naturally occurring amino acid or is absent
<220> FEATURE:
<221> NAME/KEY: MOD_RES
<222> LOCATION: (14)..(15)
<223> OTHER INFORMATION: Xaa is Ala, Gly, Ile, Leu, Met, Phe, Pro, Trp
or Val
<220> FEATURE:
<221> NAME/KEY: MOD_RES
<222> LOCATION: (17)..(17)
<223> OTHER INFORMATION: Xaa is any naturally occurring amino acid
<220> FEATURE:
<221> NAME/KEY: MOD_RES
<222> LOCATION: (19)..(19)
<223> OTHER INFORMATION: Xaa is Ala, Gly, Ile, Leu, Met, Phe, Pro, Trp
or Val
<220> FEATURE:
<221> NAME/KEY: MOD_RES
<222> LOCATION: (20)..(20)
<223> OTHER INFORMATION: Xaa is Arg, Asn, Asp, Cys, Glu, Gln, His, Lys,
Ser, Thr or Tyr
<220> FEATURE:
<221> NAME/KEY: MOD_RES
<222> LOCATION: (23)..(23)
<223> OTHER INFORMATION: Xaa is any naturally occurring amino acid
<220> FEATURE:
<221> NAME/KEY: MOD_RES
<222> LOCATION: (24)..(26)
<223> OTHER INFORMATION: Xaa is any naturally occurring amino acid or is
absent
<220> FEATURE:
<221> NAME/KEY: MOD_RES
<222> LOCATION: (27)..(27)
<223> OTHER INFORMATION: Xaa is Arg, Asn, Asp, Cys, Glu, Gln, His, Lys,
Ser, Thr or Tyr
<220> FEATURE:
<221> NAME/KEY: MOD_RES
<222> LOCATION: (28)..(29)
<223> OTHER INFORMATION: Xaa is any naturally occurring amino acid
<220> FEATURE:
<221> NAME/KEY: MOD_RES
<222> LOCATION: (30)..(32)
<223> OTHER INFORMATION: Xaa is any naturally occurring amino acid or is
absent
<220> FEATURE:
<221> NAME/KEY: MOD_RES
<222> LOCATION: (33)..(34)
<223> OTHER INFORMATION: Xaa is any naturally occurring amino acid
<220> FEATURE:
<221> NAME/KEY: MOD_RES
<222> LOCATION: (35)..(35)
<223> OTHER INFORMATION: Xaa is Ala, Gly, Ile, Leu, Met, Phe, Pro, Trp
or Val
<220> FEATURE:
<221> NAME/KEY: MOD_RES
<222> LOCATION: (36)..(38)
<223> OTHER INFORMATION: Xaa is any naturally occurring amino acid
<220> FEATURE:
<221> NAME/KEY: MOD_RES
<222> LOCATION: (40)..(40)
<223> OTHER INFORMATION: Xaa is Ala, Gly, Ile, Leu, Met, Phe, Pro, Trp
or Val
<220> FEATURE:
<221> NAME/KEY: MOD_RES
<222> LOCATION: (41)..(42)
<223> OTHER INFORMATION: Xaa is any naturally occurring amino acid
<220> FEATURE:
<221> NAME/KEY: MOD_RES
<222> LOCATION: (44)..(44)
<223> OTHER INFORMATION: Xaa is any naturally occurring amino acid
<220> FEATURE:
<221> NAME/KEY: MOD_RES
<222> LOCATION: (46)..(46)
<223> OTHER INFORMATION: Xaa is Ala, Gly, Ile, Leu, Met, Phe, Pro, Trp
or Val
<220> FEATURE:
<221> NAME/KEY: MOD_RES
<222> LOCATION: (47)..(48)
<223> OTHER INFORMATION: Xaa is any naturally occurring amino acid
<220> FEATURE:

```
<221> NAME/KEY: MOD_RES
<222> LOCATION: (49)..(68)
<223> OTHER INFORMATION: Xaa is any naturally occurring amino acid or is
      absent
<220> FEATURE:
<221> NAME/KEY: MOD_RES
<222> LOCATION: (69)..(70)
<223> OTHER INFORMATION: Xaa is any naturally occurring amino acid

<400> SEQUENCE: 102

Xaa Xaa Xaa Xaa Xaa Xaa Xaa Xaa Xaa Xaa Xaa Gly Xaa Xaa Xaa Pro
1               5                   10                  15

Xaa Leu Xaa Xaa Leu Leu Xaa Xaa Xaa Xaa Xaa Xaa Xaa Xaa Xaa Xaa
            20                  25                  30

Xaa Xaa Xaa Xaa Xaa Xaa Ala Xaa Xaa Xaa Leu Xaa Asn Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa
65                  70


<210> SEQ ID NO 103
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Xaa is any naturally occurring amino acid
<220> FEATURE:
<221> NAME/KEY: MOD_RES
<222> LOCATION: (4)..(4)
<223> OTHER INFORMATION: Xaa is any naturally occurring amino acid
<220> FEATURE:
<221> NAME/KEY: MOD_RES
<222> LOCATION: (6)..(6)
<223> OTHER INFORMATION: Xaa is Ala, Phe, Gly, Ile, Leu, Met, Pro, Thr,
      Val, Trp or Tyr
<220> FEATURE:
<221> NAME/KEY: MOD_RES
<222> LOCATION: (9)..(9)
<223> OTHER INFORMATION: Xaa is Ala, Cys, Asp, Glu, Gly, His, Lys, Asn,
      Pro, Gln, Arg, Ser, Thr or Tyr
<220> FEATURE:
<221> NAME/KEY: MOD_RES
<222> LOCATION: (10)..(10)
<223> OTHER INFORMATION: Xaa is any naturally occurring amino acid
<220> FEATURE:
<221> NAME/KEY: MOD_RES
<222> LOCATION: (12)..(13)
<223> OTHER INFORMATION: Xaa is Ala, Phe, Gly, Ile, Leu, Met, Pro, Thr,
      Val, Trp or Tyr
<220> FEATURE:
<221> NAME/KEY: MOD_RES
<222> LOCATION: (15)..(15)
<223> OTHER INFORMATION: Xaa is any naturally occurring amino acid
<220> FEATURE:
<221> NAME/KEY: MOD_RES
<222> LOCATION: (17)..(17)
<223> OTHER INFORMATION: Xaa is Ala, Phe, Gly, Ile, Leu, Met, Pro, Thr,
      Val, Trp or Tyr
<220> FEATURE:
<221> NAME/KEY: MOD_RES
<222> LOCATION: (18)..(18)
<223> OTHER INFORMATION: Xaa is Ala, Cys, Asp, Glu, Gly, His, Lys, Asn,
      Pro, Gln, Arg, Ser, Thr or Tyr
<220> FEATURE:
<221> NAME/KEY: MOD_RES
<222> LOCATION: (21)..(21)
<223> OTHER INFORMATION: Xaa is any naturally occurring amino acid
```

```
<220> FEATURE:
<221> NAME/KEY: MOD_RES
<222> LOCATION: (22)..(22)
<223> OTHER INFORMATION: Xaa is Ala, Cys, Asp, Glu, Gly, His, Lys, Asn,
      Pro, Gln, Arg,      Ser, Thr or Tyr
<220> FEATURE:
<221> NAME/KEY: MOD_RES
<222> LOCATION: (23)..(23)
<223> OTHER INFORMATION: Xaa is any naturally occurring amino acid
<220> FEATURE:
<221> NAME/KEY: MOD_RES
<222> LOCATION: (25)..(26)
<223> OTHER INFORMATION: Xaa is any naturally occurring amino acid
<220> FEATURE:
<221> NAME/KEY: MOD_RES
<222> LOCATION: (27)..(27)
<223> OTHER INFORMATION: Xaa is Ala, Phe, Gly, Ile, Leu, Met, Pro, Thr,
      Val, Trp or Tyr
<220> FEATURE:
<221> NAME/KEY: MOD_RES
<222> LOCATION: (28)..(30)
<223> OTHER INFORMATION: Xaa is any naturally occurring amino acid
<220> FEATURE:
<221> NAME/KEY: MOD_RES
<222> LOCATION: (32)..(32)
<223> OTHER INFORMATION: Xaa is Ala, Phe, Gly, Ile, Leu, Met, Pro, Thr,
      Val, Trp or Tyr
<220> FEATURE:
<221> NAME/KEY: MOD_RES
<222> LOCATION: (33)..(33)
<223> OTHER INFORMATION: Xaa is any naturally occurring amino acid
<220> FEATURE:
<221> NAME/KEY: MOD_RES
<222> LOCATION: (36)..(36)
<223> OTHER INFORMATION: Xaa is any naturally occurring amino acid
<220> FEATURE:
<221> NAME/KEY: MOD_RES
<222> LOCATION: (39)..(42)
<223> OTHER INFORMATION: Xaa is any naturally occurring amino acid

<400> SEQUENCE: 103

Asn Xaa Gln Xaa Gln Xaa Val Ile Xaa Xaa Gly Xaa Xaa Pro Xaa Leu
1               5                   10                  15

Xaa Xaa Leu Leu Xaa Xaa Xaa Asp Xaa Xaa Xaa Xaa Xaa Xaa Ala Xaa
            20                  25                  30

Xaa Ala Leu Xaa Asn Ile Xaa Xaa Xaa Xaa
        35                  40


<210> SEQ ID NO 104
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Xaa is any naturally occurring amino acid
<220> FEATURE:
<221> NAME/KEY: MOD_RES
<222> LOCATION: (26)..(26)
<223> OTHER INFORMATION: Xaa is any naturally occurring amino acid
<220> FEATURE:
<221> NAME/KEY: MOD_RES
<222> LOCATION: (29)..(30)
<223> OTHER INFORMATION: Xaa is any naturally occurring amino acid
<220> FEATURE:
<221> NAME/KEY: MOD_RES
<222> LOCATION: (33)..(33)
<223> OTHER INFORMATION: Xaa is any naturally occurring amino acid
<220> FEATURE:
<221> NAME/KEY: MOD_RES
<222> LOCATION: (36)..(36)
<223> OTHER INFORMATION: Xaa is any naturally occurring amino acid
```

<220> FEATURE:
<221> NAME/KEY: MOD_RES
<222> LOCATION: (40)..(41)
<223> OTHER INFORMATION: Xaa is any naturally occurring amino acid

<400> SEQUENCE: 104

```
Asn Glu Gln Xaa Gln Ala Val Ile Asp Ala Gly Ala Leu Pro Val Leu
1               5                   10                  15

Val Glu Leu Leu Ser Ser Pro Asp Asn Xaa Ile Gln Xaa Xaa Ala Leu
            20                  25                  30

Xaa Ala Leu Xaa Asn Ile Thr Xaa Xaa Gly
        35                  40
```

<210> SEQ ID NO 105
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (2)..(2)
<223> OTHER INFORMATION: Xaa is any naturally occurring amino acid
<220> FEATURE:
<221> NAME/KEY: MOD_RES
<222> LOCATION: (4)..(4)
<223> OTHER INFORMATION: Xaa is any naturally occurring amino acid
<220> FEATURE:
<221> NAME/KEY: MOD_RES
<222> LOCATION: (5)..(5)
<223> OTHER INFORMATION: Xaa is Ala, Phe, Gly, Ile, Leu, Met, Pro, Thr, Val, Trp or Tyr
<220> FEATURE:
<221> NAME/KEY: MOD_RES
<222> LOCATION: (8)..(10)
<223> OTHER INFORMATION: Xaa is any naturally occurring amino acid
<220> FEATURE:
<221> NAME/KEY: MOD_RES
<222> LOCATION: (13)..(13)
<223> OTHER INFORMATION: Xaa is Ala, Phe, Gly, Ile, Leu, Met, Pro, Thr, Val, Trp or Tyr
<220> FEATURE:
<221> NAME/KEY: MOD_RES
<222> LOCATION: (15)..(15)
<223> OTHER INFORMATION: Xaa is any naturally occurring amino acid
<220> FEATURE:
<221> NAME/KEY: MOD_RES
<222> LOCATION: (18)..(18)
<223> OTHER INFORMATION: Xaa is Ala, Cys, Asp, Glu, Gly, His, Lys, Asn, Pro, Gln, Arg, Ser, Thr or Tyr
<220> FEATURE:
<221> NAME/KEY: MOD_RES
<222> LOCATION: (21)..(21)
<223> OTHER INFORMATION: Xaa is any naturally occurring amino acid
<220> FEATURE:
<221> NAME/KEY: MOD_RES
<222> LOCATION: (22)..(22)
<223> OTHER INFORMATION: Xaa is Ala, Cys, Asp, Glu, Gly, His, Lys, Asn, Pro, Gln, Arg, Ser, Thr or Tyr
<220> FEATURE:
<221> NAME/KEY: MOD_RES
<222> LOCATION: (23)..(26)
<223> OTHER INFORMATION: Xaa is any naturally occurring amino acid
<220> FEATURE:
<221> NAME/KEY: MOD_RES
<222> LOCATION: (27)..(28)
<223> OTHER INFORMATION: Xaa is Ala, Phe, Gly, Ile, Leu, Met, Pro, Thr, Val, Trp or Tyr
<220> FEATURE:
<221> NAME/KEY: MOD_RES
<222> LOCATION: (29)..(30)
<223> OTHER INFORMATION: Xaa is any naturally occurring amino acid
<220> FEATURE:
<221> NAME/KEY: MOD_RES
<222> LOCATION: (32)..(32)
<223> OTHER INFORMATION: Xaa is Ala, Phe, Gly, Ile, Leu, Met, Pro, Thr, Val, Trp or Tyr
<220> FEATURE:
<221> NAME/KEY: MOD_RES
<222> LOCATION: (33)..(34)
<223> OTHER INFORMATION: Xaa is any naturally occurring amino acid
<220> FEATURE:
<221> NAME/KEY: MOD_RES
<222> LOCATION: (36)..(36)
<223> OTHER INFORMATION: Xaa is any naturally occurring amino acid
<220> FEATURE:
<221> NAME/KEY: MOD_RES
<222> LOCATION: (39)..(42)
<223> OTHER INFORMATION: Xaa is any naturally occurring amino acid

<400> SEQUENCE: 105

```
Glu Xaa Asn Xaa Xaa Ala Ile Xaa Xaa Xaa Gly Gly Xaa Pro Xaa Leu
1               5                   10                  15

Val Xaa Leu Leu Xaa Xaa Xaa Xaa Xaa Xaa Xaa Xaa Xaa Xaa Ala Xaa
            20                  25                  30

Xaa Xaa Leu Xaa Asn Leu Xaa Xaa Xaa Xaa
        35                  40
```

<210> SEQ ID NO 106
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (4)..(4)
<223> OTHER INFORMATION: Xaa is any naturally occurring amino acid
<220> FEATURE:
<221> NAME/KEY: MOD_RES
<222> LOCATION: (26)..(26)
<223> OTHER INFORMATION: Xaa is any naturally occurring amino acid
<220> FEATURE:
<221> NAME/KEY: MOD_RES
<222> LOCATION: (29)..(30)
<223> OTHER INFORMATION: Xaa is any naturally occurring amino acid
<220> FEATURE:
<221> NAME/KEY: MOD_RES
<222> LOCATION: (33)..(33)
<223> OTHER INFORMATION: Xaa is any naturally occurring amino acid
<220> FEATURE:
<221> NAME/KEY: MOD_RES
<222> LOCATION: (36)..(36)
<223> OTHER INFORMATION: Xaa is any naturally occurring amino acid
<220> FEATURE:
<221> NAME/KEY: MOD_RES
<222> LOCATION: (40)..(41)
<223> OTHER INFORMATION: Xaa is any naturally occurring amino acid

<400> SEQUENCE: 106

```
Glu Ala Asn Xaa Leu Ala Ile Arg Glu Ser Gly Gly Ile Pro Ala Leu
1               5                   10                  15

Val Arg Leu Leu Ser Ser Asn Asn Glu Xaa Ile Leu Xaa Xaa Ala Thr
            20                  25                  30

Xaa Thr Leu Xaa Asn Leu Ala Xaa Xaa Gly
        35                  40
```

<210> SEQ ID NO 107
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (2)..(2)
<223> OTHER INFORMATION: Xaa is any naturally occurring amino acid
<220> FEATURE:
<221> NAME/KEY: MOD_RES
<222> LOCATION: (4)..(5)
<223> OTHER INFORMATION: Xaa is any naturally occurring amino acid
<220> FEATURE:
<221> NAME/KEY: MOD_RES
<222> LOCATION: (6)..(6)
<223> OTHER INFORMATION: Xaa is Ala, Phe, Gly, Ile, Leu, Met, Pro, Thr, Val, Trp or Tyr
<220> FEATURE:
<221> NAME/KEY: MOD_RES
<222> LOCATION: (8)..(8)
<223> OTHER INFORMATION: Xaa is any naturally occurring amino acid
<220> FEATURE:
<221> NAME/KEY: MOD_RES
<222> LOCATION: (9)..(9)
<223> OTHER INFORMATION: Xaa is Ala, Cys, Asp, Glu, Gly, His, Lys, Asn, Pro, Gln, Arg, Ser, Thr or Tyr
<220> FEATURE:
<221> NAME/KEY: MOD_RES
<222> LOCATION: (10)..(10)
<223> OTHER INFORMATION: Xaa is any naturally occurring amino acid
<220> FEATURE:
<221> NAME/KEY: MOD_RES
<222> LOCATION: (12)..(13)
<223> OTHER INFORMATION: Xaa is Ala, Phe, Gly, Ile, Leu, Met, Pro, Thr, Val, Trp or Tyr
<220> FEATURE:
<221> NAME/KEY: MOD_RES
<222> LOCATION: (15)..(15)
<223> OTHER INFORMATION: Xaa is any naturally occurring amino acid
<220> FEATURE:
<221> NAME/KEY: MOD_RES
<222> LOCATION: (18)..(18)
<223> OTHER INFORMATION: Xaa is Ala, Cys, Asp, Glu, Gly, His, Lys, Asn, Pro, Gln, Arg, Ser, Thr or Tyr
<220> FEATURE:
<221> NAME/KEY: MOD_RES
<222> LOCATION: (21)..(21)
<223> OTHER INFORMATION: Xaa is any naturally occurring amino acid
<220> FEATURE:
<221> NAME/KEY: MOD_RES
<222> LOCATION: (22)..(22)
<223> OTHER INFORMATION: Xaa is Ala, Cys, Asp, Glu, Gly, His, Lys, Asn, Pro, Gln, Arg, Ser, Thr or Tyr
<220> FEATURE:
<221> NAME/KEY: MOD_RES
<222> LOCATION: (23)..(23)
<223> OTHER INFORMATION: Xaa is any naturally occurring amino acid
<220> FEATURE:
<221> NAME/KEY: MOD_RES
<222> LOCATION: (24)..(24)
<223> OTHER INFORMATION: Xaa is Ala, Cys, Asp, Glu, Gly, His, Lys, Asn, Pro, Gln, Arg, Ser, Thr or Tyr
<220> FEATURE:
<221> NAME/KEY: MOD_RES
<222> LOCATION: (25)..(26)
<223> OTHER INFORMATION: Xaa is any naturally occurring amino acid
<220> FEATURE:
<221> NAME/KEY: MOD_RES
<222> LOCATION: (27)..(27)
<223> OTHER INFORMATION: Xaa is Ala, Phe, Gly, Ile, Leu, Met, Pro, Thr, Val, Trp or Tyr
<220> FEATURE:
<221> NAME/KEY: MOD_RES
<222> LOCATION: (28)..(30)
<223> OTHER INFORMATION: Xaa is any naturally occurring amino acid
<220> FEATURE:
<221> NAME/KEY: MOD_RES
<222> LOCATION: (32)..(32)
<223> OTHER INFORMATION: Xaa is Ala, Phe, Gly, Ile, Leu, Met, Pro, Thr, Val, Trp or Tyr
<220> FEATURE:
<221> NAME/KEY: MOD_RES
<222> LOCATION: (33)..(33)

<223> OTHER INFORMATION: Xaa is any naturally occurring amino acid
<220> FEATURE:
<221> NAME/KEY: MOD_RES
<222> LOCATION: (36)..(36)
<223> OTHER INFORMATION: Xaa is any naturally occurring amino acid
<220> FEATURE:
<221> NAME/KEY: MOD_RES
<222> LOCATION: (38)..(38)
<223> OTHER INFORMATION: Xaa is Ala, Phe, Gly, Ile, Leu, Met, Pro, Thr, Val, Trp or Tyr
<220> FEATURE:
<221> NAME/KEY: MOD_RES
<222> LOCATION: (39)..(42)
<223> OTHER INFORMATION: Xaa is any naturally occurring amino acid

<400> SEQUENCE: 107

```
Asn Xaa Gln Xaa Xaa Xaa Val Xaa Xaa Xaa Gly Xaa Xaa Pro Xaa Leu
1               5                   10                  15

Val Xaa Leu Leu Xaa Xaa Xaa Xaa Xaa Xaa Xaa Xaa Xaa Xaa Ala Xaa
            20                  25                  30

Xaa Ala Leu Xaa Asn Xaa Xaa Xaa Xaa Xaa
        35                  40
```

<210> SEQ ID NO 108
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (4)..(4)
<223> OTHER INFORMATION: Xaa is any naturally occurring amino acid
<220> FEATURE:
<221> NAME/KEY: MOD_RES
<222> LOCATION: (26)..(30)
<223> OTHER INFORMATION: Xaa is any naturally occurring amino acid
<220> FEATURE:
<221> NAME/KEY: MOD_RES
<222> LOCATION: (33)..(33)
<223> OTHER INFORMATION: Xaa is any naturally occurring amino acid
<220> FEATURE:
<221> NAME/KEY: MOD_RES
<222> LOCATION: (36)..(36)
<223> OTHER INFORMATION: Xaa is any naturally occurring amino acid
<220> FEATURE:
<221> NAME/KEY: MOD_RES
<222> LOCATION: (40)..(41)
<223> OTHER INFORMATION: Xaa is any naturally occurring amino acid

<400> SEQUENCE: 108

```
Asn Glu Gln Xaa Gln Ala Val Ile Asp Ala Gly Gly Leu Pro Ala Leu
1               5                   10                  15

Val Gln Leu Leu Ser Ser Pro Asn Glu Xaa Xaa Xaa Xaa Xaa Ala Ala
            20                  25                  30

Xaa Ala Leu Xaa Asn Leu Ala Xaa Xaa Gly
        35                  40
```

<210> SEQ ID NO 109
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (4)..(4)
<223> OTHER INFORMATION: Xaa is any naturally occurring amino acid
<220> FEATURE:

<221> NAME/KEY: MOD_RES
<222> LOCATION: (7)..(7)
<223> OTHER INFORMATION: Xaa is Ala, Ile, Leu or Val
<220> FEATURE:
<221> NAME/KEY: MOD_RES
<222> LOCATION: (12)..(12)
<223> OTHER INFORMATION: Xaa is Ala, Ile, Leu, Val or Gly
<220> FEATURE:
<221> NAME/KEY: MOD_RES
<222> LOCATION: (13)..(13)
<223> OTHER INFORMATION: Xaa is Ala, Ile, Leu or Val
<220> FEATURE:
<221> NAME/KEY: MOD_RES
<222> LOCATION: (26)..(26)
<223> OTHER INFORMATION: Xaa is any naturally occurring amino acid
<220> FEATURE:
<221> NAME/KEY: MOD_RES
<222> LOCATION: (27)..(28)
<223> OTHER INFORMATION: Xaa is Ala, Ile, Leu or Val
<220> FEATURE:
<221> NAME/KEY: MOD_RES
<222> LOCATION: (29)..(30)
<223> OTHER INFORMATION: Xaa is any naturally occurring amino acid
<220> FEATURE:
<221> NAME/KEY: MOD_RES
<222> LOCATION: (32)..(32)
<223> OTHER INFORMATION: Xaa is Ala, Ile, Leu or Val
<220> FEATURE:
<221> NAME/KEY: MOD_RES
<222> LOCATION: (33)..(33)
<223> OTHER INFORMATION: Xaa is any naturally occurring amino acid
<220> FEATURE:
<221> NAME/KEY: MOD_RES
<222> LOCATION: (36)..(36)
<223> OTHER INFORMATION: Xaa is any naturally occurring amino acid
<220> FEATURE:
<221> NAME/KEY: MOD_RES
<222> LOCATION: (38)..(38)
<223> OTHER INFORMATION: Xaa is Ala, Ile, Leu or Val
<220> FEATURE:
<221> NAME/KEY: MOD_RES
<222> LOCATION: (40)..(42)
<223> OTHER INFORMATION: Xaa is any naturally occurring amino acid

<400> SEQUENCE: 109

```
Asn Glu Gln Xaa Gln Ala Xaa Ile Asp Ala Gly Xaa Xaa Pro Ala Leu
1               5                   10                  15

Val Gln Leu Leu Ser Ser Pro Asn Glu Xaa Xaa Xaa Xaa Xaa Ala Xaa
            20                  25                  30

Xaa Ala Leu Xaa Asn Xaa Ala Xaa Xaa Xaa
        35                  40
```

<210> SEQ ID NO 110
<211> LENGTH: 42
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (4)..(4)
<223> OTHER INFORMATION: Xaa is any naturally occurring amino acid
<220> FEATURE:
<221> NAME/KEY: MOD_RES
<222> LOCATION: (26)..(26)
<223> OTHER INFORMATION: Xaa is any naturally occurring amino acid
<220> FEATURE:
<221> NAME/KEY: MOD_RES
<222> LOCATION: (29)..(30)
<223> OTHER INFORMATION: Xaa is any naturally occurring amino acid
<220> FEATURE:
<221> NAME/KEY: MOD_RES
<222> LOCATION: (33)..(34)
<223> OTHER INFORMATION: Xaa is any naturally occurring amino acid
<220> FEATURE:
<221> NAME/KEY: MOD_RES
<222> LOCATION: (36)..(36)
<223> OTHER INFORMATION: Xaa is any naturally occurring amino acid
<220> FEATURE:
<221> NAME/KEY: MOD_RES
<222> LOCATION: (40)..(41)
<223> OTHER INFORMATION: Xaa is any naturally occurring amino acid

<400> SEQUENCE: 110

```
Asn Glu Gln Xaa Gln Ala Val Ile Asp Ala Gly Ala Leu Pro Ala Leu
1               5                   10                  15

Val Gln Leu Leu Ser Ser Pro Asn Glu Xaa Ile Leu Xaa Xaa Ala Leu
            20                  25                  30

Xaa Xaa Leu Xaa Asn Ile Ala Xaa Xaa Gly
        35                  40
```

<210> SEQ ID NO 111
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

```
Asn Glu Gln Ile Gln Ala Val Ile Asp Ala Gly Gly Leu Pro Ala Leu
1               5                   10                  15

Val Gln Leu Leu Ser Ser Pro Asp Glu Lys Ile Leu Lys Glu Ala Ala
            20                  25                  30

Trp Ala Leu Ser Asn Leu Ala Ser Gly Asn
        35                  40
```

<210> SEQ ID NO 112
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Ser Pro Asn Lys Leu Val Ile Val Glu Ser Asn Ala Ile Gln Arg Phe
1               5                   10                  15

Ile Arg Thr Met Thr His Asn Glu Val Asn Val Gln Glu Val Thr Leu
            20                  25                  30

Gly Thr Ile Gly Ile Ile Thr Asp Asp Gly
        35                  40
```

<210> SEQ ID NO 113
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

```
Glu Ala Pro Thr Ala Met Leu Arg Gln Gln Gln Val Val Ser Val Ile
1               5                   10                  15

Cys Lys Ile Ile Gln Lys Asp Ser Pro Ser Leu Val Phe Pro Cys Val
            20                  25                  30

Arg Val Val His Tyr Ala Ser Leu Cys Thr
        35                  40
```

<210> SEQ ID NO 114
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Asn Pro Gln Ile Gln Ala Val Ile Asp Ala Gly Ala Leu Pro Pro Leu
1               5                   10                  15

Val Glu Leu Leu Ser Ser Pro Asp Glu Lys Ile Gln Lys Glu Ala Leu
            20                  25                  30

Trp Ala Leu Ser Asn Ile Thr Ser Gly Gly
        35                  40
```

<210> SEQ ID NO 115
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

```
Asp Glu Pro Thr Asp Val Leu Val Glu Ser Asn Val Val Lys Arg Phe
1               5                   10                  15

Ile Asn Phe Ile Thr His Ala Glu Phe Ser Val Leu Glu Asp Thr Ala
            20                  25                  30

Arg Thr Ile Gly Tyr Leu Ala Ala Asp Thr
        35                  40
```

<210> SEQ ID NO 116
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

```
Ser Asp Lys Pro Lys Tyr Ile Leu Gln Cys Gln Ile Ile Ser Val Ile
1               5                   10                  15

Cys Ser Cys Met Gln Lys Asn Lys Asn Asp Leu Val Phe Val Ser Val
            20                  25                  30

Asp Gly Val Thr Ala Val Thr Ala Asn
        35                  40
```

<210> SEQ ID NO 117
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Glu Ala Asn Lys Leu Ala Ile Arg Leu Ser Gly Gly Ile Pro Ala Leu
1               5                   10                  15

Val Gln Leu Leu Ser Ser Asn Asp Glu Lys Ile Leu Glu Cys Ala Thr
            20                  25                  30

Gly Thr Leu His Asn Leu Ala Leu Cys Asn
```

35 40

<210> SEQ ID NO 118
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

Pro Glu Ser Arg Met Ile Val Phe Glu Ala Asn Leu Leu Gln Lys Ile
1 5 10 15

Gly Arg Thr Met Gly Pro Asp Val Val Asn Leu Val Arg Ala Thr Ala
20 25 30

Cys Ala Ile Arg Ile Val Ser Cys His His
35 40

<210> SEQ ID NO 119
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

Gln Met Ala Leu Ala Pro Leu Val Gln Asn Tyr Val Val Ala Arg Met
1 5 10 15

Ile Lys His Ile Arg Tyr Pro Arg Trp Glu Val Thr Lys Tyr Cys Ile
20 25 30

Trp Val Val Ser Val Met Thr Tyr Asp Gln
35 40

<210> SEQ ID NO 120
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

Glu Leu Pro Gln Met Thr Gln Gln Leu Asn Ser Asp Asp Met Gln Glu
1 5 10 15

Gln Leu Ser Ala Thr Val Lys Phe Arg Gln Ile Leu Ser Arg Asp Gly
20 25 30

Asn Glu

<210> SEQ ID NO 121
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 121

Glu Gln Lys Gln Ala Val Lys Glu Ala Gly Ala Leu Glu Lys Leu Glu
1               5                   10                  15

Gln Leu Gln Ser His Glu Asn Glu Lys Ile Gln Lys Glu Ala Gln Glu
            20                  25                  30

Ala Leu Glu Lys Gln Phe Ser His
        35                  40
```

DESIGNED ARMADILLO REPEAT PROTEINS

FIELD OF THE INVENTION

The present invention relates to a novel method for the generation of target-specific binding molecules based on armadillo repeat proteins and the designed armadillo repeat proteins so obtained.

BACKGROUND OF THE INVENTION

Protein-protein interactions play a key role in biology and related fields, from medicine to diagnostics to research. Specific molecules able to recognize a target protein can be obtained by established selection techniques (e.g. phage display, ribosome display, mRNA display, DNA display) applied to libraries of antibodies or alternative binding molecules. High specificity and selectivity are achieved by these strategies, but the binding mode of the molecules is often difficult to predict. A single epitope can be targeted in different ways, thus prediction of the residues involved in binding and of the interactions exploited is often not achievable, relegating the rational approach and selection process of these binders to a "case by case" methodology. Each new binding molecule will have to be individually created by selection procedure, it will bind a target protein in a different conformation each time, and its cross reactivity will have to be individually tested in each case. A much simpler case is provided when the target provides a continuous stretch of amino acids along the primary sequence (a linear epitope). The recognition of linear epitopes, in natural proteins, can be considered as a model for general recognition of peptides. With almost no secondary structure present and the possibility to be bound in extended conformation, all side chains of a peptide are potentially available for recognition at the amino acid level by a binding molecule in a precise and reproducible manner.

Among natural peptide binding proteins, including small adapter domains (e.g. SH2, SH3, PDZ, WW), MHCI and MHCII proteins, and several repeat proteins families (e.g. TPR, armadillo, WD40), armadillo repeat proteins possess characteristics making them suitable to build a scaffold to generate modular peptide binding proteins. The generation of such a scaffold based on armadillo repeat proteins would also take advantage of the methods developed for the consensus design of repeat proteins and the generation of repeat protein libraries described in WO 02/20565. Armadillo repeat proteins are abundant eukaryotic proteins involved in a broad range of functions (Coates, J. C., Trends Cell Biol 13:463-71, 2003), from transcription regulation (β-catenin) to cell adhesion (plakophilin), tumor suppressor activity (Adenomatous Polyposis Colon APC), and nucleo-cytoplasmic transport (importin-α). These proteins are characterized by tandem repeat units of approximately 42 amino acids that were first discovered in the product of *Drosophila melanogaster* segmentation polarity gene Armadillo. Armadillo repeat proteins participate in protein-protein interactions and the domain formed by the armadillo repeat units is usually involved in the recognition process. The armadillo repeat domain, originally defined by limited proteolysis, forms a right-handed superhelical structure, as shown initially by the crystal structures of β-catenin (Huber A. H. and Nelson W. J., Cell 90:871-82, 1997) and importin-α (Conti E. et al., Cell 94:193-204, 1998) (FIG. 1). Every repeat unit is composed by three α helices, named H1, H2, H3 (FIG. 2) and several repeat units stack to form a compact domain. Specialized repeat units are present at the N- and C-termini of these armadillo repeat domains, probably protecting the otherwise exposed hydrophobic core (FIG. 1).

Crystal structures of complexes of armadillo repeat proteins with their target proteins reveal that most of the targets are bound in an extended conformation inside a groove along the surface formed by the H3 helices (FIGS. 1 and 2). An asparagine residue, conserved in almost every repeat unit at the C-terminal part of H3, contacts the main chain of the target, while additional interactions to target side chains are provided by neighboring residues. A single repeat unit is, in general, responsible for the interaction with two target amino acid residues. As in the case of other repeat protein families which have been structurally characterized (e.g. TPR, D'Andrea L. D. and Regan D., Trends Biochem Sci 28:655-62, 2003; Ankyrin repeats, Mosavi L. K. et al., Protein Sci 13:1435-48, 2004; Leucine Rich Repeats, Kob B. and Kajava A. V., Curr Opin Struct Biol 11:725-32, 2001), the interactions are generally provided by residues on the surface of secondary structure elements (FIG. 2) instead of residues present in flexible loops like in the case of antibodies. The general principle to use repeat proteins as scaffold to generate binding molecules was described (Forrer et al., FEBS Lett. 539(1-3):2-6, 2003) and, in the case of designed ankyrin repeat proteins, high affinity binders were successfully selected from such a designed ankyrin repeat protein library (Binz et al., Nat Biotechnol. 22(5):575-82, 2004).

Armadillo repeat proteins, such as β-catenin and importin-α, are able to bind different types of peptides, relying on a constant way of binding of the peptide backbone without requiring specific conserved side chains or interactions with free N- or C-termini of a peptide (FIG. 3). The possibility of recognizing a peptide residue by residue, combined with the intrinsic modularity of a repeat protein, can make the armadillo repeat proteins promising candidates for the design of a generic scaffold for peptide binding. In addition, a remarkable $K_D$ as low as 10-20 nM has been reported for importin-α (Catimel B. et al., J Biol Chem 276: 34189-98, 2001) for binding of a target peptide, showing the possibility of achieving high peptide-binding affinities with designed armadillo repeat proteins.

Thus, the technical problem underlying the present invention is to identify novel approaches for the efficient generation of target-specific peptide-binding proteins based on armadillo repeat proteins. The solution to this technical problem is achieved by providing the embodiments characterized in the claims.

SUMMARY OF THE INVENTION

The present invention relates to target-specific designed binding proteins based on armadillo repeat proteins, and to a method of generating them. Designed armadillo repeat proteins are based on consensus sequences of single armadillo repeat units. In particular, the invention relates to a collection of armadillo repeat proteins comprising at least one repeat domain comprising at least two consecutive repeat modules derived from consensus sequences of armadillo repeat units, wherein at least one of said armadillo repeat proteins is able to bind a target molecule. Designed armadillo repeat proteins in such a collection differ in at least one amino acid position from each other. Preferably, designed armadillo repeat proteins in such a collection differ in at least one amino acid position corresponding to a target interaction position form each other. More preferably, said target molecule is a target (poly)peptide. Even more preferably, said target molecule is a target (poly)peptide, wherein the part of said (poly)peptide bound by said armadillo repeat protein is in an extended conformation.

More specifically, the invention relates to a collection of armadillo repeat proteins comprising repeat modules with the armadillo repeat sequence motif

```
1         10              20                30
pxpxxaaxxx ±G±aaPxLapLL x±±±pxx±±±xxaxxx

          40                      42
AaxxLxNaxx ±±±±±±±±±±±±±±±±±±±±xx
```

wherein "x" denotes any amino acid, "±" denotes any amino acid or a deletion ("±" is not counted in the numbering of the positions), "a" denotes an amino acid with an apolar side chain, and "p" denotes a residue with a polar side chain. Examples of such designed armadillo repeat proteins are described hereinafter.

In preferred collections, each repeat module has an amino acid sequence, wherein at least 70% of the amino acid residues correspond either (i) to consensus amino acid residues deduced from the amino acid residues found at the corresponding positions of at least two armadillo repeat units; or (ii) to the amino acid residues found at the corresponding positions in one armadillo repeat unit.

Preferably, such an armadillo repeat unit is a naturally occurring armadillo repeat unit.

In a collection of the invention, positions, which are not indicated to be assigned to a specific amino acid, are randomized, i.e. may be occupied by different amino acids. Particularly preferred are amino acids in such randomized positions which correspond to the amino acid(s) present at corresponding amino acid positions in naturally occurring members of the armadillo repeat protein family.

Preferably, designed armadillo repeat proteins of the invention further comprise an N- and/or a C-terminal capping module having an amino acid sequence different from any one of the (internal) repeat modules. In particular, such N- and C-terminal capping modules have an amino acid sequence, wherein at least 50%, preferably at least 60%, even more preferably at least 70% of the amino acid residues correspond either (i) to consensus amino acid residues deduced from the amino acid residues found at the corresponding positions of at least two naturally occurring repeat units or capping units; or (ii) to the amino acid residues found at the corresponding positions in one naturally occurring repeat unit or capping unit.

The invention further relates to collections of nucleic acid molecules encoding the mentioned designed repeat proteins comprising repeat modules with the armadillo repeat sequence motif, to methods of obtaining such collections of armadillo repeat proteins, to single designed armadillo repeat proteins from these collections binding a target molecule, and to nucleic acid molecules encoding these designed armadillo repeat proteins.

Importin-α (PDB ID 1 EE5) and β-catenin (PDB ID 1I7W) in a ribbon representation. The N-terminal and C-terminal capping repeats are depicted in dark grey and indicated by N and C, respectively. The target peptides are black and shown in a stick representation.

Figure 2:
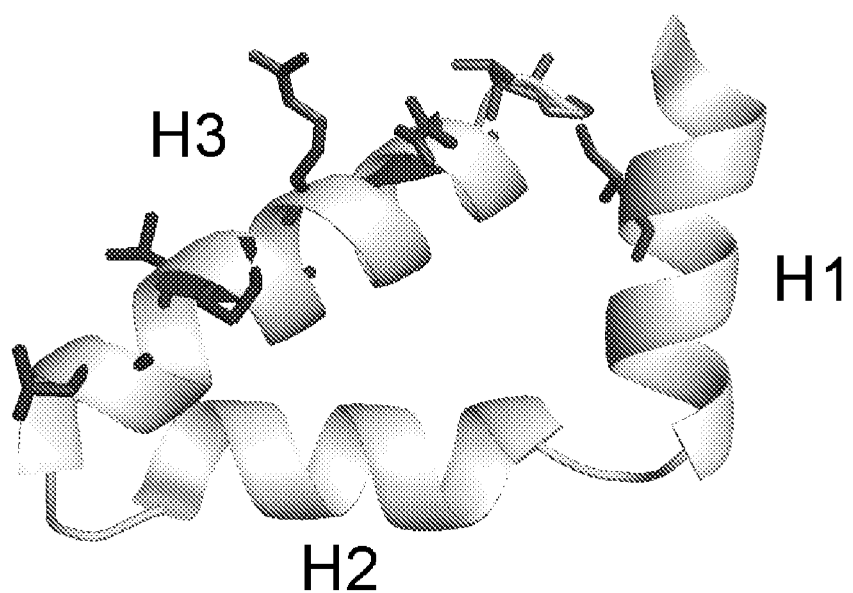

FIG. 2. Armadillo Repeat Unit.

Secondary structure elements of an armadillo repeat unit (repeat 6, 1 EE5) in a ribbon representation: α-helices H1, H2 and H3 are indicated. Residues at the positions involved in binding to target peptides (target interaction residues) are depicted as sticks in dark gray. These target interaction residues are found at position 4 in H1, positions 26, 29, 30, 33, 36, 37, 40 in H3 and position 41 in the loop between H3 and H1 of the next repeat.

Figure 3:
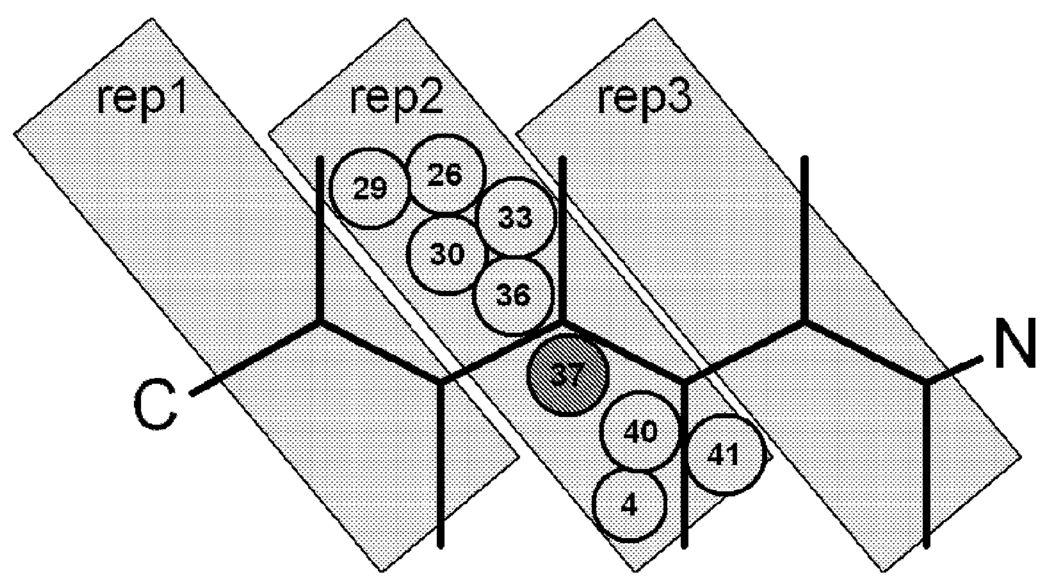

FIG. 3. Armadillo Repeat Protein Binding Mode.

Schematic drawing of the interaction of an armadillo repeat protein with a target peptide. The target peptide (shown in black) is bound in an antiparallel way with respect to the peptide backbone of the protein. N and C indicate N- and C-termini of the peptide, respectively, with the amino acid side chains shown as sticks pointing toward the extremities of the repeats. rep1, rep2 and rep3 indicate three consecutive armadillo repeats. The residues of armadillo repeats involved in binding occupy specific positions inside the single repeat sequences, indicated by the numbered circles in rep2. The residue at position 37 is responsible for the binding of the peptide main chain and is depicted in dark grey; the other positions are involved in recognition of the peptide side chains.

Figure 4:
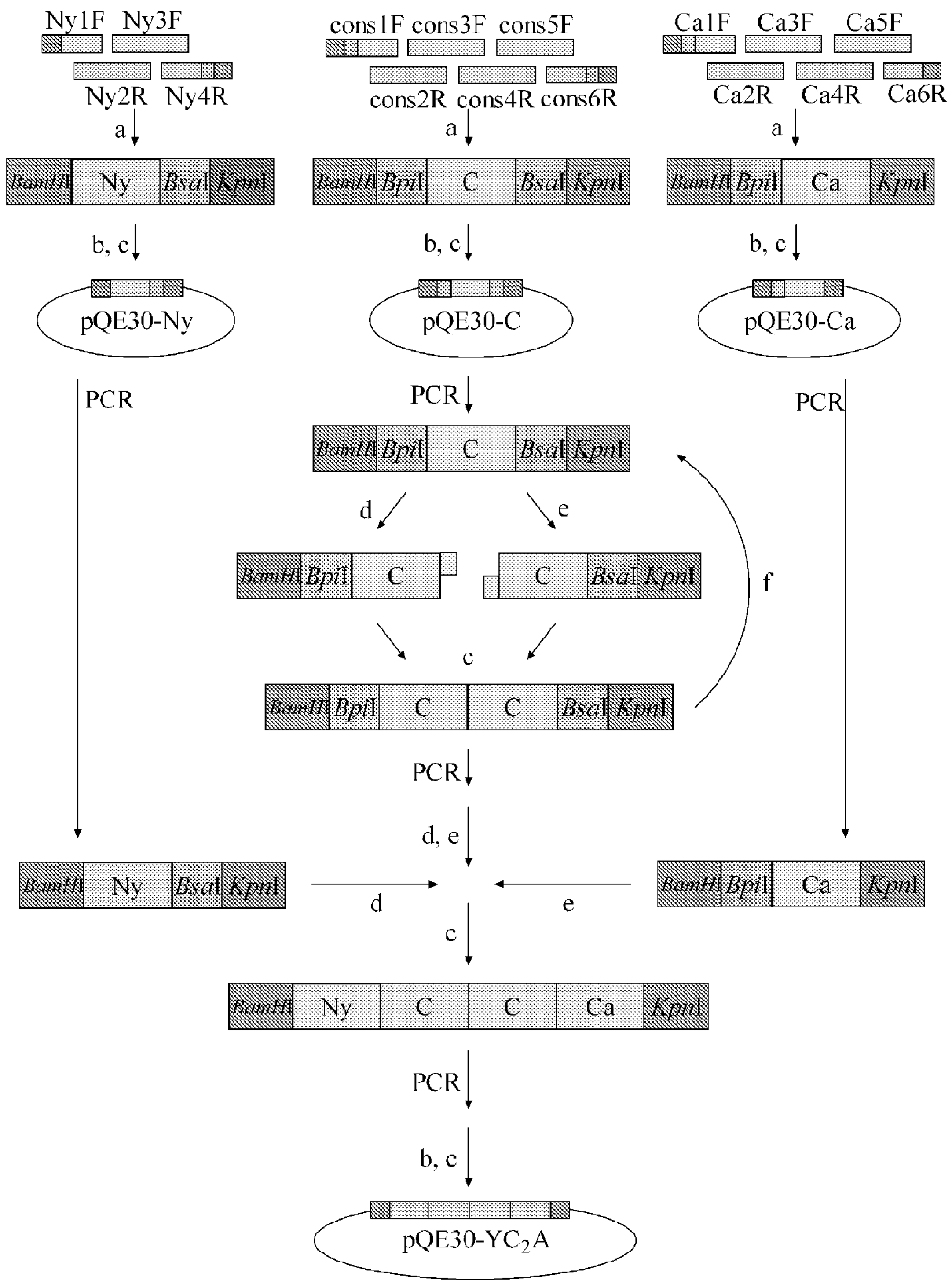

FIG. 4. Scheme of the Assembly Strategy for Designed Armadillo Repeat Protein Genes.

The construction of $YC_2A$ from the internal module C, the N-terminal cap Ny and the C-terminal cap Ca is shown as an example. Oligonucleotides, indicated by their names, are assembled to an internal or terminal capping module by PCR. The single modules contain restriction sites for BamHI and KpnI for insertion in the vector and the type IIS restriction enzymes BsaI and BpiI for ligation of the modules.

a: assembly PCR, b: digestion with BamHI and KpnI, c: ligation, d: digestion with BsaI, e: digestion with BpiI, f: amplification and additional digestion/ligation cycles.

Figure 5:
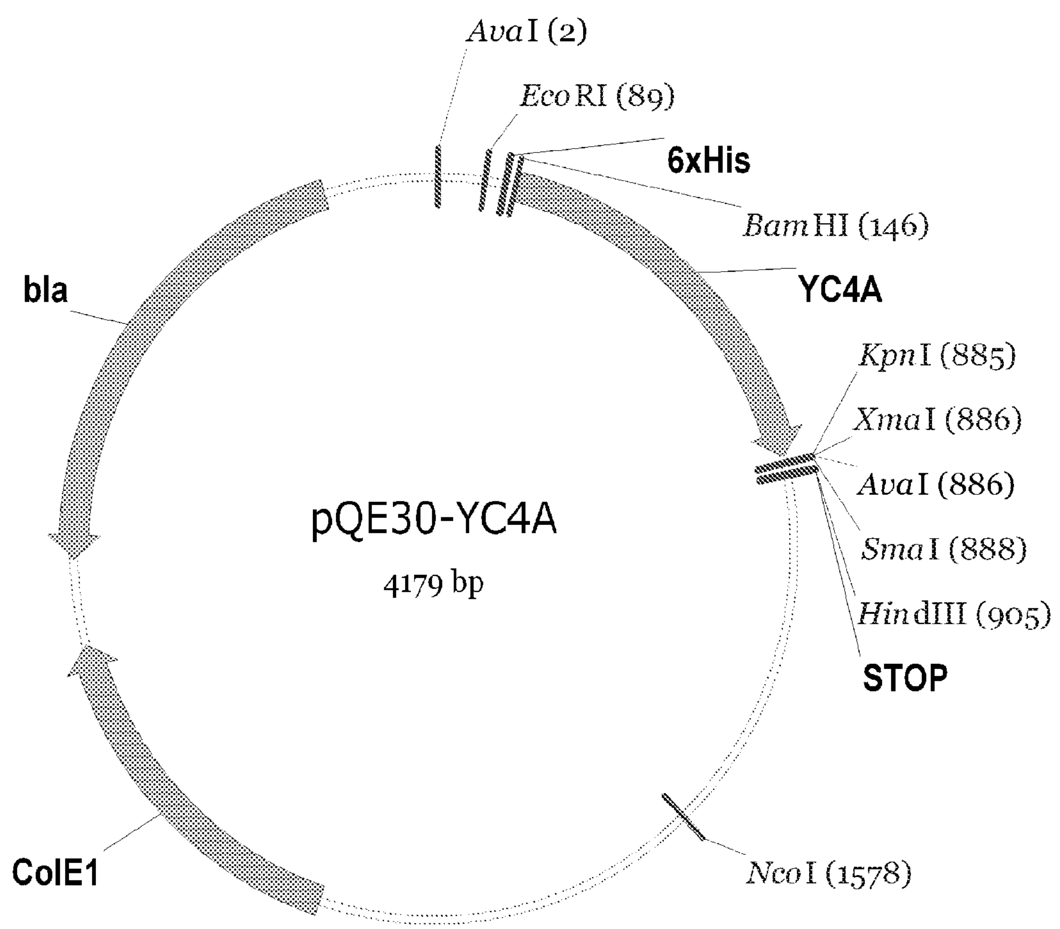

FIG. 5. Plasmid pQE30-$YC_4A$.

Scheme of the vector pQE30 containing the gene coding for the $YC_4A$ protein. All the designed armadillo repeat proteins were cloned in the same vector using the same restriction sites (i.e. BamHI and KpnI).

Figure 6:
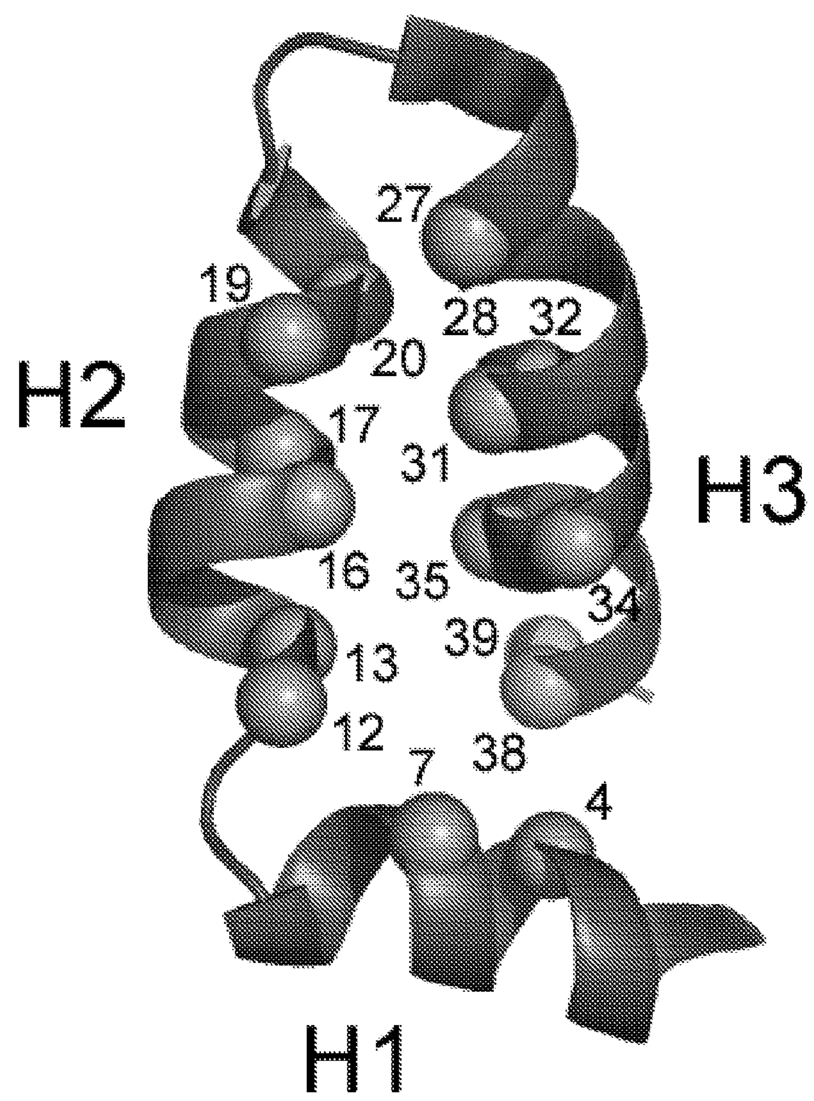

FIG. 6. Positions of Mutations in the Hydrophobic Core of C Type Module.

The helices in a single armadillo repeat are labeled with H1, H2, H3; the hydrophobic core positions of mutations are indicated with spheres and the corresponding amino acid position numbers.

Figure 7:
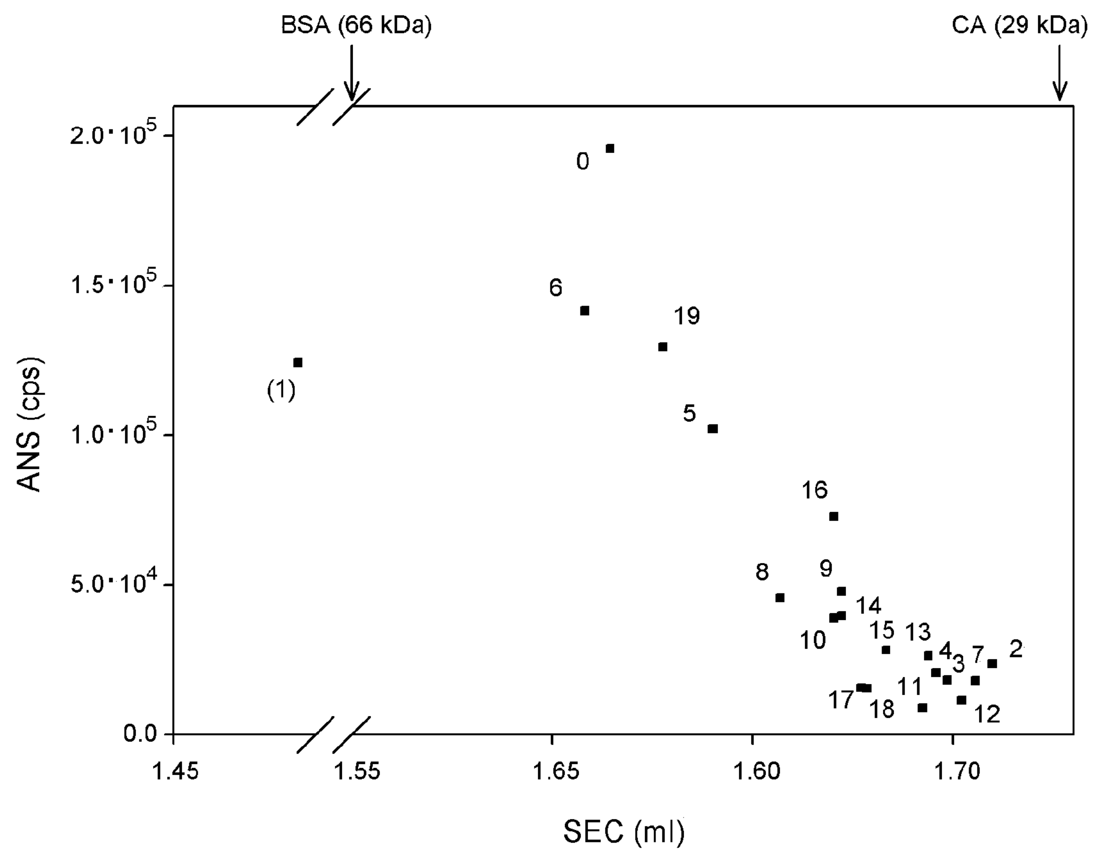

FIG. 7. Experimental Evaluation of Hydrophobic Core Mutants: Elution Volumes in Size Exclusion Chromatography (SEC) and Fluorescence Emission Upon ANS Binding.

The numbers refer to the mutants indicated in Table 10. Each of the mutant proteins contains 4 identical internal repeats and Ny and Ca as capping repeats. 0 indicates the $YC_4A$ protein. All the proteins have a molecular weight of approximately 27 kDa. An Ala->Thr mutation is carried by mut6 at position 15 in repeat 3, mut9 at position 31 in repeat 4, mut10 at position 12 in repeat 1 and mut17 at position 15 in repeat 1. Mut8 has a mutation Gly->Val at position 42 in repeat 4. mut1 (in parentheses) elutes before $YC_4A$ and the other mutants because of its dimeric state. All other mutants were shown to be monomeric by multi-angle light scattering (MALS). Peak values from the SEC elution volumes measured by absorbance at 280 nm and from ANS (1-anilinonaphthalene-8-sulfonate) binding measured by fluorescence intensity are plotted for each tested protein. Errors in the measurements have been estimated with a subset of 6 proteins and 2 different preparations, leading to an average standard deviation of 0.01 ml for SEC and average percentage error of 4% for ANS fluorescence intensity. As reference for the SEC, the peak values for the elution volumes of carbonic anhydrase (CA, MW=29 kDa) of 1.73 ml and bovine serum albumin (BSA, MW=66 kDa) of 1.55 ml are shown.

Figure 8:
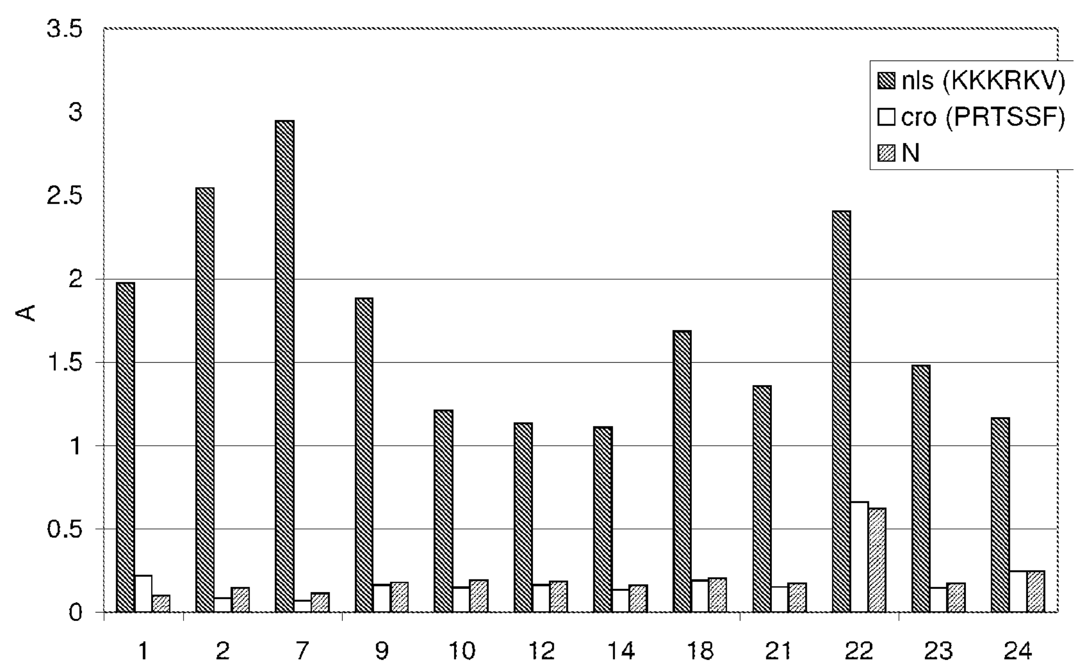

FIG. 8. Specific target binding of selected designed armadillo repeat proteins. The interaction of selected clones with the target peptide (nls, having the sequence KKKRKV SEQ ID NO: 98), a negative control peptide (cro, having the sequence PRTSSF SEQ ID NO: 101) and NeutrAvidin is shown by crude extract ELISA. The biotinylated peptides were immobilized over NeutrAvidin. The numbers refer to single clones selected in ribosome display against the nls target peptide. A=Absorbance and N=NeutrAvidin. Dark gray bars indicate binding to the nls peptide, white bars with lines show binding to the cro peptide and the shaded bars show binding to NeutrAvidin (background binding).

Figure 9:
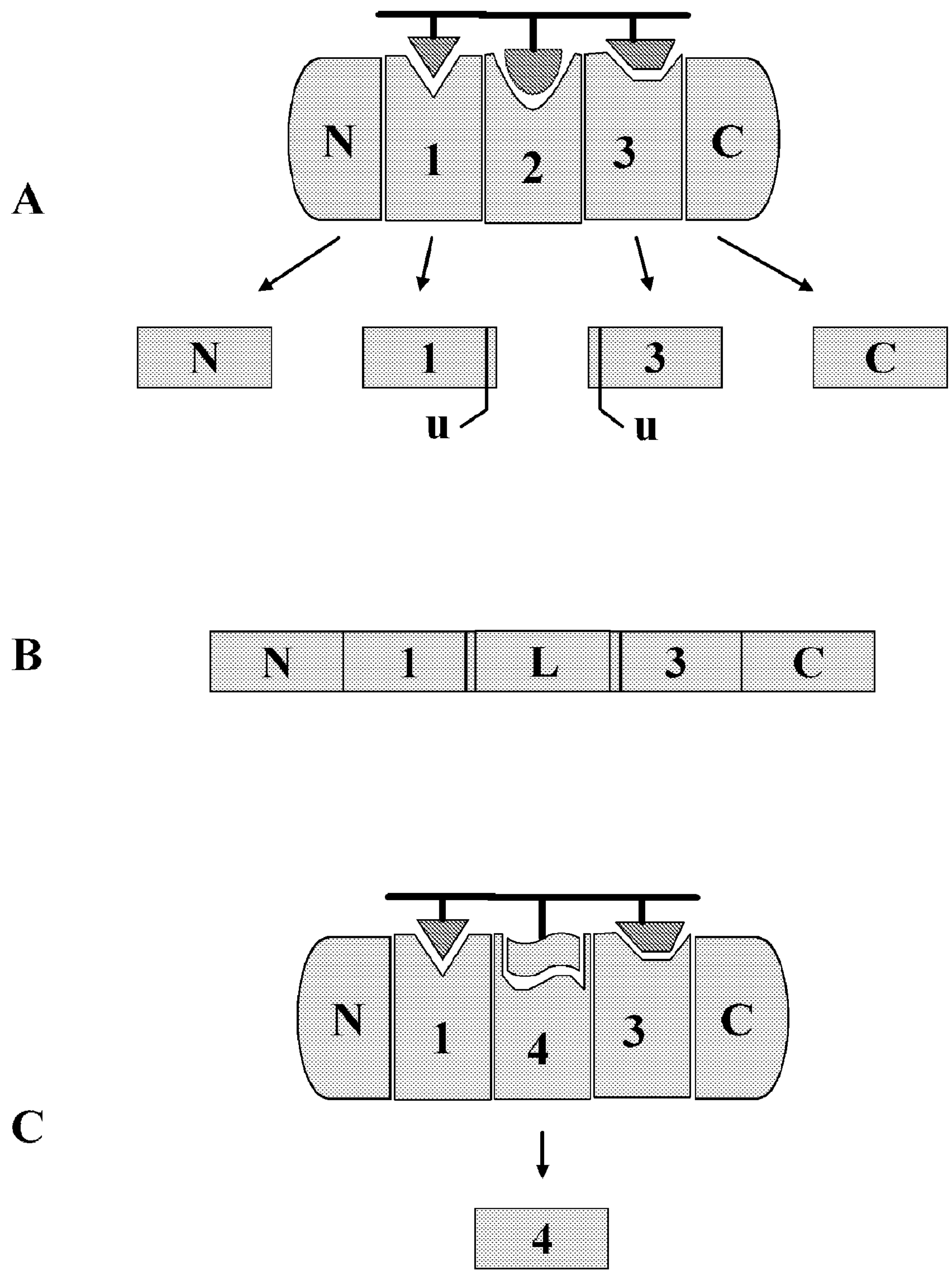

FIG. 9. Selection of Specific Modules.

The scheme shows the procedure for the selection of a repeat module specific for a small peptide target, e.g. a small amino acid stretch, using flanking repeat modules derived from already selected designed armadillo repeat proteins. Pre-selected repeat modules are flanking the repeat module library and provide additional contacts to the target peptide, restricting the selection only to the inner part (for example a dipeptide) of the target (poly)peptide molecule.

A: The DNA sequences corresponding to repeat modules with known specificity are retrieved. 1, 2 and 3 are internal specific repeat modules, N and C are the N- and C-terminal capping repeats. u are unique restriction sites introduced during the assembly of the repeat modules DNA without affecting the protein sequence.

B: The DNA fragments are assembled together with a repeat module library (L) in sequences coding for designed armadillo repeat proteins; the resulting sequences are used for selection.

C: A designed armadillo repeat protein with new specificity is identified upon selection. Taking advantage of the unique restriction sites introduced in step A the DNA sequence of the selected repeat module (4) is recovered and used for the generation of a designed armadillo repeat protein using the binding specificity of the newly selected repeat module.

Figure 10:
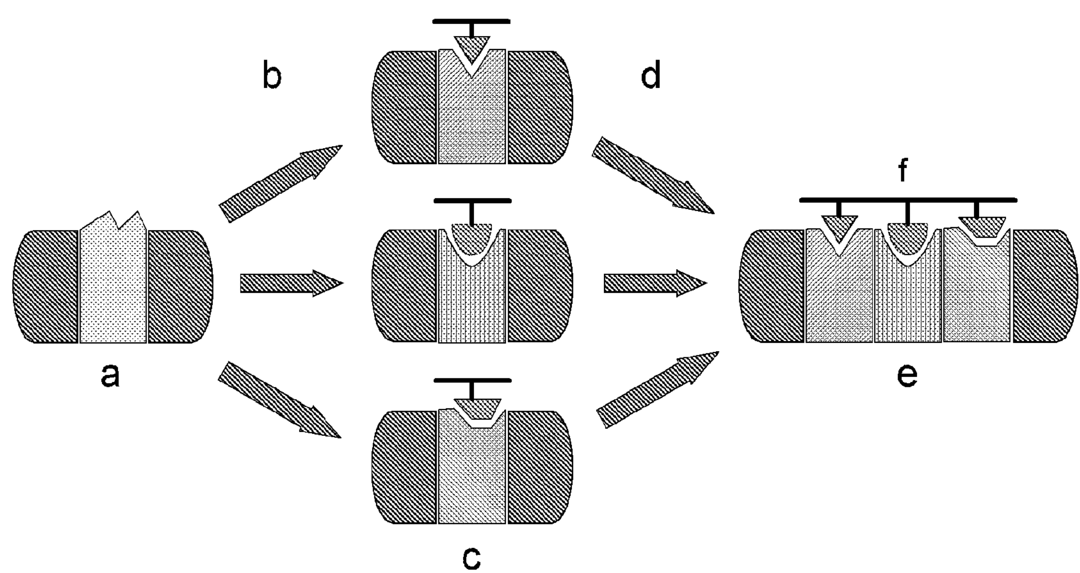

FIG. 10. Combination of Preselected Modules for Recognition of Linear Peptides.

Designed armadillo repeat proteins allow the selection of single repeat modules which specifically recognize short amino acid sequences. The selected peptide specific repeat modules are then combined to form new designed armadillo repeat proteins able to recognize longer peptides, without performing additional selections.

a: library, b: selection, c: selected binders, d: combination of modules, e: combined binder, f: peptide target sequence.

DETAILED DESCRIPTION OF THE INVENTION

The definitions hereinafter for repeat proteins relevant for designed armadillo repeat proteins are based on those in patent application WO 02/20565. Patent application WO 02/20565 further contains a general description of repeat protein features, techniques and applications.

In the context of the present invention, the term “collection” refers to a population comprising at least two different entities or members. Preferably, such a collection comprises at least $10^5$, more preferably more than $10^7$ and most preferably more that $10^9$ different members. A “collection” may as well be referred to as a “library” or a “plurality”.

A “collection” may be a population of, for example, proteins, (poly)peptides or nucleic acids. It may be a stochastic mixture of randomized nucleic acid molecules or mixture of proteins encoded by randomized nucleic acid molecules, but may also be a set of spatially separated nucleic acid molecules or proteins. This dual meaning corresponds to the standard meaning of “collection” as used in molecular biology dealing with preparing and screening expression libraries.

Different members of a collection of proteins or (poly) peptides differ in at least one amino acid position. Preferably, said members differ in at least one amino acid position corresponding to a target interaction position. Different members of a collection of nucleic acids differ in at least one base position. Preferably, said members differ in at lest one base position corresponding to a target interaction position.

The term “repeat proteins” refers to a (poly)peptide/protein comprising one or more repeat domains. Preferably, each of said repeat proteins comprises up to four repeat domains. More preferably, each of said repeat proteins comprises up to two repeat domains. Most preferably, each of the repeat proteins comprises one repeat domain. Furthermore, said repeat protein may comprise additional non-repeat protein domains, (poly)peptide tags and/or (poly)peptide linker sequences. “Armadillo repeat proteins” possess tandem imperfect armadillo repeats of a sequence motif of about 42 amino acids, which consist of three alpha helices. Tandem armadillo repeats fold together and interact extensively with one another to form a right-handed superhelix of helices, which creates a surface for protein-protein interactions. There are many subfamilies of armadillo repeat proteins, such as the beta-catenin, plakoglobin, or importin alpha subfamilies. Armadillo repeat proteins and their subfamilies are well known to the person skilled in the art (Coates, loc. cit., Andrade et al., loc. cit.).

The term “designed repeat protein” refers to a “repeat protein” obtained as the result of an inventive procedure, including, but not limited to, the procedure explained in the present invention. “Designed repeat proteins” are synthetic and neither isolated from nature nor found in nature. They are man-made proteins obtained by expression of correspondingly designed nucleic acids. “Designed nucleic acids” are likewise synthetic (man-made) and neither isolated from nature nor found in nature. Preferably, the expression is done in eukaryotic or bacterial cells, or by using a cell-free in vitro expression system.

The term “(poly)peptide tag” refers to an amino acid sequence attached to a (poly)peptide/protein, wherein said amino acid sequence is useful for the purification, detection, or targeting of said (poly)peptide/protein, or wherein said amino acid sequence improves the physicochemical behavior of the (poly)peptide/protein, or wherein said amino acid sequence possesses an effector function. The individual (poly)peptide tags, moieties and/or domains of a repeat protein may be connected to each other directly or via (poly) peptide linkers.

The term “(poly)peptide linker” refers to an amino acid sequence, which is able to link, for example, two protein domains, a (poly)peptide tag and a protein domain or two sequence tags. Such additional domains, tags and linkers are known to the person skilled in the relevant art. A list of example is provided in the description of the patent application WO 02/20565.

In the context of the present invention, the term "(poly) peptide" relates to a molecule consisting of one or more chains of multiple, i.e. two or more, amino acids linked via peptide bonds.

The term "protein" refers to a (poly)peptide, wherein at least part of the (poly)peptide has, or is able to, acquire a defined three-dimensional arrangement by forming secondary, tertiary, or quaternary structures within and/or between its (poly)peptide chain(s). If a protein comprises two or more (poly)peptides, the individual (poly)peptide chains may be linked non-covalently or covalently, e.g. by a disulfide bond between two (poly)peptides. A part of a protein, which individually has, or is able to acquire a defined three-dimensional arrangement by forming secondary or tertiary structures, is termed "protein domain". Such protein domains are well known to the practitioner skilled in the art.

The term "repeat domain" refers to a protein domain comprising two or more consecutive repeat units (modules) as structural units, wherein said structural units have the same fold, and stack tightly to create, for example, a superhelical structure having a joint hydrophobic core.

The term "structural unit" refers to a locally ordered part of a (poly)peptide, formed by three-dimensional interactions between two or more segments of secondary structure that are near one another along the (poly)peptide chain. Such a structural unit comprises a structural motif. The term "structural motif" refers to a three-dimensional arrangement of secondary structure elements present in at least one structural unit. For example, the structural motif repetitively present in armadillo proteins consists of three α helices forming approximately the three sides of a triangle (FIG. 2). Structural motifs are well known to the person skilled in the art. Structural units alone are not able to acquire a defined three-dimensional arrangement; however, their consecutive arrangement as repeat modules in a repeat domain leads to a mutual stabilization of neighboring units resulting in a superhelical structure.

The term "repeat unit" refers to amino acid sequences comprising sequence motifs of one or more naturally occurring proteins, wherein said "repeat units" are found in multiple copies, and which exhibit a defined folding topology common to all said motifs determining the fold of the protein. Such repeat units comprise framework residues and interaction residues. Examples of such repeat units include, apart from armadillo repeat units, leucine-rich repeat units, ankyrin repeat units, tetratricopeptide repeat units, HEAT repeat units, and leucine-rich variant repeat units. Naturally occurring proteins containing two or more such repeat units are referred to as "naturally occurring repeat proteins". The amino acid sequences of the individual repeat units of a repeat protein may have a significant number of mutations, substitutions, additions and/or deletions when compared to each other, while still substantially retaining the general pattern, or motif, of the repeat units.

The term "framework residues" relates to amino acid residues of the repeat units, or the corresponding amino acid residues of the repeat modules, which contribute to the folding topology, i.e. which contribute to the fold of said repeat unit (or module) or which contribute to the interaction with a neighboring unit (or module). Such contribution might be the interaction with other residues in the repeat unit (module), or the influence on the polypeptide backbone conformation as found in α-helices or β-sheets, or amino acid stretches forming linear polypeptides or loops.

The term "target interaction residues" refers to amino acid residues of the repeat units, or the corresponding amino acid residues of the repeat modules, which contribute to the interaction with target substances. Such contribution might be the direct interaction with the target substances, or the influence on other directly interacting residues, e.g. by stabilizing the conformation of the (poly)peptide of a repeat unit (module) to allow or enhance the interaction of directly interacting residues with said target. Such framework and target interaction residues may be identified by analysis of the structural data obtained by the physicochemical methods referred to above, or by comparison with known and related structural information well known to practitioners in structural biology and/or bioinformatics.

Preferably, the repeat units used for the deduction of a repeat sequence motif are homologous repeat units, wherein the repeat units comprise the same structural motif and wherein more than 70% of the framework residues of said repeat units are homologous. Preferably, more than 80% of the framework residues of said repeat units are homologous. Most preferably, more than 90% of the framework residues of said repeat units are homologous. Computer programs to determine the percentage of homology between polypeptides, such as Fasta, Blast or Gap, are known to the person skilled in the art.

The term "repeat sequence motif" refers to an amino acid sequence, which is deduced from one or more repeat units. Such repeat sequence motifs comprise framework residue positions and target interaction residue positions. Said framework residue positions correspond to the positions of framework residues of the repeat units. Likewise, said target interaction residue positions correspond to the positions of target interaction residues of the repeat units. Repeat sequence motifs comprise fixed positions and randomized positions. The term "fixed position" refers to an amino acid position in a repeat sequence motif, wherein said position is set to a particular amino acid. Most often, such fixed positions correspond to the positions of framework residues. The term "randomized position" refers to an amino acid position in a repeat sequence motif, wherein two or more amino acids are allowed at said amino acid position, for example, wherein any of the usual twenty naturally occurring amino acids are allowed, or wherein most of the twenty naturally occurring amino acids are allowed, such as amino acids other than cysteine, or amino acids other than glycine, cysteine and proline, as will be explained in more detail hereinbelow. Most often, such randomized positions correspond to the positions of target interaction residues. However, some positions of framework residues may also be randomized. Amino acid sequence motifs are well known to the practitioner in the art.

The term "folding topology" refers to the tertiary structure of said repeat units. The folding topology will be determined by stretches of amino acids forming at least parts of α-helices or β-sheets, or amino acid stretches forming linear polypeptides or loops, or any combination of α-helices, β-sheets and/or linear polypeptides/loops.

The term "consecutive" refers to an arrangement, wherein the repeat units or repeat modules described below are arranged in tandem. In designed repeat proteins, there are at least 2, usually about 2 to 6, in particular at least about 6, frequently 20 or more repeat units. In most cases, repeat units will exhibit a high degree of sequence identity (same amino acid residues at corresponding positions) or sequence similarity (amino acid residues being different, but having similar physicochemical properties), and some of the amino acid residues might be key residues being strongly conserved in the different repeat units found in naturally occurring proteins. However, a high degree of sequence variability by amino acid insertions and/or deletions, and/or substitutions between the different repeat units found in naturally occurring proteins will be possible as long as the common folding topology is maintained.

Methods for directly determining the folding topology of repeat proteins by physico-chemical means such as X-ray crystallography, NMR or CD spectroscopy, are well known to the practitioner skilled in the art. Methods for identifying and determining repeat units or repeat sequence motifs or for identifying families of related proteins comprising such repeat units or motifs, such as homology searches (BLAST etc.), are well established in the field of bioinformatics, and are well known to the practitioner in the art. The step of refining an initial repeat sequence motif may comprise an iterative process.

The term "repeat modules" refers to the repeated amino acid sequences of the designed repeat proteins of the present invention, which are derived from the repeat units (FIG. 2) of naturally occurring armadillo repeat proteins. Each repeat module comprised in a repeat domain is derived from one or more repeat units of the family or subfamily of naturally occurring armadillo repeat proteins.

The term "family of naturally occurring repeat proteins" refers to a group of naturally occurring repeat proteins, wherein the members of said group comprise similar repeat units. The term "subfamily" refers to a subgroup of a family of naturally occurring repeat proteins.

"Repeat modules" may comprise positions with amino acid residues present in all copies of corresponding repeat modules ("fixed positions") and positions with differing or "randomized" amino acid residues ("randomized positions").

The term "differ in at least one position" refers to a collection of designed repeat proteins, which have at least one position wherein more than one amino acid may be found in different repeat proteins of said collection. Preferably, such positions are randomized. Preferably, the randomized positions vary additionally between repeat modules within one designed repeat domain. Preferably, such positions may be fully randomized, i.e. being occupied by the full set of naturally occurring, proteinogenic amino acid residues. More preferably, such positions may be partially randomized, i.e. being occupied by a subset of the full set of naturally occurring amino acid residues. Subsets of amino acid residues may be sets of amino acid residues with common physicochemical properties, such as sets of hydrophobic, hydrophilic, acidic, basic, aromatic, or aliphatic amino acids, subsets comprising all except for certain non-desired amino acid residues, such as sets not comprising cysteines or prolines, or subsets comprising all amino acid residues found at the corresponding position in naturally occurring repeat proteins. The randomization may be applied to some, preferably to all of the target interaction residues. Methods for making "randomized" repeat proteins such as by using oligonucleotide-directed mutagenesis of the nucleic acid sequences encoding said repeat proteins (e.g. by using mixtures of mononucleotides or trinucleotides), or by using error-prone PCR during synthesis of said nucleic acid sequences, are well known to the practitioner skilled in the art. Further preferred, at least one of said positions corresponds to a target interaction position.

The term "target molecule" refers to an individual molecule such as a nucleic acid molecule, a (poly)peptide or protein, a carbohydrate, or any other naturally occurring molecule, including any part of such individual molecule, or complexes of two or more of such molecules. The target may be a whole cell or a tissue sample, or it may be any non-natural molecule or moiety. Preferably, the target molecule is a naturally occurring or non-natural (poly)peptide or a (poly)peptide containing chemical modifications, for example modified by natural or non-natural phosphorylation, acetylation, or methylation.

The term "consensus sequence" refers to an amino acid sequence, wherein said consensus sequence is obtained by structural and/or sequence aligning of multiple repeat units. Using two or more structural and/or sequence aligned repeat units, and allowing for gaps in the alignment, it is possible to determine the most frequent amino acid residue at each position. The consensus sequence is that sequence which comprises the amino acids which are most frequently represented at each position. In the event that two or more amino acids are represented above-average at a single position, the consensus sequence may include a subset of those amino acids. Said two or more repeat units may be taken from the repeat units comprised in a single repeat protein, or from two or more different repeat proteins.

Consensus sequences and methods to determine them are well known to the person skilled in the art.

A "consensus amino acid residue" is the amino acid found at a certain position in a consensus sequence. If two or more, e.g. three, four or five, amino acid residues are found with a similar probability in said two or more repeat units, the consensus amino acid may be one of the most frequently found amino acids or a combination of said two or more amino acid residues.

The term "a repeat module derived from a consensus sequence of armadillo repeat units" refers to a repeat module obtainable by (i) a process comprising the steps of:
  (a) determining a consensus sequence of armadillo repeat units;
  (b) determining an initial armadillo repeat sequence motif, wherein the framework residues of said sequence motif are set to the most conserved consensus amino acid of the consensus sequence of (a) and wherein the positions of the target interaction residues of said sequence motif correspond to less conserved positions of the consensus sequence of (b);
  (c) refining the repeat sequence motif of (b) by computational design, sequence analysis and/or structural analysis of said repeat units; and
  (d) constructing a repeat module according to the repeat sequence motif of (c);

or (ii) a process comprising the process of (i) followed by further refining of the repeat module by computational design and/or evolution by random mutagenesis or random chimeragenesis.

However, the term "a repeat module derived from a consensus sequence of armadillo repeat units" is not restricted to repeat modules obtained by the described process. Based on the information provided in the description of the present invention it is now possible to design further repeat modules de novo without repeating the particular process described, and it is understood that the term "a repeat module derived from a consensus sequence of armadillo repeat units" also includes such modules designed de novo using the information provided herein, and modules designed de novo, then synthesized and further refined by computational design and/or evolution of the designed repeat module by random mutagenesis and/or random chimaragenesis.

The term "polypeptide in an extended conformation" means a consecutive stretch of amino acids that is in a conformation having no secondary structure elements. Preferably, the phi and psi angles of the peptide bonds of said stretch of amino acids are above 120°. Even more preferably, said angles are above 140°, 160° or 170°.

A preferred embodiment is a collection of armadillo repeat proteins comprising repeat modules with the armadillo repeat sequence motif

```
1         10              20(22)          30(38)
pxpxxaaxxx ±G±aaPxLapLL x±±±pxx±±±xxaxxx

          40(48)                42(70)
AaxxLxNaxx ±±±±±±±±±±±±±±±±±±±xx
```

wherein "x" denotes any amino acid, "±" denotes any amino acid or a deletion ("±" is not counted in the normal numbering of the positions, but included in the position numbers in parentheses), "a" denotes an amino acid with an apolar side chain, in particular any of the residues A, F, G, I, L, M, P, T, V, W and Y, and "p" denotes a residue with a polar side chain, in particular any of the residues A, C, D, E, G, H, K, N, P, Q, R, S, T and Y.

A further preferred embodiment is a collection of armadillo repeat proteins, wherein said repeat proteins comprise repeat modules with the armadillo repeat sequence motif

```
1         10         20         30         40 42
pxpxxaaxxx GaaPxLapLL xpxxxxaxxx AaxxLxNaxx xx
```

wherein "x" denotes any amino acid, "a" denotes an amino acid with an apolar side chain, and "p" denotes a residue with a polar side chain.

A further preferred embodiment is a collection of armadillo repeat proteins, wherein all of said repeat modules of a repeat domain are derived from consensus sequences of repeat units of a certain subfamily of armadillo repeat proteins. Preferably, said subfamily of armadillo repeat proteins are either the beta-catenin, plakoglobin, or importin alpha subfamilies.

In a further preferred embodiment, each of said repeat modules has an amino acid sequence, wherein at least 70% of the amino acid residues correspond either (i) to consensus amino acid residues deduced from the amino acid residues found at the corresponding positions of at least two repeat units; or (ii) to the amino acid residues found at the corresponding positions in one repeat unit. Preferably, such a repeat unit is a naturally occurring armadillo repeat unit.

Particularly preferred is a collection, wherein each of said repeat modules comprises the sequence motif

```
1         10         20         30         40 42
NxQxQaVIpx GaaPxLapLL xpxDxxaxxx AaxALxNIxx xx
```

wherein "x" denotes any amino acid, "a" denotes any of the residues A, F, G, I, L, M, P, T, V, W and Y, and "p" denotes any of the residues A, C, D, E, G, H, K, N, P, Q, R, S, T and Y.

Even more preferred is the collection, wherein each of said repeat modules comprises the sequence motif

```
1         10         20         30         40 42
NEQ1QAVIDA GALPVLVELL SSPDN2IQ22 AL2AL2NIT2 2G
```

wherein "1" and "2" represent any amino acid residue. This repeat sequence motif is called type I. The full consensus sequence type I is shown in SEQ ID NO:1 and Table 3. In Example 2 hereinafter, it is explained in detail how a consensus sequence was derived from 133 repeat sequences from armadillo repeat proteins of the importin-α subfamily (hence type I), then modifications applied based on an analysis of importin-α crystal structures, the structural implications resulting from this, the deduced positions of framework residues and of target interaction residues, and the intended use of the I type module. Preferably, "1" represents an amino acid residue selected from the group consisting of E, H, I, K, Q, R and T, and "2" represents an amino acid residue selected from the group consisting of A, D, E, F, H, I, K, L, M, N, Q, R, S, T, V, W and Y.

Also particularly preferred is a collection, wherein each of said repeat modules comprises the sequence motif

```
1         10         20         30         40 42
ExNxaAIxxx GgaPxLVpLL xpxxxxaaxx AaxxLxNLxx xx
```

wherein "x" denotes any amino acid, "a" denotes any of the residues A, F, G, I, L, M, P, T, V, W and Y, and "p" denotes any of the residues A, C, D, E, G, H, K, N, P, Q, R, S, T and Y.

Even more preferred is a collection, wherein each of said repeat modules comprises the sequence motif

```
1         10         20         30         40 42
EAN1LAIRES GGIPALVRLL SSNNE2IL22 AT2TL2NLA2 2G
```

wherein "1" and "2" represent any amino acid residue. This repeat sequence motif is called type T. The full consensus sequence type T is shown in SEQ ID NO:2 and Table 3. In Example 3 hereinafter, it is explained in detail how a consensus sequence was derived from 110 repeat sequences from armadillo repeat proteins of the β-catenin/plakoglobin subfamily (type T), then modifications applied based on analysis of a β-catenin crystal structures, the structural implications resulting from this, the deduced positions of framework residues and of target interaction residues, and the intended use of the T type module. Preferably, "1" represents an amino acid residue selected from the group consisting of E, H, I, K, Q, R and T, and "2" represents an amino acid residue selected from the group consisting of A, D, E, F, H, I, K, L, M, N, Q, R, S, T, V, W and Y.

Also particularly preferred is a collection, wherein each of said repeat modules comprises the sequence motif

```
1         10         20         30         40 42
NxQxxaVxpx GaaPxLVpLL xpxpxxaxxx AaxALxNaxx xx
```

wherein "x" denotes any amino acid, "a" denotes any of the residues A, F, G, I, L, M, P, T, V, W and Y, and "p" denotes any of the residues A, C, D, E, G, H, K, N, P, Q, R, S, T and Y.

Even more preferred is a collection, wherein each of said repeat modules comprises the sequence motif

```
1         10         20         30         40 42
NEQ1QAVIDA GGLPALVQLL SSPNE2IL22 AA2AL2NLA2 2G
```

wherein "1" and "2" represent any amino acid residue. This repeat sequence motif is called type C. The full consensus sequence type C is shown in SEQ ID NO:3 and Table 3. In Example 1 hereinafter, it is explained in detail how a consensus sequence was derived from 243 repeat sequences from armadillo repeat proteins of the importin-α and β-catenin/plakoglobin subfamilies (type C), then modifications applied based on an analysis of available crystal structures of importin-α and β-catenin and the analysis of complexes with target peptides, the structural implications resulting from this, the deduced positions of framework residues and of target interaction residues, and the intended use of the C type module. Preferably, "1" represents an amino acid residue selected from the group consisting of E, H, I, K, Q, R and T, and "2" represents an amino acid residue selected from the group consisting of A, D, E, F, H, I, K, L, M, N, Q, R, S, T, V, W and Y.

Also particularly preferred is a collection, wherein each of said repeat modules comprises the sequence motif

```
1         10         20         30          40 42
NEQxQAhIDA GshPALVQLL SSPNExhhxx AhxALxNhAx xx
```

wherein "x" denotes any amino acid, "s" represents an amino acid residue selected from the group consisting of A, I, L, V and G, and "h" represents an amino acid residue selected from the group consisting of A, I, L and V.

Even more preferred is a collection, wherein each of said repeat modules comprises the sequence motif

```
1         10         20         30          40 42
NEQ1QAVIDA GALPALVQLL SSPNE2IL22 AL2AL2NIA2 2G
```

wherein "1" and "2" represent any amino acid residue. This repeat sequence motif is called type M. The full consensus sequence type M is shown in SEQ ID NO:4 and Table 3. In Example 4 hereinafter, it is explained in detail how the type C module was further developed by computational methods using a "rotamer sampling" approach with the intention to create a module of type M with an improved hydrophobic core. Preferably, "1" represents an amino acid residue selected from the group consisting of E, H, I, K, Q, R and T, and "2" represents an amino acid residue selected from the group consisting of A, D, E, F, H, I, K, L, M, N, Q, R, S, T, V, W and Y.

Even more preferably, the amino acids at position 26 and 29 are either K or Q. Most preferably, the amino acid at position 29 is Q.

In a further preferred embodiment of a collection according to the present invention, one or more of the amino acid residues in a repeat module as described above are exchanged by an amino acid residue found at the corresponding position in an armadillo repeat unit. Preferably, up to 30% of the amino acid residues are exchanged, more preferably, up to 20%, and even more preferably, up to 10% of the amino acid residues are exchanged. Most preferably, such an armadillo repeat unit is a naturally occurring armadillo repeat unit.

In still another particular embodiment, up to 30% of the amino acid residues, more preferably, up to 20%, and even more preferably, up to 10% of the amino acid residues are exchanged with amino acids which are not found in the corresponding positions of armadillo repeat units.

The term "type of repeat module" refers to the characteristics of a module determined by the length of the module, the number and composition of its "fixed positions" as well as of its "randomized positions". "Different types of modules" may differ in one or more of said characteristics. Different "types" derive from repeat units comprising the same structural motif, but said types differ in framework positions. A type can be generated by:

(a) random mutagenesis or random chimeragenesis from an existing module or type;
(b) selecting a different sequence set for sequence alignment, including subfamilies;
(c) modifying an existing module or type by rational design; and/or
(d) modifying an existing module or type by a computational method.

Particularly preferred is a collection of armadillo repeat proteins comprising repeat domains consisting of either one of the four types of repeat modules named type I, type T, type C and type M defined above. Further preferred is a collection, wherein the amino acid sequences of the repeat modules comprised in said repeat domains are identical for each of the mentioned type except for the randomized residues.

In a still further preferred embodiment of the collection of the present invention, each of the repeat domains further comprises an N- and/or a C-terminal capping module having an amino acid sequence different from any one of said repeat modules. Preferably, said N-terminal capping module is followed by a non-library repeat module and/or said C-terminal capping module is preceded by a non-library repeat module.

The term "non-library repeat module" refers to a repeat module that is not a library repeat module. A non-library repeat module comprises only fixed positions. Preferably, non-library repeat modules increase the thermodynamic stability of said repeat domains.

The term "library repeat module" refers to a single repeat module obtained or selected from a repeat module library. The term "repeat module library" refers to a library of repeat modules produced according the invention.

The term "capping module" refers to a polypeptide fused to the N- or C-terminal repeat module of a repeat domain, wherein said capping module forms tight tertiary interactions with the repeat module, thereby providing a cap that shields the hydrophobic core of the repeat module at the side not in contact with the consecutive repeat module from the solvent. The N- and/or C-terminal capping module may be, or may be derived from, a capping unit (FIG. 1) or other domain found in a naturally occurring repeat protein adjacent to a repeat unit. The term "capping unit" refers to a naturally occurring folded (poly)peptide, wherein the (poly)peptide defines a particular structural unit which is N- or C-terminally fused to a repeat unit, and wherein the (poly)peptide forms tight tertiary interactions with the repeat unit thereby providing a cap that shields the hydrophobic core of said repeat unit at one side from the solvent. Such capping units may have sequence similarities to a repeat sequence motif. In Example 1 hereinafter, it is explained in detail how capping sequences may be derived from natural capping repeats of armadillo repeat proteins and adapted to their intended use in designed repeat proteins of the invention, taking into account information from crystal structures and target protein binding complexes. Another approach uses the type C module as a starting point, substituting the exposed hydrophobic residues with hydrophilic ones based on the natural sequences and on models derived from the crystal structures.

Preferably, each of the N- and/or C-terminal capping modules has an amino acid sequence, wherein at least 50%, preferably at least 60%, even more preferably at least 70% of the amino acid residues correspond either (i) to consensus amino acid residues deduced from the amino acid residues found at the corresponding positions of at least two repeat units or capping units; or
(ii) to the amino acid residues found at the corresponding positions in one repeat unit or capping unit. More preferably, such repeat units or capping units are naturally occurring repeat units or capping units.

In a preferred embodiment, the N-terminal capping module comprises the sequence motif

```
1         10          20          30 32
ELPQMTQQLN SDDMQEQLSA TVKFRQILSR DG
```

This repeat N-terminal capping module sequence motif is called Ny (SEQ ID NO:5). The N-terminal capping module Ny is derived from the N-terminal capping unit of importin-α of *S. cerevisiae* (UniProt entry IMA1_YEAST, residues 88-119) with the modification of the last two residues for connection to the adjacent repeat module.

A second preferred embodiment for the N-terminal capping module comprises the sequence motif

```
1         10          20          30
SLNELVKQLN SDDQKQLKEA AQKLRQLASD G
```

This repeat N-terminal capping module sequence motif is called Na (SEQ ID NO:6). The N-terminal capping module Na is derived from the type C repeat module of the present invention, by replacement of the hydrophobic residues otherwise exposed to the solvent if the type C repeat module is placed at the N-terminal of the armadillo repeat domain. A detailed description is provided in Example 1.

A preferred embodiment for the C-terminal capping module comprises the sequence motif

```
1         10          20          30          40
NEQKQAVKEA GALEKLEQLQ SHENEKIQKE AQEALEKQFS H
```

This repeat C-terminal capping module sequence motif is called Ca (SEQ ID NO:7). The C-terminal capping module Ca is derived from the type C repeat module of the present invention, by replacement of the hydrophobic residues otherwise exposed to the solvent if the type C repeat module is placed at the C-terminal of a repeat domain. A detailed description is provided in Example 1.

A second preferred embodiment for the C-terminal capping module comprises the sequence motif

```
1         10          20          30          40  43
DNINENADFI EKAGGMEKIF NCQQNENDKI YEKAYKIIET YFG
```

This repeat C-terminal capping module sequence motif is called Cy (SEQ ID NO:8). The C-terminal capping module Cy is derived from the C-terminal capping unit of importin-α of *S. cerevisiae* (UniProt entry IMA1_YEAST, residues 468-510) with the modification of the first residues for connection to the adjacent repeat module.

A third preferred embodiment for the C-terminal capping module comprises the sequence motif

```
1         10          20          30          40
NENADFIEKA GGMEKIFNAQ QNENDKIYEK AYKIIETYFG
```

This repeat C-terminal capping module sequence motif is called Cm (SEQ ID NO:9). The C-terminal capping module Cm is derived from the C-terminal capping module Cy by replacement of a cysteine by an alanine and removal of the first three amino acids.

In a further preferred embodiment of a collection according to the present invention, one or more of the amino acid residues in a repeat module as described above are exchanged by an amino acid residue found at the corresponding position in an armadillo repeat unit. Preferably, up to 30% of the amino acid residues are exchanged, more preferably, up to 20%, and even more preferably, up to 10% of the amino acid residues are exchanged. Most preferably, such a repeat unit or capping unit is a naturally occurring armadillo repeat unit or capping unit. In still another particular embodiment, up to 30% of the amino acid residues, more preferably, up to 20%, and even more preferably, up to 10% of the amino acid residues are exchanged with amino acids which are not found in the corresponding positions of armadillo repeat units or capping units.

The present invention further relates to a collection of nucleic acid molecules encoding the collection of designed repeat proteins described in this invention, of corresponding repeat domains or part of the repeat domains of said repeat proteins, or of corresponding single repeat modules and capping modules. In particular, a collection of nucleic acid molecules encoding the collection of designed repeat proteins as described above is considered.

The term "nucleic acid molecule" refers to a polynucleotide molecule, which is a ribonucleic acid (RNA) or deoxyribonucleic acid (DNA) molecule, either single stranded or double stranded. A nucleic acid molecule may either be present in isolated form, or be comprised in recombinant nucleic acid molecules or vectors.

A collection of nucleic acid molecules encoding a collection of armadillo repeat proteins as described above may be obtained by standard methods of the art back-translating the peptide sequences into DNA sequences, and optimizing the codon usage for the intended host cell for expression, e.g. optimizing for expression in *E. coli*. At the stage of DNA sequences, repeat and capping modules as described above may be easily combined, rearranged or further manipulated to give DNA sequences encoding the desired repeat proteins. Exemplification of the procedures can be found hereinafter in Example 1.

In a further embodiment, the present invention relates to a designed armadillo repeat protein or a corresponding repeat domain of the collection of armadillo repeat proteins described in this invention. In particular, a designed armadillo repeat protein of the collection of armadillo repeat proteins described above is considered.

Preferably, such a designed armadillo repeat protein or repeat domain has a predetermined property.

In the context of the present invention the term "predetermined property" refers to a property, which one of the repeat proteins out of the collection of repeat proteins should have, and which forms the basis for screening and/or selecting the collection. Such properties comprise properties such as binding to a target, blocking of a target, activation of a target-mediated reaction, enzymatic activity, and further properties, which are known to one of ordinary skill. Depending on the type of desired property, one of ordinary skill will be able to identify format and necessary steps for performing screening and/or selection. Preferably, said predetermined property is binding to a target.

More preferably, such a designed armadillo repeat protein or repeat domain is able to bind a target molecule meaning that said designed repeat protein has a detectable affinity to a given ligand.

Further preferably, such a designed armadillo repeat protein or repeat domain is a non-naturally occurring armadillo repeat protein or a non-naturally occurring repeat domain.

The term "non-naturally occurring" means synthetic or not from nature, more specifically, the term means made from the hand of man. The term "non-naturally occurring repeat protein" or "non-naturally occurring repeat domain" means that said repeat protein or said repeat domain is synthetic and not from nature. "Non-naturally occurring repeat protein" or "non-naturally occurring repeat domain" is a man-made protein or domain, respectively, obtained by expression of correspondingly designed nucleic acids. Preferably, the expression is done in eukaryotic or bacterial cells, or by using a cell-free in vitro expression system. Further, the term means that the sequence of said repeat protein or said repeat domain is not present as a non-artificial sequence entry in a sequence database, for example in GenBank, Embl-Bank or Swissprot. These databases and other similar sequence databases are well known to the person skilled in the art.

Further, a pharmaceutical composition comprising one or more of the above mentioned designed armadillo repeat proteins or corresponding repeat domains and optionally a pharmaceutical acceptable carrier and/or diluent is considered. Pharmaceutical acceptable carriers and/or diluents are known to the person skilled in the art. Even further, a diagnostic composition comprising one or more of the above mentioned designed armadillo repeat proteins or corresponding repeat domains is considered.

In a further embodiment, the invention relates to nucleic acid molecules encoding the particular designed armadillo repeat proteins.

In a further embodiment, the invention relates to a method for obtaining a designed armadillo repeat protein according to the present invention able to bind a target molecule, comprising the steps of (a) providing a collection of nucleic acid molecules encoding a collection of designed armadillo repeat proteins according to the invention;
(b) expressing the collection of step (a) to provide a collection of designed armadillo repeat proteins; and
(c) screening said collection of designed armadillo repeat proteins and/or selecting from said collection of designed armadillo repeat proteins to obtain at least one designed armadillo repeat protein able to bind said target molecule.

Example 5 and 6 hereinafter describes how libraries (collections) of nucleic acids encoding a collection of designed armadillo repeat proteins according to the invention can be obtained, and how they may be used for screening and selection.

The collection of designed armadillo repeat proteins according to the invention may be expressed by several methods in accordance with the screening and/or selection system being used, and may comprise the use of methods such as display on the surface of bacteriophages (WO 90/02809) or bacterial cells (WO 93/10214), ribosomal display (WO 98/48008), display on plasmids (WO 93/08278) or by using covalent RNA-repeat protein hybrid constructs (WO 00/32823), or intracellular expression and selection/screening such as by protein complementation assay (WO 98/341120). In all these methods, the designed armadillo repeat proteins of the invention are provided by expression of a corresponding collection of nucleic acid molecules and subsequent screening of the designed armadillo repeat proteins followed by identification of one or more designed armadillo repeat proteins having the ability to bind the target molecule via the genetic information connected to the designed armadillo repeat proteins.

In a preferred embodiment, the target molecule is a naturally occurring or a non-natural (poly)peptide or a (poly) peptide containing chemical modifications, for example modified by natural or non-natural phosphorylation, acetylation, or methylation.

In a further preferred embodiment, the present invention relates to a method for obtaining a designed armadillo repeat protein according to the present invention able to bind a target (poly)peptide. Said designed armadillo repeat protein provides a general binding mode that is in principle the same for every small part of the target (poly)peptide, allowing a modular recognition of a peptide in an extended conformation. The method allows to generate a series of modules recognizing the parts of the target (poly)peptide and to combine such modules without performing additional selections. The method comprises the steps of (a) deducing or obtaining the nucleic acid sequences corresponding to single repeat modules responsible for binding parts of the target (poly)peptide;
(b) constructing nucleic acid molecules encoding designed armadillo repeat proteins of the invention and comprising the nucleic acid sequences derived in step (a);
(c) expressing designed armadillo repeat proteins from the nucleic acid molecules derived in step (b); and
(d) screening said designed armadillo repeat proteins and/or selecting from said designed armadillo repeat proteins to obtain at least one designed armadillo repeat protein able to bind said target (poly)peptide.

The term "parts of the target (poly)peptide" refers to, but it is not limited to, amino acid sequences such as dipeptides, tripeptides or tetrapeptides belonging to the target (poly) peptide amino acid sequence. Preferably these parts of the target (poly)peptide are contiguous. The term "contiguous" refers to amino acid sequences which are not separated by other amino acids in the primary sequence of the (poly)peptide.

Most preferably the target (poly)peptide or the part of the target (poly)peptide is not involved in the formation of a secondary structure element.

A detailed description on how this method can be carried out is provided in Example 7 and in FIGS. 9 and 10. The technical details about generation and combination of repeat modules, capping repeat modules and repeat domains are described in patent application WO 02/20565 and in the Examples of the present invention and/or are known to the person skilled in the art.

In particular the invention relates to a method for obtaining an armadillo repeat domain able to bind a target (poly)peptide in its extended conformation without performing selections. This method makes use of the fact that particular repeat modules can be obtained by selection that have a high binding propensity to particular parts of a target (poly)peptide, e.g. to small stretches of amino acids such as particular dipeptides, tripeptides or tetrapeptides, formed from natural amino acids or from mixtures of natural and non-natural or modified natural amino acids. Modified amino acids are e.g. phosphorylated, acetylated or methylated amino acids. According to the inventive method the repeat domain is assembled from predetermined repeat modules having a high binding propensity to particular parts of a target (poly)peptide, such as small linear stretches of amino acids comprised in said target polypeptide in contiguous arrangement.

The method for obtaining said particular repeat module having defined binding specificity for a small linear stretch of amino acids comprises the steps of (a) deducing or obtaining a designed armadillo repeat protein comprising multiple internal repeat modules;
(b) generating a designed armadillo repeat protein library by replacing an internal repeat module of said designed armadillo repeat protein by a repeat module library;
(c) selecting a designed armadillo repeat protein from said armadillo repeat protein library according to binding ability to a target polypeptide comprising said small linear stretch of amino acids; and
(d) isolating the selected repeat module from said selected designed armadillo repeat protein from step (c) having specificity for said stretch of amino acids.

"Multiple" as used in "multiple internal repeat module" means three or more, in particular three, four or five. Preferably, the designed armadillo repeat protein of step (a) comprises three internal repeat modules. Even more preferably, the designed armadillo repeat protein of step (a) comprises three internal repeat modules, wherein the central internal repeat module is replaced by a repeat module library in step (b).

A repeat module library is obtained by standard methods known in the art. Preferably, the repeat module is a module containing the I, T, C or M sequence motifs described hereinbefore wherein positions "1" and "2" are fully randomized, i.e. representing any amino acid, or wherein "1" represents an amino acid residue selected from the group consisting of E, H, I, K, Q, R and T, and "2" represents an amino acid residue selected from the group consisting of A, D, E, F, H, I, K, L, M, N, Q, R, S, T, V, W and Y.

The invention is not restricted to the particular embodiments described in the Examples. Other sources may be used and processed following the general outline described below. For example database "PubMed" may be utilized which is available on the Internet. Particularly, information concerning the disclosed consensus sequences for armadillo repeat units can be found in Riggleman B. et al., Genes Dev 3:96-113, 1989; Peifer M. et al., Cell 76:789-91, 1994; Andrade M. A. et al., J Mol Biol 309:1-18, 2001; and SMART (Schultz J. et al., Proc Natl Acad Sci USA 95:5857-64, 1998; Letunic I. et al., Nucleic Acid Res 34:D257-60, 2006; http://smart.embl-heidelberg.de). A summary of the published sequence and the differences introduced by the present invention is presented in Table 1.

TABLE 1

Armadillo repeat consensus sequences

| Source | Consensus sequence [a, b] |
|---|---|
| Riggleman et al. | ..NKAI....GGIPALVRLL.N.D...LL.AA.VLH.LS... |
| | SELA VQE K R N AT T R A |
| | S S V |
| Peifer et aL | ..N+.ALL..GGLPALV+LL.S.+E..L..AA.AL+NLS.+. |
| | II I - I A |
| | VV V V |
| Andrade et al. | ...... L...G.LP.LV.LL ...... L...A...L.NL.. |
| | I I I I |
| | V V V |
| SMART (Schultz et al., Letunic et al.) | s+sppsLL+sGsLstLLpLLsss+s+LppsAstALsNLAs.s |
| | - II- I I - -I IG |
| | VV V V V VS |
| Present invention [c] | I NEQIQAVIDAGALPVLVELLSSPDNKIQKEALWALSNITSGG |
| | T EANKLAIRESGGIPALVRLLSSNNEKILEAATGILHNLALHG |
| | C NEQIQAVIDAGGLPALVQLLSSPNEKILKEAAWALSNLASGG |
| | M NEQIQAVIDAG**A**LPALVQLLSSPNEKILKEA**L**WALSN**I**ASGG |

[a] consensus sequences reported have been adapted to help visualization
[b] legend of the symbols used:

| Class of residue | | Key Residues |
|---|---|---|
| negative | - | D, E |
| polar | p | C, D, E, H, K, N, Q, R, S, T |
| positive | + | H, K, R |
| small | s | A, C, D, G, N, P, S, T, V |
| turnlike | t | A, C, D, E, G, H, K, N, Q, R, S, T |

[c] I (SEQ ID NO: 1), T (SEQ ID NO: 2), C (SEQ ID NO: 3) and M (SEQ ID NO: 4) refer to the module sequences subject of this invention. The underlined residues were not proposed in the previously published consensus sequences. The bold residues were introduced to stabilize the hydrophobic core of the type C consensus.

EXAMPLES

Materials

Chemicals were purchased from Fluka (Switzerland). Oligonucleotides were from Microsynth (Switzerland). A list of the oligonucleotides and their designation can be found in Table 2. Vent DNA polymerase, restriction enzymes and buffers were from New England Biolabs (USA) or Fermentas (Lithuania). The cloning and production strain was *E. coli* XL1-blue (Stratagene, USA).

TABLE 2

Oligonucleotides used for the assembly and cloning of designed and natural armadillo repeat protein genes

| name | sequence 5'-3' direction | SEQ ID NO | description (for = forward, rev = reverse) |
|---|---|---|---|
| AcatFOR | CGGGATCCACACGTGCAATTCCTG | 10 | for β catenin mouse |
| AcatREV | GCGGTACCATTAGTCCTCAGACATT CGG | 11 | rev β catenin mouse |
| IMAF5 | CGGGATCCCATCACTTCTGACATGA TTGAG | 12 | for importin α5 human |
| IMAR5 | GCGGTACCATTACCCGAAGTAATGC TCAATAAG | 13 | rev importin α5 human |
| pQE_f_1 | CGGATAACAATTTCACACAG | 14 | forward primer for pQE vectors |
| pQE_r_1 | GTTCTGAGGTCATTACTG | 15 | reverse primer for pQE vectors |
| Ny1F | CCAGGGATCCGAACTGCCGCAGATG ACCCAGCAGCTGAACTCTG | 16 | for assembly Ny repeat module library and amplification |
| Ny2R | CGGTAGCAGACAGCTGTTCCTGCAT GTCGTCAGAGTTCAGCTGCTGGG | 17 | rev assembly Ny repeat module library |
| Ny3F | GAACAGCTGTCTGCTACCGTTAAAT TCCGTCAGATCCTGTCTCGTGATGG | 18 | for assembly Ny repeat module library |
| Ny4R | TTCCTGGTACCCTAAGGTCTCAACC ATCACGAGACAGGATCTG | 19 | rev assembly Ny repeat module library and amplification |
| Na1F | CCAGGGATCCTCTCTGAACGAACTG GTTAAACAGCTGAACTCCG | 20 | for assembly Na repeat module library and amplification |
| Na2R | CTGAGCAGCTTCTTTCAGCTGTTTC TGGTCGTCGGAGTTCAGCTGTTTAA CCAG | 21 | rev assembly Na repeat module library |
| Na3F | CAGCTGAAAGAAGCTGAAAGAAGCT GCTCAGAAACTGCGTCAGCTGGCTT CCGATGG | 22 | for assembly Na repeat module library |
| Na4R | TTCCTGGTACCCTAAGGTCTCAACC ATCGGAAGCCAGCTG | 23 | rev assembly Na repeat module library and amplification |
| Cy1F | CCAGGGATCCTAGGAAGACCTTGGT GACAACATCAACG | 24 | for assembly Cy repeat module library and amplification |
| Cy2R | GCCACCAGCCTTCTCGATGAAGTCC GCGTTCTCGTTGATGTTGTCACCAA GG | 25 | rev assembly Cy repeat module library |
| Cy3F | CGAGAAGGCTGGTGGCATGGAGAAG ATCTTCAACTGCCAGCAGAACG | 26 | for assembly Cy repeat module library |
| Cy4R | GCTTTCTCGTAGATCTTGTCGTTCT CGTTCTGCTGGCAGTTG | 27 | rev assembly Cy repeat module library |
| Cy5F | CGACAAGATCTACGAGAAAGCTTAC AAGATCATCGAAACCTACTTCGGC | 28 | for assembly Cy and Cm repeat module libraries |
| Cy6R | TTCCTGGTACCTCATTAGCCGAAGT AGGTTTCGATG | 29 | rev assembly Cy and Cm repeat module libraries and amplification |
| CyM1F | CCAGGGATCCTAGGAAGACCTTGGT AACGAGAACGCGG | 30 | for assembly Cm repeat module library and amplification |

TABLE 2-continued

Oligonucleotides used for the assembly and cloning of designed and natural armadillo repeat protein genes

| name | sequence 5'-3' direction | SEQ ID NO | description (for = forward, rev = reverse) |
|---|---|---|---|
| CyM2R | GCCACCAGCCTTCTCGATGAAGTCC GCGTTCTCGTTACCAAGG | 31 | rev assembly Cm repeat module library |
| CyM3F | CGAGAAGGCTGGTGGCATGGAGAAG ATCTTCAACGCTCAGCAGAACG | 32 | for assembly Cm repeat module library |
| CyM4R | GCTTTCTCGTAGATCTTGTCGTTCT CGTTCTGCTGAGCGTTG | 33 | rev assembly Cm repeat module library |
| Ca1F | CCAGGGATCCTAGGAAGACCTTGGT AACGAACAGAAACAGGC | 34 | for assembly Ca repeat module library and amplification |
| Ca2R | GTTTCTCCAGAGCACCAGCTTCTTT AACAGCCTGTTTCTGTTCGTTACC | 35 | rev assembly Ca repeat module library |
| Ca3F | GCTGGTGCTCTGGAGAAACTGGAAC AGCTGCAGTCCCACGAG | 36 | for assembly Ca repeat module library |
| Ca4R | CCTGAGCTTCTTTCTGGATCTTCTC GTTCTCGTGGGACTGCAGC | 37 | rev assembly Ca repeat module library |
| Ca5F | GATCCAGAAAGAAGCTCAGGAAGCT CTGGAGAAGCAGTTCTCCC | 38 | for assembly Ca repeat module library |
| Ca6R | TTCCTGGTACCTCATTAGTGGGAGA ACTGCTTCTCCAG | 39 | rev assembly Ca repeat module library and amplification |
| imp1F | CCAGGGATCCTAGGAAGACCTTGGT AACGAACAGATCC | 40 | for assembly importin repeat module library and amplification |
| imp2R | ACCGGCAGAGCACCAGCGTCGATAA CAGCCTGGATCTGTTCGTTACCAAG G | 41 | rev assembly importin repeat module library |
| imp3F | CTGGTGCTCTGCCGGTTCTGGTTGA ACTGCTGTCCTCTCCGGAC | 42 | for assembly importin repeat module library |
| imp4R | CCACAGAGCTTCTTTCTGGATCTTG TTGTCCGGAGAGGACAGCAG | 43 | rev assembly importin repeat module library |
| imp5F | TCCAGAAAGAAGCTCTGTGGGCTCT GTCTAACATCACTTCTGGTGGTTGA GACC | 44 | for assembly importin repeat module library |
| imp6R | TTCCTGGTACCCTAAGGTCTCAACC ACCAGAAGTG | 45 | rev assembly importin repeat module library and amplification |
| cat1F | CCAGGGATCCTAGGAAGACCTTGGT GAAGC | 46 | for assembly catenin repeat module library and amplification |
| cat2R | CCACCAGATTCACGGATAGCCAGTT TGTTAGCTTCACCAAGGTCTTCC | 47 | rev assembly catenin repeat module library |
| cat3F | CTATCCGTGAATCTGGTGGTATCCC GGCTCTGGTTCGTCTGCTGTCCTC | 48 | for assembly catenin repeat module library |
| cat4R | TAGCAGCTTCCAGGATCTTCTCGTT GTTAGAGGACAGCAGACGAACC | 49 | rev assembly catenin repeat module library |
| cat5F | AAGATCCTGGAAGCTGCTACTGGCA CTCTGCACAACCTGGCTCTGCATGG TTGAG | 50 | for assembly catenin repeat module library |
| cat6R | TTCCTGGTACCCTAAGGTCTCAACC ATGCAGAGCC | 51 | rev assembly catenin repeat module library and amplification |
| cons1F | CCAGGGATCCTAGGAAGACCTTGGT AACGAACAAATCC | 52 | for assembly consensus repeat module and amplification |

TABLE 2-continued

Oligonucleotides used for the assembly and cloning of designed and natural armadillo repeat protein genes

| name | sequence 5'-3' direction | SEQ ID NO | description (for = forward, rev = reverse) |
|---|---|---|---|
| cons2R | AGCCGGCAGACCACCAGCATCGATA ACAGCTTGGATTTGTTCGTTACCAA GG | 53 | rev assembly consensus repeat module |
| cons3F | GGTGGTCTGCCGGCTCTGGTTCAAC TGCTGTCCTCTCCGAACG | 54 | for assembly consensus repeat module |
| cons4R | CCAAGCAGCTTCTTTCAGGATCTTC TCGTTCGGAGAGGACAGC | 55 | rev assembly consensus repeat module |
| cons5F | CCTGAAAGAAGCTGCTTGGGCTCTG TCTAACCTGGCTTCTGGTGGTTGAG | 56 | for assembly consensus repeat module |
| cons6R | TTCCTGGTACCCTAAGGTCTCAACC ACCAGAAGCCAG | 57 | rev assembly consensus repeat module and amplification |
| 2A-rev | AGCCGGCAGAGCACCAGCATCGATA ACAGCTTGGATTTGTTCGTTACCAA GG | 58 | rev hydrophobic core mutants assembly |
| 2AVrev | AGCCGGAACAGCACCAGCATCGATA ACAGCTTGGATTTGTTCGTTACCAA GG | 59 | rev hydrophobic core mutants assembly |
| 2AIrev | AGCCGGGATAGCACCAGCATCGATA ACAGCTTGGATTTGTTCGTTACCAA GG | 60 | rev hydrophobic core mutants assembly |
| 3A-for | GGTGCTCTGCCGGCTCTGGTTCAAC TGCTGTCCTCTCCGAACG | 61 | for hydrophobic core mutants assembly |
| 3AVfor | GGTGCTGTTCCGGCTCTGGTTCAAC TGCTGTCCTCTCCGAACG | 62 | for hydrophobic core mutants assembly |
| 3AIfor | GGTGCTATCCCGGCTCTGGTTCAAC TGCTGTCCTCTCCGAACG | 63 | for hydrophobic core mutants assembly |
| 4LLrev | CCACAGAGCTTCTTTCAGCAGCTTC TCGTTCGGAGAGGACAGC | 64 | rev hydrophobic core mutants assembly |
| 4LVrev | CCAAACAGCTTCTTTCAGCAGCTTC TCGTTCGGAGAGGACAGC | 65 | rev hydrophobic core mutants assembly |
| 4VLrev | CCACAGAGCTTCTTTCAGAACCTTC TCGTTCGGAGAGGACAGC | 66 | rev hydrophobic core mutants assembly |
| 4L-rev | CCAAGCAGCTTCTTTCAGCAGCTTC TCGTTCGGAGAGGACAGC | 67 | rev hydrophobic core mutants assembly |
| 4-Lrev | CCACAGAGCTTCTTTCAGGATCTTC TCGTTCGGAGAGGACAGC | 68 | rev hydrophobic core mutants assembly |
| 5L--for | CTGAAAGAAGCTCTGTGGGCTCTGT CTAACCTGGCTTCTGGTGGTTGAG | 69 | for hydrophobic core mutants assembly |
| 5V--for | CTGAAAGAAGCTGTTTGGGCTCTGT CTAACCTGGCTTCTGGTGGTTGAG | 70 | for hydrophobic core mutants assembly |
| 5-V-for | CTGAAAGAAGCTGCTTGGGTTCTGT CTAACCTGGCTTCTGGTGGTTGAG | 71 | for hydrophobic core mutants assembly |
| 5LV-for | CTGAAAGAAGCTCTGTGGGTTCTGT CTAACCTGGCTTCTGGTGGTTGAG | 72 | for hydrophobic core mutants assembly |
| 5VV-for | CTGAAAGAAGCTGTTTGGGTTCTGT CTAACCTGGCTTCTGGTGGTTGAG | 73 | for hydrophobic core mutants assembly |
| 5--Ifor | CTGAAAGAAGCTGCTTGGGCTCTGT CTAACATCGCTTCTGGTGGTTGAG | 74 | for hydrophobic core mutants assembly |

TABLE 2-continued

Oligonucleotides used for the assembly and cloning of designed and natural armadillo repeat protein genes

| name | sequence 5'-3' direction | SEQ ID NO | description (for = forward, rev = reverse) |
|---|---|---|---|
| 5L-Ifor | CTGAAAGAAGCTCTGTGGGCTCTGT CTAACATCGCTTCTGGTGGTTGAG | 75 | for hydrophobic core mutants assembly |
| 5LVIfor | CTGAAAGAAGCTGTTTGGGTTCTGT CTAACATCGCTTCTGGTGGTTGAG | 76 | for hydrophobic core mutants assembly |
| 6Irev | TTCCTGGTACCCTAAGGTCTCAACC ACCAGAAGCGAT | 77 | rev hydrophobic core mutants assembly and amplification |
| Ny4Rbis | TTCCTGGTACCCTAAGGTCTCATTC GTTACCATCACGAGACAGGATCTG | 78 | rev assembly Ny repeat module library |
| Ca1libF | CCAGGGATCCTCTAGATAGGAAGAC CTCGAACAGAAACAGGC | 79 | for assembly Ca repeat module library |
| Ca2libR | GTTTCTCCAGAGCACCAGCTTCTTT AACAGCCTGTTTCTGTTCGAGGTC | 80 | rev assembly Ca repeat module library |
| lib1F1 | CCAGGGATCCTAGGAAGACCTCGAA CAAAYCCAAGCTGTTATCG | 81 | for assembly L repeat module library |
| lib1F2 | CCAGGGATCCTAGGAAGACCTCGAA CAAVAACAAGCTGTTATCG | 82 | for assembly L repeat module library |
| lib1F3 | CCAGGGATCCTAGGAAGACCTCGAA CAACRCCAAGCTGTTATCG | 83 | for assembly L repeat module library |
| lib2R | CCAGAGCCGGCAGAGCACCAGCATC GATAACAGCTTG | 84 | rev assembly L repeat module library |
| lib3F | CTGCCGGCTCTGGTTCAACTGCTGT CCTCTC | 85 | for assembly L repeat module library |
| lib4R | TTTCAGGATCTTCTCGTTCGGAGAG GACAGCAG | 86 | rev assembly L repeat module library |
| lib5F | CGAGAAGATCCTGAAANNNGCTCTG NNNGCTCTGNNNAACATCGCTNNNNN NNGGTAACGAATGAG | 87 | for assembly L repeat module library; with trinucleotide phosphoramidites |
| lib6R | TTCCTGGTACCCTAAGGTCTCATTC GTTACC | 88 | rev assembly L repeat module library and amplification |
| libFOR | CCAGGGATCCTAGGAAGACCTCGAA C | 89 | for amplification L repeat module library |

Molecular Biology

Unless stated otherwise, methods are performed according to described protocols (Sambrook J., Fritsch E. F. and Maniatis T., Molecular Cloning: A Laboratory Manual, Cold Spring Harbor Laboratory 1989, New York).

Nomenclature

The nomenclature used to define the positions inside the repeat units and modules is based on the SMART family alignment (http://smart.embl-heidelberg.de) and is consistent with the numbering proposed by Andrade, M. A. et al., J Mol Biol 309:1-18, 2001 shifted by three positions. Thus starting position −2 in their work corresponds to position 1 in the present disclosure. The positions 1, 12, 25 are the putative beginning of H1, H2, H3. The repeat proteins have been named according to the modules that they contain: The name indicates, in this order, the type of N-terminal module (A for Artificial or Na, Y for Yeast-derived or Ny), the type of internal module (type I, T or C) with the number of modules used, the type of C-terminal module (A for Artificial or Ca, Y for Yeast-derived or Cy): e.g. $YI_4A$ contains a Yeast-derived N-terminal module (Ny), 4 internal modules of type I and an Artificial C-terminal module (Ca).

Sequencing and Mass Determination

All the DNA sequences were confirmed by sequencing and the calculated molecular weight of all described proteins was confirmed by mass spectrometry.

Protein Properties

The module sequences described in the examples are listed in Table 3. The specific positions described in the examples refer to the numbering adopted in Table 3. A summary of the experimentally determined biophysical properties of the proteins is presented in Table 4.

TABLE 3

| Designed module sequences | 1 5 10 15 20 25 |
|---|---|
| Ny | E L P Q M T Q Q L N S D D M |
| Na | S L N E L V K Q L N S D D Q |
| I type | N E Q I Q A V I D A G A L P V L V E L L S S P D N |
| T type | E A N K L A I R E S G G I P A L V R L L S S N N E |
| C type | N E Q I Q A V I D A G G L P A L V Q L L S S P N E |
| M type | N E Q I Q A V I D A G A L P A L V Q L L S S P N E |
| Cy | D N I N E N A D F I E K A G G M E K I F N C Q Q N E N D |
| Cm | N E N A D F I E K A G G M E K I F N A Q Q N E N D |
| Ca | N E Q K Q A V K E A G A L E K L E Q L Q S H E N E |

| | 30 35 40 |
|---|---|
| Ny | Q E Q L S A T V K F R Q I L S R D G |
| Na | K Q L K E A A Q K L R Q L A S D G |
| I type | K I Q K E A L W A L S N I T S G G |
| T type | K I L E A A T G T L H N L A L H G |
| C type | K I L K E A A W A L S N L A S G G |
| M type | K I L K E A L W A L S N I A S G G |
| Cy | K I Y E K A Y K I I E T Y F G |
| Cm | K I Y E K A Y K I I E T Y F G |
| Ca | K I Q K E A Q E A L E K Q F S H |

Ny (SEQ ID NO: 5) is an N-terminal capping repeat derived from importin-α from *S. cerevisiae*,
Na (SEQ ID NO: 6) is an artificial N-terminal capping repeat.
I type (SEQ ID NO: 1) is the internal module based on sequences from the importin-α subfamily,
T type (SEQ ID NO: 2) is the internal module based on sequences from the β-catenin/plakoglobin subfamily,
C type (SEQ ID NO: 3) is the overall consensus based on both subfamilies.
M type (SEQ ID NO: 4) is obtained from C type by computational methods using a "rotamer sampling" approach with the intention to create a module with an improved hydrophobic core.
Cy (SEQ ID NO: 8) is a C-terminal capping repeat derived from importin-α from *S. cerevisiae*,
Cm (SEQ ID NO: 9) is a modified version of Cy (lacking the first three residues and with Cys 19 replaced by Ala),
Ca (SEQ ID NO: 7) is the artificial C-terminal capping repeat.

TABLE 4

Biophysical properties of designed and natural armadillo repeat protein

| name | residues (repeats)[a] | pI[b] | $MW_{calc}$ (kDa)[b] | Oligomeric state[c] | $MW_{obs}$ (kDa)[d] | MW obs/calc[e] | $CD_{222}$ (MRE)[f] | Helical content[g] | Obs. Tm (° C.)[h] | ANS[i] (cps × $10^3$) |
|---|---|---|---|---|---|---|---|---|---|---|
| $YI_2A$ | 169 (4) | 5.2 | 18.6 | dimer | 64.6 | 1.7 | −13000 | 63% | ~55 | 113 |
| $YI_4A$ | 253 (6) | 4.8 | 27.4 | dimer | 116.1 | 2.1 | −19500 | 80% | ~69 | 116 |
| $YI_8A$ | 421 (10) | 4.6 | 44.9 | dimer | 148.8 | 1.7 | −22600 | 85% | >85 | 143 |
| $YT_2A$ | 169 (4) | 6.3 | 18.6 | dimer | 141.2 | 3.8 | −7100 | 23% | ~56 | 136 |
| $YT_4A$ | 253 (6) | 6.5 | 27.3 | dimer | 219.6 | 4.0 | −10100 | 40% | ~75 | 135 |
| $YT_8A$ | 421 (10) | 6.7 | 44.8 | dimer | 229.7 | 2.6 | −9400 | 35% | ~83 | 109 |
| $YC_2A$ | 169 (4) | 5.4 | 18.4 | mixt. | 59.1 | n.d. | −9100 | 45% | n.d. | 201 |
| $YC_4A$ | 253 (6) | 5.1 | 26.9 | mono | 50.0 | 1.9 | −12100 | 49% | n.d. | 639 |
| $YC_8A$ | 421 (10) | 4.8 | 44.0 | mono | 76.7 | 1.7 | −20000 | 62% | n.d. | 635 |
| αArm[j] | 435 (10) | 5.5 | 48.2 | mono | 42.9 | 0.9 | −14300 | 54% | ~43 | 67 |

TABLE 4-continued

| Biophysical properties of designed and natural armadillo repeat protein | | | | | | | | | | | |
|---|---|---|---|---|---|---|---|---|---|---|---|
| name | residues (repeats)[a] | pI[b] | $MW_{calc}$ (kDa)[b] | Oligomeric state[c] | $MW_{obs}$ (kDa)[d] | MW obs/calc[e] | $CD_{222}$ (MRE)[f] | Helical content[g] | Obs. Tm (° C.)[h] | ANS[i] (cps × $10^3$) |
| βArm[k] | 528 (12) | 8.7 | 57.6 | mono | 52.6 | 0.9 | −16800 | 60% | ~58 | 112 |
| $YM_4A$ | 253 (6) | 5.1 | 27.1 | mono | 32.2 | 1.2 | −18800 | 87% | ~70 | 143 |

[a]the number of residues includes the $MRGSHis_6$ tag; the number of repeats includes capping repeats
[b]pI and molecular weight calculated from the sequence; masses were confirmed by mass spectrometry
[c]Oligomeric state (Os) as indicated by multi-angle static light scattering
[d]observed molecular weight as determined in size exclusion chromatography
[e]ratio between observed and calculated molecular weight, taking into account the oligomeric state (Os): $MW_{obs/calc} = MW_{obs}/(Os \cdot MW_{calc})$
[f]mean residue ellipticity at 222 nm expressed as deg · $cm^2$/dmol
[g]helical content estimated with the program CDpro
[h]Tm observed in thermal denaturation by CD
[i]ANS maximum fluorescence intensity in counts per second (cps)
[j]armadillo domain of human importin-α5
[k]armadillo domain of mouse β-catenin
n.d. indicates that the value has not been determined due either to an inhomogeneous sample (oligomeric state of $YC_2A$) or lack of cooperative transition in thermal denaturation ($YC_2A$, $YC_4A$ and $YC_8A$)

Example 1

The example reports a consensus design strategy applied to generate designed armadillo repeat proteins based on a combination of sequences of importin-α and β-catenin / plakoglobin subfamilies. The design procedure was based on the generation of self-compatible modules. A consensus sequence (type C) was derived from multiple alignments of single armadillo repeat units from the SWISSProt database (www.expasy.ch). Two different versions of terminal capping modules were generated to protect the hydrophobic core from solvent exposure. The peptide sequences of all modules were reverse-translated to DNA sequence, optimizing the codon usage for expression in *E. coli*. Oligonucleotides were designed to allow assembly PCR of internal and capping modules. The resulting PCR products contained type IIs restriction enzymes recognition sites and were connected using the strategy introduced by Binz H.K. et al., J Mol Biol 332:489-503, 2003. The DNA molecules encoding the designed repeat proteins were inserted in a suitable expression vector. Proteins were expressed, purified and characterized by size exclusion chromatography, ANS binding, circular dichroism spectroscopy and denaturation experiments.

Consensus Design of Type C Internal Module

The initial sequence profile has been generated using the family alignment from SMART (data from Jan. 2004) as starting point. All sequences lacking annotation in the Swiss-Prot database were removed, being hypothetical proteins or sequences for which no protein data were available except indirect evidence by sequence homology. The final set of 319 sequences lead to a profile of 40 residues, covering the repeat sequence from H1 to H3, but excluding the loop between H3 and the next repeat unit. This sequence profile has been used for a further search against the Swiss-Prot database. The repeat units thus found belong to proteins that fall into different subfamilies of armadillo repeat proteins, as indicated by Andrade M. A. et al., supra.

Since β-catenin/plakoglobin and importin-α subfamilies are known to be peptide binders and have crystal structures available, members of these two subfamilies were selected to generate consensus sequences. The slight overrepresentation of importin-α sequences in the selected set (133 over 243) is a consequence of the higher number of importin-α proteins present in the database. No normalization was applied during the calculation of the combined consensus sequence. The automatic alignment, obtained with clustalW (Thompson J. D. et al., Nucleic Acid Res 22:4673-80, 1994), was manually refined including also the loop connecting adjacent repeat units. The consensus sequences were further improved taking into account information from the crystal structures to reduce possible steric clashes. Requirements for the cloning strategy were also considered at this stage, leading to modules type C (Tables 3 and 5).

TABLE 5

Overall consensus

| | 1 | | | | 5 | | | | | 10 | | | | | 15 | | | | | 20 | | |
|---|---|---|---|---|---|---|---|---|---|---|---|---|---|---|---|---|---|---|---|---|---|---|
| consensus | N | E | Q | I | Q | A | V | I | D | A | G | G | L | P | A | L | V | Q | L | L | S | S |
| rel. freq. | 17 | 22 | 34 | 27 | 25 | 32 | 45 | 29 | 17 | 28 | 58 | 27 | 32 | 50 | 27 | 63 | 58 | 18 | 65 | 80 | 19 | 30 |
| 2nd cons. | S | P | N | K | L | V | I | V | E | S | N | A | I | Q | R | F | I | R | T | M | T | H |
| rel. freq. | 16 | 17 | 20 | 19 | 10 | 12 | 27 | 21 | 16 | 25 | 13 | 18 | 30 | 15 | 12 | 21 | 12 | 17 | 7 | 10 | 10 | 15 |
| 3rd cons. | E | A | P | T | A | M | L | R | Q | Q | Q | V | V | S | V | I | C | K | I | I | Q | K |
| rel. freq. | 14 | 13 | 12 | 16 | 9 | 8 | 16 | 16 | 14 | 9 | 8 | 18 | 24 | 8 | 10 | 7 | 7 | 14 | 6 | 8 | 9 | 9 |
| consensus refinement | N | E | Q | I | Q | A | V | I | D | A | G | G | L | P | A | L | V | Q | L | L | S | S |
| binding | | | | x | | | | | | | | | | | | | | | | | | |
| type C | N | E | Q | I | Q | A | V | I | D | A | G | G | L | P | A | L | V | Q | L | L | S | S |

| | | | 25 | | | | | 30 | | | | | | 40 | | | | | | |
|---|---|---|---|---|---|---|---|---|---|---|---|---|---|---|---|---|---|---|---|---|
| consensus | P | D | E | K | I | L | K | E | A | A | W | A | L | S | N | L | A | S | G | N |
| rel. freq. | 21 | 36 | 27 | 22 | 35 | 24 | 21 | 23 | 62 | 24 | 44 | 47 | 69 | 28 | 70 | 53 | 32 | 17 | 43 | 22 |
| 2nd cons. | N | E | V | N | V | Q | E | V | T | L | G | T | I | G | I | I | T | D | D | G |
| rel. freq. | 16 | 9 | 10 | 16 | 27 | 23 | 17 | 12 | 20 | 20 | 21 | 21 | 19 | 16 | 8 | 37 | 28 | 12 | 16 | 20 |

TABLE 5-continued

| Overall consensus | | | | | | | | | | | | | | | | | | | | |
|---|---|---|---|---|---|---|---|---|---|---|---|---|---|---|---|---|---|---|---|---|
| 3rd cons. | D | S | P | S | L | V | F | P | C | V | R | V | V | H | Y | A | S | L | C | T |
| rel. freq. | 14 | 9 | 9 | 12 | 21 | 21 | 12 | 10 | 9 | 20 | 12 | 10 | 10 | 14 | 8 | 4 | 18 | 10 | 9 | 15 |
| consensus | P | D | E | K | I | L | K | E | A | A | W | A | L | S | N | L | A | S | G | N |
| refinement | | N | | | | | | | | | | | | | | | | | | G |
| binding | | | | x | | | x | x | | | x | | | x | N | | | x | x | |
| type C | P | N | E | K | I | L | K | E | A | A | W | A | L | S | N | L | A | S | G | G |

Consensus sequence derived from multiple sequence alignment and refinement to modules type C (SEQ ID NO: 3).
The numbers indicate the positions inside the single repeats according to the nomenclature introduced.
The most frequent, the second and the third most frequent residue are indicated, with the relative frequency (rel. freq) expressed as percentage.
Modifications introduced during the refinement and positions responsible for binding (indicated by x and the conserved N) are shown.
Consensus (SEQ OD NO: 111), 2nd cons. (SEQ ID NO: 112), and 3rd cons. (SEQ ID NO: 113) sequences are shown.

The putative helices H1, H2, H3 cover the residues 1-10, 12-21, 25-40, respectively. The positions 7, 16, 17, 19, 20, 31, 34, 35, 38 are well conserved in all the sequences and are part of the hydrophobic core of the armadillo proteins. Gln5 can potentially form a hydrogen bond with Asp9 of the same repeat unit, stabilizing H1 (observed in structure 1EE5, Conti E. and Kuriyan J., Structure Fold Des 8:329-38, 2000). Gly11 is conserved for its crucial role in bending the polypeptide chain between H1 and H2, being compatible with a positive $\phi$ angle required at this position. Pro14 is an unusual conserved feature of armadillo repeats, present at a frequency of 50% in the overall alignment. It is located at the beginning of H2, at a position where it is still not necessary to involve the backbone nitrogen in a hydrogen bond; instead of disrupting the secondary structure, it adopts the $\phi/\psi$ angles typical for $\alpha$ helices. Asn37 is a well conserved residue in all consensus sequences, due to its critical role in binding to the backbone of target peptides. Trp33 is also involved in binding, specifically in the recognition of target side chains in the case of importin-$\alpha$ proteins. Thus, it appears with high frequency in the importin subfamily and therefore it is present in the overall consensus sequence as well.

The positions potentially involved in binding of peptides (4, 26, 29, 30, 33, 36, 37, 40, 41) have been defined based on the analysis of structures of complexes (PDB IDs 1BK5, 1BK6, 1EE4, 1EE5, 1EJL, 1EJY, 1G3J, 1IQ1, 1JPP, 1LUJ, 2BCT, 3BCT, 1I7W, 1I7X, 1JPW, 1IAL, 1JDH, 1M1E, 1PJM, 1PJN, 1Q1S, 1Q1T, 1QZ7, 1UN0, 1TH1) and data from mutation experiments (von Kries J. P. et al., Nat Struct Biol 7:800-7, 2000; Leung S. W. et al., J Biol Chem 278: 41947-53, 2003; Hoffmans R. and Basler K., Development 131:4393-400, 2004). Besides binding to target peptides, position 4 contributes to the hydrophobic core formation as well, thus the types of residues allowed at this position in a potential library would probably be restricted, when taking into account this additional requirement.

Positions 24 and 25 at the joint between loop H2-H3 and H3 show a clear preference for acidic residues in all consensus sequences. However, a pair of negatively charged residues never occurs in the observed sequences, and it could lead to charge repulsion or formation of a negatively charged belt along the whole protein. A preferred position for the negative charge is not pronounced (Asp24 36%, Glu25 27% in type C), and the alternative amino acids have all very low frequency (<10%). The residues selected for replacement were then chosen to improve the H3 stability: Glu25 was kept due to its higher helical propensity and Asn24 was introduced to keep structural similarity to the more frequent residue Asp and to take advantage of its propensity as N-cap residue. Gly has been introduced at position 42 for cloning purposes. It is remarkable that, because of short H3-H1 loops (1-3 residues in general), very often one position of the loop is occupied by a Gly. Taking into account that position 41 is sometimes involved in binding and then possibly subjected to mutation for applications, it is important to keep a constant glycine inside the loop to maintain the required flexibility.

Design of Capping Modules

Specialized repeat units form the N- and C-terminal part of the armadillo domain in natural proteins. Capping repeat units are probably involved in the protection of the hydrophobic core, as they present a hydrophobic surface to the internal repeat unit side and a hydrophilic surface to the solvent. Capping repeat units have been considered in the designed LRR (Stumpp M. T. et al., J Mol Biol 332:471-87, 2003) and ankyrin repeat proteins (Binz H. K. et al., J Mol Biol 332: 489-503, 2003), and an additional helix has been included in the design of TPR proteins (Main E. R. et al., Structure (Camb) 11:497-508, 2003).

Boundaries of the armadillo domain have been estimated by limited proteolysis, but they are not clearly defined, also due to the weak similarity of the terminal repeat units to the internal ones. In addition, not all the residues are visible in the crystal structures of importin-$\alpha$ and $\beta$-catenin. It is likely that only the visible residues contribute to the armadillo domain, and the additional parts are unstructured and do not strictly belong to the domain. The N-terminal capping repeat unit has been defined as starting from H2, position 12. In contrast, the C-terminal capping repeat unit is completely visible in the structures and is defined from position 1 to position 41, including H1 to H3 (Table 3).

The capping modules have been designed by using two different approaches. In the first case natural capping repeat units were adapted to the designed internal repeat modules. Structural information to ensure compatibility between the capping repeat units and the designed internal repeat modules is a fundamental prerequisite for this approach. The importin-$\alpha$ from yeast *Saccharomyces cerevisiae* turned out to be the best candidate as general capping repeat units donor: All the designed repeat modules will present a flat surface which can interact with the inner surface of yeast importin-$\alpha$ capping repeat units, as observed in molecular models. The N-terminal capping repeat unit covers the residues from Glu88 to His119 of yeast importin-$\alpha$. However, the two residues Glu118-His119 were changed to Asp-Gly to adapt the terminal loop to the designed repeat modules: Glycine is used for assembly of the modules and aspartate keeps the negative charge which is frequently found in natural proteins, while reducing the helical propensity in the turn region.

The C-terminal capping repeat unit covers the region from Asn471 to Gly510 in yeast importin-$\alpha$. However, the loop connecting the last internal repeat unit with the C-terminal repeat unit contains additional residues, compared to other natural importins. A modified version of this C-terminal capping repeat unit has been then generated by introducing three residues (Asp-Asn-Ile) before H1. Asn and Ile are naturally present at these positions; Asp has been included to keep a negatively charged loop, as observed in several natural sequences, while reducing the helical propensity. The yeast importin-α derived N-terminal and C-terminal capping modules are named Ny and Cy, respectively. A second version of the C-terminal capping module, named Cm, was designed without the three initial residues and with Ala replacing Cys at position 19. The sequences of Ny, Cy and Clare indicated in Table 3.

In the second approach, two completely artificial capping modules were designed, starting from the type C module and substituting the exposed hydrophobic residues with hydrophilic ones, based on the natural sequences and on models derived from the crystal structures. The N-terminal capping repeat unit goes from position 12 to 42 and includes H2 and H3. Positions 7, 12, 19, 27, 34 are occupied by hydrophobic residues in the type C module and have to be replaced by hydrophilic residues based on structures and common residues obtained from alignment of N-terminal capping sequences. Ser12 provides the N-terminal helix cap of H2. Asn14 substitutes the more common proline providing a polar residue with a relatively short side chain. Glu15 can interact with Ser12 in α helix and can additionally stabilize it. Lys18 can form a salt bridge with Glu15, stabilizing the helix, and, in general, a long polar residue is required at this position. Gln19 provides a hydrophobic part for interaction with the neighboring internal repeat module as well as a polar moiety for solvent exposure. Asn21 is common at this position and it has a good propensity as helix C-capping residue. Asp23 and Asp24 are conserved as a charged couple in several N-terminal capping repeat units. Gln25 is well conserved, polar, with high helical propensity. Gln27 provides a hydrophobic part for interaction with the neighboring internal repeat module as well as a polar moiety for solvent exposure. Gln33, well conserved among capping repeat units, substitutes the Trp involved in binding. Lys34 is present at moderate frequency in N-terminal capping repeat units, among other polar residues. Arg36 has high frequency of occurrence and seems to be able to interact with Trp33 present in the type I and type C modules. Gln37 has a long side chain typical for residues at this position, and, instead of the more common lysine, avoids the formation of a positively charged spot in combination with Arg36. Asp41 maintains the negative charge often present in this position and breaks the helix. Gly42 was introduced to add flexibility and for further module assembly.

The C-terminal capping repeat unit includes all three helices. Positions 8, 13, 17, 20, 28, 32, 35, 38, 39 are occupied by hydrophobic residues in the type C module and had to be replaced by hydrophilic residues based on structures and common residues obtained from alignment of C-terminal capping sequences. Lys4 can potentially contribute to the hydrophobic core with the long aliphatic part of the side chain, while contacting the solvent with the positively charged amino group. Lys8 is present to avoid the formation of a cluster of negative charges that would be formed if a conserved glutamate was used at this position, while keeping a good helical propensity and a long side chain. Glu9 is a highly conserved residue. Ala12 can potentially interact with the hydrophobic core. Glu14 is a common polar residue with good helical propensity as substitute for proline. Lys15 also is a common polar residue with relatively good helical propensity. Leu13 occupies a former hydrophobic core position, but it was retained for its high helical propensity and its ability to interact with Phe39. Glu17 corresponds to a core position in an internal repeat unit; the hydrophobic residue was substituted with this frequently occurring hydrophilic amino acid with high helical propensity. Gln20 is the more frequent polar residue used to substitute the conserved leucine present in the internal repeat units. Positions from 21 to 23 are not clearly defined, showing strong conservation in the catenin/plakoglobin subfamily (may be for functional reasons) and higher degree of variability in importins. The most conserved residues form the importin subfamily have been then chosen to occupy these positions. Gln28 can provide hydrophobic interactions and a polar side chain, and represents a better choice compared to a conserved tyrosine in the importin subfamily, and an alanine in the catenin/plakoglobin subfamily. Gln32 provides good helical propensity and a polar side chain. The presence of frequent aromatic residues at this position does not seem to have a structural reason, judging from the crystal structures. Glu33 is one of the charged residues often found at this position and it has good helical propensity. Glu36 has high frequency in importins where this position is occupied by acidic residues, while in the catenin/plakoglobin subfamily phenylalanine and tyrosine are present. The aromatic residues have probably a functional role, but a charged residue constitutes the better choice, because of the exposed position. Lys37 was chosen to replace the conserved asparagine in the internal repeat units. Gln38 was chosen to replace hydrophobic residues, always present at this position both in internal and capping repeat units, while providing a polar moiety in contact with the solvent. Phe39 is conserved in several capping repeat units. From the available structures, it seems to be important for sealing of the hydrophobic core of importins and for compactness of C-terminal capping repeat unit via interaction with Leu13. His41 has been added as capping residue to stabilize H3. The designed N-terminal and C-terminal capping modules have been named Na and Ca, respectively, and are indicated in Table 3.

Synthesis of DNA Encoding the Designed Armadillo Repeat Proteins

The peptide sequences of all modules were back-translated to DNA sequence, optimizing the codon usage for expression in *E. coli*. Each module was synthesized starting from overlapping oligonucleotides. All single modules, at the DNA level, were assembled from oligonucleotides by assembly PCR (FIG. 4). The sequence of type C module is shown below with the restriction sites indicated; the overhangs after digestion with BsaI and BpII are underlined. The other internal modules differ in the positions corresponding to variations in the amino acid sequence. DNA sequences of Ny and Ca capping modules are also shown, as examples of N-terminal and C-terminal capping modules, respectively; the other capping modules differ in the positions corresponding to variations in the amino acid sequence.

```
DNA sequence of type C module (SEQ ID NO: 90) and
corresponding protein sequence (SEQ ID NO: 3)
         BamHI      BpiI
                                N  E  Q  I  Q  A  V  I  D  A  G  G
   1 CCAGGGATCCTAGGAAGACCTTGGTAACGAACAAATCCAAGCTGTTATCGATGCTGGTGG
     GGTCCCTAGGATCCTTCTGGAACCATTGCTTGTTTAGGTTCGACAATAGCTACGACCACC

       L  P  A  L  V  Q  L  L  S  S  P  N  E  K  I  L  K  E  A  A
  61 TCTGCCGGCTCTGGTTCAACTGCTGTCCTCTCCGAACGAGAAGATCCTGAAAGAAGCTGC
     AGACGGCCGAGACCAAGTTGACGACAGGAGAGGCTTGCTCTTCTAGGACTTTCTTCGACG

                                        BsaI     KpnI
       W  A  L  S  N  L  A  S  G  G
 121 TTGGGCTCTGTCTAACCTGGCTTCTGGTGGTTGAGACCTTAGGGTACCAGGAA
     AACCCGAGACAGATTGGACCGAAGACCACCAACTCTGGAATCCCATGGTCCTT

DNA sequence of Ny capping module (SEQ ID NO: 91) and
corresponding protein sequence (SEQ ID NO: 5)
         BamHI
                 E  L  P  Q  M  T  Q  Q  L  N  S  D  D  M  Q  E  Q
   1 CCAGGGATCCGAACTGCCGCAGATGACCCAGCAGCTGAACTCTGACGACATGCAGGAACA
     GGTCCCTAGGCTTGACGGCGTCTACTGGGTCGTCGACTTGAGACTGCTGTACGTCCTTGT

                                                    BsaI     KpnI
       L  S  A  T  V  K  F  R  Q  I  L  S  R  D  G
  61 GCTGTCTGCTACCGTTAAATTCCGTCAGATCCTGTCTCGTGATGGTTGAGACCTTAGGGT
     CGACAGACGATGGCAATTTAAGGCAGTCTAGGACAGAGCACTACCAACTCTGGAATCCCA

 121 ACCAGGAA
     TGGTCCTT

DNA sequence of Ca capping module (SEQ ID NO: 92) and
corresponding protein sequence (SEQ ID NO: 7)
         BamHI BpiI
                                N  E  Q  K  Q  A  V  K  E  A  G  A
   1 CCAGGGATCCTAGGAAGACCTTGGTAACGAACAGAAACAGGCTGTTAAAGAAGCTGGTGC
     GGTCCCTAGGATCCTTCTGGAACCATTGCTTGTCTTTGTCCGACAATTTCTTCGACCACG

       L  E  K  L  E  Q  L  Q  S  H  E  N  E  K  I  Q  K  E  A  Q
  61 TCTGGAGAAACTGGAACAGCTGCAGTCCCACGAGAACGAGAAGATCCAGAAAGAAGCTCA
     AGACCTCTTTGACCTTGTCGACGTCAGGGTGCTCTTGCTCTTCTAGGTCTTTCTTCGAGT

                                          KpnI
       E  A  L  E  K  Q  F  S  H  *  *
 121 GGAAGCTCTGGAGAAGCAGTTCTCCCACTAATGAGGTACCAGGAA
     CCTTCGAGACCTCTTCGTCAAGAGGGTGATTACTCCATGGTCCTT
* indicate a stop codon of the coding sequence
```

For the type C module, pairs of oligonucleotides (1-2, 3-4, 5-6) were assembled first and then 2 μl of the products were combined as template for a second assembly reaction in presence of oligonucleotides 1 and 6. All the oligonucleotides were used at a final concentration of 1 μM. The annealing temperature was 47° C. for the first reaction and 50° C. for the second. 30 PCR cycles were performed with an extension time of 30 s. The same procedure was applied for the other internal and capping modules. BamHI and KpnI restriction sites were used for the direct insertion of the modules into the plasmid pQE30 (Qiagen, Germany). The single modules were then PCR amplified from the vectors, using external primers pQEfor and pQErev (Qiagen, Germany). The modules were assembled stepwise using type IIs restriction enzymes, following the strategy reported by Binz et al., supra. Neighboring modules were digested with the type II enzymes BpiI and BsaI and directly joined together (FIG. 4). The genes coding for the whole proteins were assembled by stepwise ligation of the internal and capping modules. BamHI and KpnI restriction sites were used for insertion of the whole genes into the pQE30 vector and the plasmids were sequenced. The vector provides an N-terminal MRGSHis$_6$ tag for affinity purification (FIG. 5). DNA molecules encoding proteins containing two, four or eight internal modules of the same type and different combinations of capping molecules were generated. The sequence of YC$_2$A after insertion in the vector is shown below as an example. * indicate a stop codon at the end of the coding sequence.

```
DNA coding sequence of YC2A (SEQ ID NO: 94) and
corresponding protein sequence (SEQ ID NO: 93)
                                         BamHI
       M  R  G  S  H  H  H  H  H  H  G  S  E  L  P  Q  M  T  Q  Q
   1 ATGAGAGGATCGCATCACCATCACCATCACGGATCCGAACTGCCGCAGATGACCCAGCAG
     TACTCTCCTAGCGTAGTGGTAGTGGTAGTGCCTAGGCTTGACGGCGTCTACTGGGTCGTC

       L  N  S  D  D  M  Q  E  Q  L  S  A  T  V  K  F  R  Q  I  L
  61 CTGAACTCCGACGACATGCAGGAACAGCTGTCTGCTACCGTTAAATTCCGTCAGATCCTG
     GACTTGAGGCTGCTGTACGTCCTTGTCGACAGACGATGGCAATTTAAGGCAGTCTAGGAC
```

-continued

```
    S  R  D  G  N  E  Q  I  Q  A  V  I  D  A  G  G  L  P  A  L
121 TCTCGTGATGGTAACGAACAAATCCAAGCTGTTATCGATGCTGGTGGTCTGCCGGCTCTG
    AGAGCACTACCATTGCTTGTTTAGGTTCGACAATAGCTACGACCACCAGACGGCCGAGAC

    V  Q  L  L  S  S  P  N  E  K  I  L  K  E  A  A  W  A  L  S
181 GTTCAACTGCTGTCCTCTCCGAACGAGAAGATCCTGAAAGAAGCTGCTTGGGCTCTGTCT
    CAAGTTGACGACAGGAGAGGCTTGCTCTTCTAGGACTTTCTTCGACGAACCCGAGACAGA

    N  L  A  S  G  G  N  E  Q  I  Q  A  V  I  D  A  G  G  L  P
241 AACCTGGCTTCTGGTGGTAACGAACAAATCCAAGCTGTTATCGATGCTGGTGGTCTGCCG
    TTGGACCGAAGACCACCATTGCTTGTTTAGGTTCGACAATAGCTACGACCACCAGACGGC

    A  L  V  Q  L  L  S  S  P  N  E  K  I  L  K  E  A  A  W  A
301 GCTCTGGTTCAACTGCTGTCCTCTCCGAACGAGAAGATCCTGAAAGAAGCTGCTTGGGCT
    CGAGACCAAGTTGACGACAGGAGAGGCTTGCTCTTCTAGGACTTTCTTCGACGAACCCGA

    L  S  N  L  A  S  G  G  N  E  Q  K  Q  A  V  K  E  A  G  A
361 CTGTCTAACCTGGCTTCTGGTGGTAACGAACAGAAACAGGCTGTTAAAGAAGCTGGTGCT
    GACAGATTGGACCGAAGACCACCATTGCTTGTCTTTGTCCGACAATTTCTTCGACCACGA

    L  E  K  L  E  Q  L  Q  S  H  E  N  E  K  I  Q  K  E  A  Q
421 CTGGAGAAACTGGAACAGCTGCAGTCCCACGAGAACGAGAAGATCCAGAAAGAAGCTCAG
    GACCTCTTTGACCTTGTCGACGTCAGGGTGCTCTTGCTCTTCTAGGTCTTTCTTCGAGTC

                                             KpnI
    E  A  L  E  K  Q  F  S  H  *  *
601 GAAGCTCTGGAGAAGCAGTTCTCCCACTAATGAGGTACCCCG
    CTTCGAGACCTCTTCGTCAAGAGGGTGATTACTCCATGGGGC
```

Protein Expression and Purification

The proteins resulting from combinations of capping and internal repeat modules were assembled with the aim to evaluate the impact on soluble protein expression. Thus Na or Ny as N-capping modules were combined with C type internal modules and Ca or Cy C-terminal modules. Proteins containing two or four internal repeat modules were investigated.

*E. coli* XL1-Blue cells were transformed with the respective plasmid and grown in LB medium containing 1% (w/v) glucose and 50 μg/mL of ampicillin at 37° C. with vigorous shaking. Expression was induced by IPTG (final concentration of 0.5 mM) when the culture reached $OD_{600}$=0.6. After 3 hours of expression, cells were harvested by centrifugation. Protein purification was performed at 4° C. Cells were resuspended in 50 mM Tris-HCl, 500 mM NaCl, pH 8.0, and lysed in a French pressure cell (SLM Instruments, USA) at a pressure of 1'200 PSI. The lysis mixture was further homogenized by sonication (Branson, USA). Insoluble material was pelleted by centrifugation at 20,000×g for 30 min. The supernatant was purified by immobilized metal-ion affinity chromatography (IMAC) with Ni-NTA material (Qiagen), equilibrated with buffer containing 50 mM Tris-HCl, 500 mM NaCl, 10% (v/v) glycerol, 20 mM imidazole (pH 8.0). Columns were washed extensively with the equilibration buffer and then proteins were eluted with an elution buffer identical to the equilibration buffer except for 250 mM imidazole. For importin-α5 the expression was carried out at 25° C. for 6 hours and the cell pellet was resuspended in lysis buffer containing 50 mM Tris-HCl, 500 mM NaCl, 10% glycerol, 5 mM β-mercaptoethanol, 10 mM imidazole (pH 8.0). IMAC purification was performed as indicated above using the same buffers with the addition 5 mM β-mercaptoethanol. Samples were then dialysed overnight in 50 mM Tris-HCl, 2 mM DTT and applied to a POROS HQ anion exchange column, equilibrated with running buffer (50 mM Tris-HCl, pH 8.0), using a Biocad 700 E perfusion chromatography workstation (Applied Biosystems, Germany). The column was then washed with 50 mM Tris-HCl and 20 mM NaCl (pH 8.0) and the samples eluted with a gradient from 20 mM until 1 M NaCl. Protein size and purity were assessed by 15% SDS-PAGE gels, stained with Coomasie PhastGel Blue R-350 (GE Healthcare, Switzerland). The expected mass of all the studied proteins was confirmed by mass spectrometry. Protein concentrations were determined by absorbance at 280 nm using molecular masses and extinction coefficient calculated with the tools available at www.expasy.org and by bicinchoninic acid (BCA) assay (Pierce).

The highest level of soluble protein expression was obtained when combining the internal modules with Ny and Ca. Na leads to almost undetectable expression and Cy presence results in a substantial increase of protein amount in the insoluble fraction, after cell lysis. Expression of constructs with Cm, a modified yeast C-terminal capping repeat without the three initial residues and with alanine replacing Cys19, did not improve the level of soluble protein, compared to Cy. The observed effects of terminal capping modules were independent from the number of internal repeat modules. However, increasing the number of internal modules leads to an increase in the amount of soluble protein and in the absolute amount of protein. The proteins were purified by immobilized metal-ion affinity chromatography (IMAC) in a single step providing more than 100 mg of pure protein from 1 liter of bacterial culture. No sign of precipitation or degradation was detected in protein solution stored for up to one month at 4° C. in the IMAC elution buffer.

Size Exclusion Chromatography (SEC) and Multi-Angle Light Scattering (MALS)

Analytical SEC was carried out on an ÄKTA explorer chromatography system using a Superdex 200 10/30 GL column (flow rate 0.5 ml/min) (GE Healthcare, Switzerland). Phosphate buffer pH 7.4 (50 mM phosphate, 150 mM NaCl) and two Tris-based buffers (20 mM Tris-HCl, 50 mM NaCl, pH 8.0 or 50 mM Tris-HCl, 500 mM NaCl, pH 8.0) were used. The armadillo domain of β-catenin was soluble only at 150 mM or 500 mM salt concentration. The armadillo domain of importin-α5 was analyzed in phosphate buffer pH 7.4 (50 mM phosphate, 500 mM NaCl, 5 mM DTT). MALS measurements were performed with a miniDAWN light scattering detector and an Optilab refractometer (Wyatt Technologies, USA) coupled to the ÄKTA system. Molecular weight estimates were calculated using the ASTRA 4.73.04 software package (Wyatt Technologies, USA). The designed proteins show high apparent molecular masses in size exclusion chromatography (SEC), in contrast to natural armadillo domains (Table 4). C type proteins are always detected as monomers in MALS, up to the highest concentration tested (4 mg/ml). $YC_2A$ represents the only exception: Independently of the concentration, the MALS calculated mass values are always intermediate between monomer and dimer.

Circular Dichroism (CD) Spectra

CD measurements were performed on a Jasco J-810 spectropolarimeter (Jasco, Japan) using a 0.5 mm cylindrical thermo-cuvette. CD spectra were recorded from 190 to 250 nm with data pitch of 1 nm, scan speed of 20 nm/min, response time of 4 sec, and band width of 1 nm. Each spectrum was recorded three times and averaged. Measurements were performed at 20° C. The CD signal was corrected by buffer subtraction and converted to mean residue ellipticity (MRE). Measurements were performed in 20 mM Tris-HCl, 50 mM NaCl (pH 8.0); CD spectra of armadillo domain of β-catenin or importin-α5 were measured in 50 mM Tris-HCl, 500 mM NaCl, pH 8.0 to avoid possible aggregation problems. CD spectra were analyzed using CDpro (Sreerama N. and Woody R. W., Methods Enzymol 383:318-51, 2004): The CDSSTR algorithm was chosen for the analysis, with the reference protein set SDP48 (Ibasis=7). The CD spectra indicate the presence of α-helical secondary structure. The helical content generally increases whit increasing number of internal modules. The values of mean residue ellipticity (MRE) and helical content are indicated in Table 4.

Thermal Denaturation

Heat denaturation curves were obtained by measuring the CD signal at 222 nm with a temperature ramp from 20 to 95° C. (data pitch 1 nm; heating rate 1° C./min; response time 4 sec; band width 1 nm). Data were processed as described above. A gradual decrease in the value of MRE was observed for C type proteins, but no clear cooperative transition. The thermal unfolding was almost completely reversible. The midpoint of transition for each protein is indicated in Table 4.

ANS Binding

1-Anilino-naphthalene-8-sulfonate (ANS) fluorescence was measured using a PTI QM-2000-7 fluorometer (Photon Technology International, USA). The measurements were performed at 20° C. in 20 mM Tris-HCl, 50 mM NaCl, 100 μM ANS, pH 8.0 using purified proteins at a final concentration of 10 μM. ANS binding to armadillo domain of β-catenin was measured in 50 mM Tris-HCl, 500 mM NaCl, 100 μM ANS, pH 8.0 to avoid possible aggregation problems. The emission spectrum from 400-650 nm (1 nm/s) was recorded with an excitation wavelength of 350 nm. For each sample, three spectra were recorded and averaged. C type proteins strongly bind ANS, a fluorescent dye sensitive to hydrophobic environment, suggesting the presence of an accessible hydrophobic core. The values of maximum of ANS fluorescence intensity are indicated in Table 4.

Example 2

The example reports a consensus design strategy applied to generate designed armadillo repeat proteins based on sequences of importin-α subfamily. The design procedure was based on the generation of self-compatible modules. A consensus sequence (type I) was derived from multiple alignments of single armadillo repeat units from the SWISSProt database (http://www.expasy.ch) and combined with the capping modules as described in Example 1. Proteins were expressed, purified and characterized by size exclusion chromatography, ANS binding, circular dichroism spectroscopy and denaturation experiments.

Consensus Design of Type I Internal Module

From the 243 sequences included in the generation of the consensus sequence described in Example 1, the 133 repeat sequences from importin-α subfamily were used to obtain a consensus sequence (Table 6). This restricted consensus avoids possible incompatibility between different subfamilies. The automatic alignments, obtained with clustalW, were manually refined including also the loop connecting adjacent repeat units. The consensus sequences were further improved taking into account information from the crystal structures to reduce possible steric clashes. Requirements for the cloning strategy were also considered at this stage, leading to modules type I (Table 3 and 6).

TABLE 6

Importin consensus

| | 1 | | | | 5 | | | | | 10 | | | | | 15 | | | | | 20 | | | |
|---|---|---|---|---|---|---|---|---|---|---|---|---|---|---|---|---|---|---|---|---|---|---|---|
| consensus | N | P | Q | I | Q | A | V | I | D | A | G | A | L | P | P | L | V | E | L | L | S | S | P |
| rel. freq. | 31 | 30 | 59 | 47 | 44 | 20 | 55 | 50 | 28 | 30 | 59 | 27 | 36 | 62 | 19 | 64 | 36 | 17 | 77 | 87 | 24 | 26 | 20 |
| 2nd cons. | D | E | P | T | D | V | L | V | E | S | N | V | V | K | R | F | I | N | F | I | T | H | A |
| rel. freq. | 18 | 26 | 21 | 29 | 14 | 17 | 17 | 29 | 14 | 21 | 15 | 26 | 31 | 8 | 16 | 30 | 20 | 11 | 11 | 8 | 13 | 24 | 10 |
| 3rd cons. | S | D | K | P | K | Y | I | L | Q | C | Q | I | I | S | V | I | C | S | C | M | Q | K | N |
| rel. freq. | 18 | 19 | 7 | 14 | 11 | 11 | 8 | 8 | 14 | 11 | 6 | 23 | 23 | 8 | 13 | 4 | 14 | 11 | 4 | 4 | 9 | 10 | 10 |
| consensus | N | P | Q | I | Q | A | V | I | D | A | G | A | L | P | P | L | V | E | L | L | S | S | P |
| refinement | | E | | | | | | | | | | | | | V | | | | | | | | |
| binding | | | | x | | | | | | | | | | | | | | | | | | | |
| type I | N | E | Q | I | Q | A | V | I | D | A | G | A | L | P | V | L | V | E | L | L | S | S | P |

| | 25 | | | | | | 30 | | | | 35 | | | | | | 40 | | |
|---|---|---|---|---|---|---|---|---|---|---|---|---|---|---|---|---|---|---|---|
| consensus | D | E | K | I | Q | K | E | A | L | W | A | L | S | N | I | T | S | G | G |
| rel. freq. | 49 | 14 | 24 | 38 | 33 | 29 | 43 | 77 | 29 | 71 | 70 | 52 | 41 | 86 | 68 | 34 | 24 | 71 | 28 |
| 2nd cons. | E | F | S | V | L | E | D | T | A | R | T | I | C | Y | L | A | A | D | T |
| rel. freq. | 17 | 14 | 14 | 34 | 17 | 15 | 14 | 7 | 26 | 14 | 13 | 28 | 29 | 14 | 17 | 26 | 15 | 15 | 21 |
| 3rd cons. | K | N | D | L | V | F | V | S | V | D | G | V | T | — | A | V | T | A | N |
| rel. freq. | 14 | 11 | 12 | 14 | 13 | 14 | 14 | 6 | 23 | 8 | 11 | 17 | 21 | 0 | 7 | 14 | 15 | 9 | 14 |
| consensus | D | E | K | I | Q | K | E | A | L | W | A | L | S | N | I | T | S | G | G |
| refinement | | N | | | | | | | | | | | | | | | | | |

TABLE 6-continued

| Importin consensus | | | | | | | | | | | | | | | | | |
|---|---|---|---|---|---|---|---|---|---|---|---|---|---|---|---|---|---|
| binding | | | x | | | x | x | | | x | | | x | N | | | x | x | |
| type I | D | N | K | I | Q | K | E | A | L | W | A | L | S | N | I | T | S | G | G |

Consensus sequence derived from multiple sequence alignment and refinement to modules type I (SEQ ID NO: 1).
The numbers indicate the positions inside the single repeats according to the nomenclature introduced.
The most frequent, the second and the third most frequent residue are indicated, with the relative frequency (rel. freq.) expressed as percentage.
Modifications introduced during the refinement and positions responsible for binding (indicated by x and the conserved N) are shown.
Consensus (SEQ ID NO: 114), 2nd cons. (SEQ ID NO: 115), and 3rd cons. (SEQ ID NO: 116) sequences are shown.

The putative helices H1, H2, H3 cover the residues 1-10, 12-21, 25-40, respectively. The positions 7, 16, 17, 19, 20, 31, 34, 35, 38 are well conserved in all the sequences and are part of the hydrophobic core of the armadillo proteins. Gln5 can potentially form a hydrogen bond with Asp9 of the same repeat unit, stabilizing H1 (observed in structure 1EE5). Gly11 is conserved for its crucial role in bending the polypeptide chain between H1 and H2, being compatible with a positive $\phi$ angle required at this position. Pro14 is an unusual conserved feature of armadillo repeat units, present at a frequency of 62% in importin repeat units alignment. It is located at the beginning of H2, at a position where it is still not necessary to involve the backbone nitrogen in a hydrogen bond; instead of disrupting the secondary structure, it adopts the $\phi/\psi$ angles typical for $\alpha$ helices. Asn37 is a well conserved residue, due to its critical role in binding to the backbone of target peptides and Trp33 is also involved in binding, specifically in the recognition of target side chains. The positions potentially involved in binding of peptides (4, 26, 29, 30, 33, 36, 37, 40, 41) have been defined according to Example 1. Further modifications were introduced in the original consensus sequences (Table 6), as in Example 1. Pro2 (30%) was substituted with the approximately equally conserved Glu (26%), as Pro at such position would probably disrupt H1, as indicated by importin-$\alpha$ crystal structures. Pro15 (19%) was derived from the sequences which do not possess a Pro in position 14. A double Pro14-Pro15 never occurs in the observed sequences and it is likely to be extremely destabilizing for H2. This position is usually occupied by small hydrophobic residues in combination with Pro14. Arg represents a relatively common choice (16%) but it occurs almost exclusively in the second repeat unit of natural importins. Val was therefore chosen as substitution due to the slightly higher frequency of occurrence (13%). Positions 24 and 25 at the joint between loop H2-H3 and H3 show a clear preference for acidic residues in all consensus sequences. However, a pair of negatively charged residues never occurs in the observed sequences, and it could lead to charge repulsion or formation of a negatively charged belt along the whole protein. The most conserved residue, Asp24 (49%), was preserved. To reduce the local negative charge, Asn (11%) was chosen to replace Glu (19%) at position 25, because it is the second most frequent polar residue. Gly has been introduced at position 42 for cloning purposes. It is remarkable that, because of short H3-H1 loops (1-3 residues in general), very often one position of the loop is occupied by a Gly. Taking into account that position 41 is sometimes involved in binding and then possibly subjected to mutation for applications, it is important to keep a constant glycine inside the loop to maintain the required flexibility.

Synthesis of DNA Encoding the Designed Armadillo Repeat Proteins

The peptide sequence of the Type I module was back-translated to DNA sequence, optimizing the codon usage for expression in *E. coli*. The DNA molecule corresponding to the Type I module was synthesized starting from overlapping oligonucleotides (Table 2). Assembly PCR, ligation (between modules and with capping modules described in Example 1) and cloning were performed according to Example 1, to obtain genes coding for armadillo repeat proteins containing one Ny N-terminal capping module, 2, 4 or 8 internal Type I modules and one Ca C-terminal capping module.

Biophysical Characterization

Protein expression and purification, as well as size exclusion chromatography (SEC), multi-angle light scattering (MALS), circular dichroism (CD), thermal and guanidinium-induced denaturation and ANS binding were performed according to Example 1. The expression and purification yields were comparable to the proteins described in Example 1.

The designed I type proteins show, in size exclusion chromatography (SEC), high apparent molecular masses, in contrast to natural armadillo domains (Table 4). Multi-angle light scattering (MALS) indicates that the they are probably present as mixture of dimers and monomers in solution. The main peak corresponds to the dimeric form and this value has been reported in Table 4. At high concentration (2-4 mg/ml), I type proteins are present as mixture of oligomers with even higher apparent molecular masses. The CD spectra indicate the presence of $\alpha$-helical secondary structure content for all proteins, with ellipticity at 222 nm as in the natural armadillo domain of importin-$\alpha$ ($\alpha$Arm) and $\beta$-catenin ($\beta$Arm). The helical content generally increases with increasing number of internal modules. I type proteins show cooperative transition in thermal denaturation and the midpoint of transition (Tm) increases with the number of modules, e.g. from approximately 70° C. for $YI_4A$ to more than 80° C. for $YI_8A$. The designed proteins retain a significant percentage of secondary structure at 95° C., and the thermal unfolding is almost completely reversible. The values of mean residue ellipticity (MRE), helical content and midpoint of transition in thermal denaturation are indicated in Table 4. In ANS binding experiments, I type proteins show ANS binding in the same range as the natural armadillo repeat proteins, indicating the presence of a compact hydrophobic core not accessible to the dye. The maximum values of ANS fluorescence intensity are indicated in Table 4.

Example 3

The example reports a consensus design strategy applied to generate designed armadillo repeat proteins based on sequences of the $\beta$-catenin subfamily. The design procedure was based on the generation of self-compatible modules. A consensus sequence (type T) was derived from multiple alignments of single armadillo repeat units from the SWISS-Prot database (http://www.expasy.ch) and combined with the capping modules as described in Example 1. Proteins were expressed, purified and characterized by size exclusion chromatography, ANS binding, circular dichroism spectroscopy and denaturation experiments.

Consensus Design of Type T Internal Module

From the 243 sequences included in the generation of the consensus sequence described in Example 1, the 110 repeat sequences from the β-catenin subfamily were used to obtain a consensus sequence. This restricted consensus avoids possible incompatibility between different subfamilies.

The automatic alignments, obtained with clustalW, were manually refined including also the loop connecting adjacent repeat units (Table 7). The consensus sequences were further improved taking into account information from the crystal structures to reduce possible steric clashes. Requirements for the cloning strategy were also considered at this stage, leading to modules type T (Tables 3 and 7).

based alignment. Cys30 (18%) and Cys41 (21%) were replaced by the second most common amino acid (Ala 12% and His 17%, respectively), to avoid the formation of undesired disulfide bonds that might limit possible future applications. Position 9 shows a preference for long aliphatic side-chains, either non-polar or polar (Leu, Glu, Gln); however, this residue is solvent-exposed, and Leu9 (21%) was substituted by the second most common amino acid Glu (19%). Gln is the most frequent amino acid (27%) at position 18. However, both Arg and Lys are represented almost at the same frequency (25% and 20% respectively), indicating a preference for positively charged residues. Arg has been then chosen at this position due to its higher frequency. Positions 24 and 25 at the joint between loop H2-H3 and H3 show a clear preference for acidic residues in all consensus sequences.

TABLE 7

Catenin/plakoglobin consensus

| | 1 | | | | 5 | | | | | 10 | | | | | 15 | | | | | 20 | | | |
|---|---|---|---|---|---|---|---|---|---|---|---|---|---|---|---|---|---|---|---|---|---|---|---|
| consensus | E | A | N | K | L | A | I | R | L | S | G | G | I | P | A | L | V | Q | L | L | S | S | N |
| rel. freq. | 31 | 23 | 44 | 44 | 22 | 48 | 53 | 37 | 21 | 31 | 56 | 58 | 38 | 35 | 46 | 63 | 85 | 27 | 49 | 71 | 14 | 35 | 24 |
| 2nd cons. | P | E | S | R | M | I | V | F | E | A | N | L | L | Q | K | I | G | R | T | M | G | P | D |
| rel. freq. | 16 | 18 | 26 | 22 | 19 | 12 | 32 | 13 | 19 | 24 | 10 | 9 | 27 | 28 | 10 | 11 | 7 | 25 | 15 | 18 | 11 | 11 | 21 |
| 3rd cons. | Q | M | A | L | A | P | L | V | Q | N | Y | V | V | A | R | M | I | K | H | I | R | Y | P |
| rel. freq. | 14 | 11 | 17 | 11 | 17 | 11 | 14 | 11 | 14 | 10 | 10 | 7 | 16 | 8 | 8 | 10 | 4 | 20 | 10 | 7 | 10 | 11 | 21 |
| consensus | E | A | N | K | L | A | I | R | L | S | G | G | I | P | A | L | V | Q | L | L | S | S | N |
| refinement | | | | | | | | | E | | | | | | | | | R | | | | | |
| binding | | | | x | | | | | | | | | | | | | | | | | | | |
| type T | E | A | N | K | L | A | I | R | E | S | G | G | I | P | A | L | V | R | L | L | S | S | N |

| | | 25 | | | | 30 | | | | | 35 | | | | | 40 | | |
|---|---|---|---|---|---|---|---|---|---|---|---|---|---|---|---|---|---|---|
| consensus | D | E | K | I | L | E | C | A | T | G | T | L | H | N | L | A | L | C | N |
| rel. freq. | 20 | 43 | 20 | 31 | 33 | 20 | 18 | 44 | 23 | 47 | 30 | 89 | 30 | 50 | 97 | 39 | 21 | 21 | 40 |
| 2nd cons. | V | V | N | L | V | R | A | T | A | C | A | I | R | I | V | S | C | H | H |
| rel. freq. | 13 | 14 | 20 | 30 | 30 | 18 | 12 | 35 | 21 | 10 | 20 | 9 | 30 | 17 | 2 | 31 | 10 | 17 | 22 |
| 3rd cons. | R | W | E | V | T | K | Y | C | I | W | V | V | S | V | M | T | Y | D | Q |
| rel. freq. | 11 | 10 | 19 | 19 | 13 | 12 | 10 | 16 | 18 | 10 | 20 | 1 | 11 | 10 | 1 | 20 | 10 | 16 | 20 |
| consensus | D | E | K | I | L | E | C | A | T | G | T | L | H | N | L | A | L | C | N |
| refinement | N | | | | | | A | | | | | | | | | | | H | G |
| binding | | | x | | | x | x | | | x | | | x | N | | | x | x | |
| type T | N | E | K | I | L | E | A | A | T | G | T | L | H | N | L | A | L | H | G |

Consensus sequence derived from multiple sequence alignment and refinement to modules type T (SEQ ID NO: 2).
The numbers indicate the positions inside the single repeats according to the nomenclature introduced.
The most frequent, the second and the third most frequent residue are indicated, with the relative frequency (rel. freq.) expressed as percentage.
Modifications introduced during the refinement and positions responsible for binding (indicated by x and the conserved N) are shown.
Consensus (SEQ ID NO: 117), 2nd cons. (SEQ ID NO: 118), and 3rd cons. (SEQ ID NO: 119) sequences are shown.

The putative helices H1, H2, H3 cover the residues 1-10, 12-21, 25-40, respectively. The positions 7, 16, 17, 19, 20, 31, 34, 35, 38 are well conserved in all the sequences and are part of the hydrophobic core of the armadillo proteins. Gly11 is conserved for its crucial role in bending the polypeptide chain between H1 and H2, being compatible with a positive $\phi$ angle required at this position. Pro14 is an unusual conserved feature of armadillo repeat units, present at a frequency of 35% in catenin/plakoglobin repeat units alignment. It is located at the beginning of H2, at a position where it is still not necessary to involve the backbone nitrogen in a hydrogen bond; instead of disrupting the secondary structure, it adopts the $\phi/\psi$ angles typical for $\alpha$ helices. Asn37 is a well conserved residue in all consensus sequences, due to its critical role in binding to the backbone of target peptides. The positions potentially involved in binding of peptides (4, 26, 29, 30, 33, 36, 37, 40, 41) have been defined according to Example 1. Further modifications were introduced in the original consensus sequence (Table 7) to meet the requirements for protein production (e.g. lack of cysteines) or to avoid structural defects (e.g. presence of clashes) that could have arisen from a purely sequence- However, a pair of negatively charged residues never occurs in the observed sequences, and it could lead to charge repulsion or formation of a negatively charged belt along the whole protein. The most conserved residue, Glu25 (43%), was retained. Asp24 (20%) was substituted by Asn (10%), a choice driven by the similarity to the original residue in a pool of candidates with almost the same frequency (Arg, Asn, Met, Ser, Tyr, Val). Gly has been introduced at position 42 for cloning purposes. It is remarkable that, because of short H3-H1 loops (1-3 residues in general), very often one position of the loop is occupied by a Gly. Taking into account that position 41 is sometimes involved in binding and then possibly subjected to mutation for applications, it is important to keep a constant glycine inside the loop to maintain the required flexibility.

Synthesis of DNA Encoding the Designed Armadillo Repeat Proteins

The peptide sequence of the type T module was back-translated to DNA sequence, optimizing the codon usage for expression in *E. coli*. The DNA molecule corresponding to the type T module was synthesized starting from overlapping oligonucleotides (Table 2). Assembly PCR, ligation (between modules and with capping modules described in Example 1) and cloning were performed according to Example 1, to obtain genes coding for armadillo repeat proteins containing one Ny N-terminal capping module, 2, 4 or 8 internal type T modules and one Ca C-terminal capping module.

Biophysical Characterization

Protein expression and purification, as well as size exclusion chromatography (SEC), multi-angle light scattering (MALS), circular dichroism (CD), thermal and guanidinium-induced denaturation and ANS binding were performed according to Example 1. The designed proteins show, in SEC, high apparent molecular masses, in contrast to natural armadillo domains (Table 4). MALS indicates that the T type proteins are probably present as mixture of dimers and monomers in solution. The main peak corresponds to the dimeric form and this value has been reported in Table 4. At high concentration (2-4 mg/ml), T type proteins are present as mixture of oligomers with even higher apparent molecular masses. The CD spectra do not show any significant correlation between the helical content and number of internal modules. The values of mean residue ellipticity (MRE) and helical content are indicated in Table 4. In thermal denaturation, T type proteins show cooperative transition and the midpoint of transition (Tm) seems to increases with the number of modules. The thermal unfolding is not completely reversible for $YT_2A$ and $YT_4A$, and $YT_8A$ is irreversibly denatured. The values of mean residue ellipticity (MRE), helical content and midpoint of transition (Tm) are indicated in Table 4. In ANS binding experiments, T type proteins show ANS binding in the same range as the natural armadillo repeat proteins. The maximum values of ANS fluorescence intensity are indicated in Table 4.

Example 4

A collection of designed armadillo repeat proteins with improved hydrophobic core is described. Proteins containing new types of internal modules were derived from the type C module of Example 1, using a computational "rotamer sampling" approach. From the C type module 7 out of 16 positions which contribute to hydrophobic core formation were selected as targets for aliphatic to aliphatic mutations. Starting from crystal structures of natural armadillo domains, model structures were generated substituting the core positions of every internal repeat unit by the residues present in the C type module and the allowed mutations. In each structure, every repeat module of the protein carries the same mutations. A rotamer sampling approach, followed by energy minimization, resulted in a series of structures and corresponding energy values that were used to obtain the final rank of the mutants. Eighteen top ranking mutants were then generated at the DNA level introducing in the internal modules, based on C type module, the selected residues. The proteins were expressed and compared to the corresponding protein containing the original C type modules. High level of expression of soluble proteins was achieved for the mutants and all show improvements in their biophysical characteristics when compared to the original type C module, while retaining in almost all the cases a monomeric form in solution. The presence of secondary structure and of a stable, globular protein, was confirmed by circular dichroism spectroscopy, ANS binding, NMR and denaturation experiments.

Rotamer Sampling in Hydrophobic Core Mutants

The C type module described in Example 1 (Table 3) was chosen as starting point for the generation of new types of modules able to increase the compactness and native-like behavior of proteins containing them, compared to proteins containing the original C type module. A packing problem of the hydrophobic core is a possible explanation for the molten globule like behavior of C type proteins. Mutations in the hydrophobic core positions can then improve the protein packing. The 16 positions contributing to the hydrophobic core formation (FIG. 6 and Table 8) were defined by a solvent accessible surface lower than 5% of the total residue surface, as determined by a probe with 1.4 Å radius. The final choice was made after visual inspection of the structures. The number of mutations was restricted to the common aliphatic amino acids at each position, based on the sequence alignment, while keeping the most conserved positions constant. Only 7 positions out of the 16 forming the hydrophobic core of a single repeat module were allowed to vary and to host two or three different residue types, depending on their frequency at these positions (Table 8).

TABLE 8

Hydrophobic core positions and mutations

| Core positions | 4 | 7 | 12 | 13 | 16 | 17 | 19 | 20 | 27 | 28 | 31 | 32 | 34 | 35 | 38 | 39 |
|---|---|---|---|---|---|---|---|---|---|---|---|---|---|---|---|---|
| C type | I | V | G | L | L | V | L | L | I | L | A | A | A | L | L | A |
| alternative | | | A | I | | | | | L | V | | L | V | | I | |
| residues | | | | V | | | | | V | | | V | | | | |

The number of possible combinations of mutations in each repeat module is then 432. To improve sampling, three X ray structures were chosen as starting models: Importin-α from *S. cerevisiae* (PDB ID 1EE4) and mouse (PDB ID 1Q1T) consisting each of 8 internal repeat units and 2 terminal repeat units, and murine β-catenin (PDB ID 2BCT), which consists of 10 internal repeat units and 2 terminal repeat units.

The original capping repeat units of the three structures were substituted with Ny and Ca capping modules (Table 3) in the models. Each mutation was modeled by deleting the side chains at the core positions of each repeat unit and substituting them with the new side chains with a random rotamer conformation; the resulting structure was minimized to eliminate clashes. The final outcome was a group of 3 models (from the three initial structures) for each of the 432 combinations of allowed mutations. All the repeat modules in each model were designed to have the same mutation pattern. A sequence of heating-quench cycles, followed by energy minimization, resulted in a series of structures and corresponding energy values that were used to generate the final ranking of the mutants (Table 9). Mutants with a hydrophobic core volume lower than the original type C module, calculated with values reported by Chothia C., Nature 275:304-8, 1975, were not included in the final ranking, to reduce the number of false positives which might arise due to underpacking of the core.

TABLE 9

| Hydrophobic core of the selected mutants | | | | | | | | | | | | | | | | |
|---|---|---|---|---|---|---|---|---|---|---|---|---|---|---|---|---|
| | Hydrophobic core residues | | | | | | | | | | | | | | | |
| | 4 | 7 | 12 | 13 | 16 | 17 | 19 | 20 | 27 | 28 | 31 | 32 | 34 | 35 | 38 | 39 |
| C type | I | V | **G** | **L** | L | V | L | L | **I** | **L** | A | **A** | **A** | L | **L** | A |
| mut1 | - | - | - | - | - | - | - | - | **L** | - | - | **L** | - | - | - | - |
| mut2 | - | - | **A** | - | - | - | - | - | **V** | - | - | **L** | - | - | - | - |
| mut3 | - | - | **A** | - | - | - | - | - | **L** | - | - | **L** | - | - | - | - |
| mut4 | - | - | **A** | - | - | - | - | - | **L** | - | - | - | - | - | **I** | - |
| mut5 | - | - | **A** | - | - | - | - | - | **L** | - | - | - | **V** | - | - | - |
| mut6 | - | - | **A** | - | - | - | - | - | **L** | - | - | - | - | - | - | - |
| mut7 | - | - | **A** | - | - | - | - | - | - | - | - | **L** | - | - | **I** | - |
| mut8 | - | - | **A** | **V** | - | - | - | - | **L** | - | - | **L** | - | - | - | - |
| mut9 | - | - | **A** | **I** | - | - | - | - | **L** | - | - | **L** | - | - | - | - |
| mut10 | - | - | **A** | - | - | - | - | - | **L** | - | - | **V** | - | - | - | - |
| mut11 | - | - | **A** | - | - | - | - | - | **V** | - | - | **L** | **V** | - | - | - |
| mut12 | - | - | **A** | - | - | - | - | - | **L** | - | - | **L** | **V** | - | - | - |
| mut13 | - | - | **A** | **I** | - | - | - | - | **L** | - | - | **L** | **V** | - | - | - |
| mut14 | - | - | **A** | - | - | - | - | - | **L** | - | - | **V** | **V** | - | - | - |
| mut15 | - | - | **A** | - | - | - | - | - | - | - | - | - | - | - | - | - |
| mut16 | - | - | - | - | - | - | - | - | **L** | - | - | **L** | - | - | **I** | - |
| mut17 | - | - | **A** | **V** | - | - | - | - | **L** | - | - | **L** | **V** | - | **I** | - |
| mut18 | - | - | **A** | **I** | - | - | - | - | - | - | - | - | - | - | - | - |
| mut19 | - | - | - | - | - | - | - | - | **L** | - | - | - | - | - | - | - |
| I type | - | - | **A** | - | - | - | - | - | - | **Q** | - | **L** | - | - | **I** | T |

Figure 1:
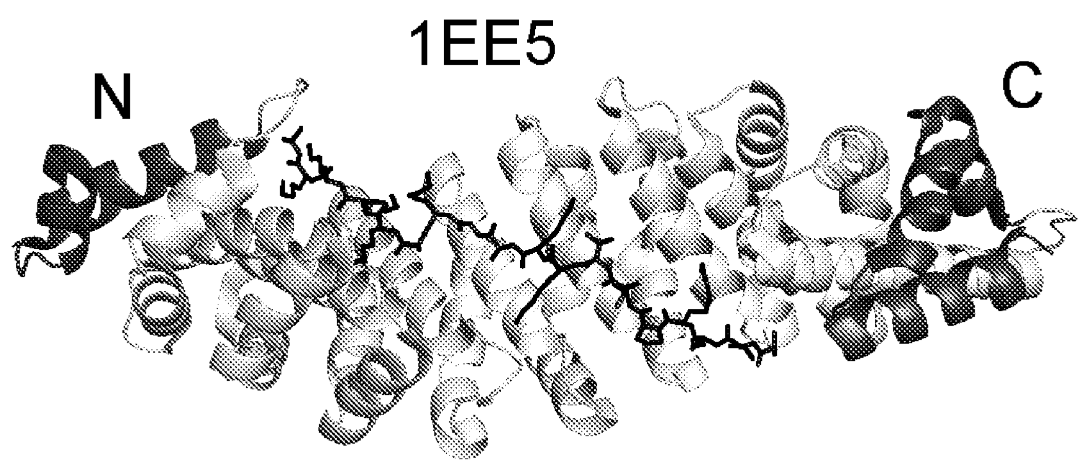
FIG. 1. Armadillo Repeat Protein Structure.
Figure 1:
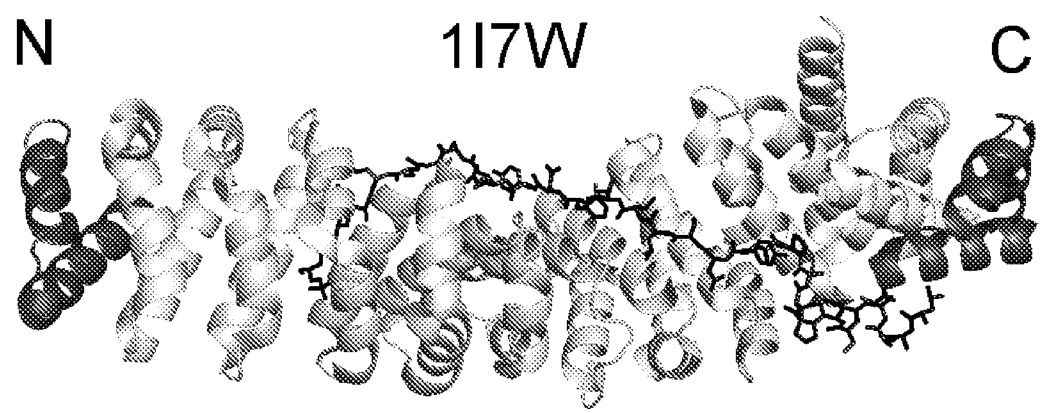

The numbers indicate the positions in the single repeat (cf. FIG. 1). The hydrophobic core positions subjected to rotamer sampling (12, 13, 27, 28, 32, 34, 38) are indicated in bold. The amino acids present at each position are reported as single letter code. "—" indicates no difference with respect to C type consensus. As a comparison, in the last row the sequence corresponding to the I type consensus is shown.

The computational approach uses the CHARMM force field (Brooks B. R. et al., Journal of Computational Chemistry 4:187-217, 1983) and cycles of energy minimization and heating by molecular dynamics to sample favorable arrangements of the buried side chains and estimate the packing efficiency of residues in the hydrophobic core of a given mutant. The extended atom approximation (param19) with distance-dependent dielectric function was used for both energy minimization and heating by short molecular dynamics runs. All the backbone atoms and side chain atoms not directly in contact with core residue atoms (i.e., those more than 5 Å away, in the initial conformation, from any atom of the 16 core residues of each repeat unit) were constrained with a harmonic potential with a constant of 1.0 kcal·mol$^{-1}$·Å$^{-2}$. In this way, only the side chain rotatable bonds of the core residues are fully flexible. The system with the harmonic potential was further minimized. A heating-quench protocol was iterated 100 times for each of the 432 mutants and each of the three protein structures. The first step was a 10 ps heating to 400 K, neglecting the non-bonding energy terms (i.e., van der Waals and the electrostatics). The second step was a minimization including all energy terms. The aim of the heating phase was to shuffle the flexible side chain rotamers and allow them to jump over energy barriers, while minimization was used to reach the nearest minimum in the potential energy after the heating step. At the end of the minimization the coordinates were stored so that a total of 100 conformations were generated for each mutant. These conformations were finally minimized without the aforementioned constraints, and the potential energy was evaluated for ranking.

The CHARMM potential energy is:

$$E=E_{bonding}+E_{vdw}+E_{elec} \quad \text{(eq. 1)}$$

where $E_{bonding}$ is the sum of bond, angle, improper and dihedral potential terms, $E_{vdw}$ is the van der Waals total interaction energy, and $E_{elec}$ is the Coulombic energy. The $E_{elec}$ term was neglected for ranking because it is insensitive to aliphatic to aliphatic mutations in the extended atom representation. Moreover, because of the constraints, the restricted flexibility of the backbone polar groups results in a noisy Coulombic energy without significant signal. Therefore, a reduced potential energy was used for ranking. For each starting structure, the energy value for the conformation i of mutant m is:

$$E_i^m=E_{i,bonding}^m+E_{i,vdw}^m \quad \text{(eq. 2)}$$

As each conformer has a different potential energy, median, 1$^{st}$ percentile and minimum were extracted from the energy series of the conformers to characterize each mutant, and the values were used to make three independent ranks. At the end of this procedure, for each of the three initial structures, three rank numbers (corresponding to median, 1$^{st}$ percentile and minimum ranking) were assigned to each mutant, and these nine rank numbers were summed. The resulting number was used to obtain the overall mutant rank. The combination of multiple structures and different scoring criteria (i.e., median, 1$^{st}$ percentile and minimum) was used to take into account, in an approximate way, the limited sampling. In this way, a high ranking position requires a consistent performance of a mutant over many conformations and in three different backbones, using three different ways to weight the potential energy. The CPU time required for each starting model of a mutant was approximately 5 hours per importin structures and 7 hours for catenin structures on a single processor of a 2800 MHz Opteron dual core. The total calculation time of approximately 8000 hours was split into 150 CPUs.

Synthesis of DNA Encoding the Designed Armadillo Repeat Proteins

Among the (30) top ranking single repeat module mutant sequences, eighteen were selected for experimental validation. The best ranking mutant sequence with low core volume was also selected to challenge the initial choice of a core volume filter during the ranking process. The influence of mutant repeat modules on the protein properties was evaluated in the format of proteins containing four identical internal modules and the capping modules Ny and Ca described in Example 1. The proteins were named mut1 to mut18; mut19 contains the sequence with low core volume (Table 9). The reference protein containing type C modules is referred to as $YC_4A$ as indicated above. The assembly of single modules from oligonucleotides and the stepwise ligations were performed as described in Example 1. The combination of oligonucleotides used for each module, is indicated in Table 10.

TABLE 10

Oligonucleotides used in assembly of mutant internal modules

| Mutant | oligo #1 | oligo #2 | oligo #3 | oligo #4 | oligo #5 | oligo #6 |
|---|---|---|---|---|---|---|
| mut1 | cons1F | cons2R | cons3F | 4LLrev | 5L--for | cons6R |
| mut2 | cons1F | 2A-rev | 3A-for | 4VLrev | 5L--for | cons6R |
| mut3 | cons1F | 2A-rev | 3A-for | 4LLrev | 5L--for | cons6R |
| mut4 | cons1F | 2A-rev | 3A-for | 4L-rev | 5--Ifor | 6Irev |
| mut5 | cons1F | 2A-rev | 3A-for | 4L-rev | 5-V-for | cons6R |
| mut6 | cons1F | 2A-rev | 3A-for | 4L-rev | cons5F | cons6R |
| mut7 | cons1F | 2A-rev | 3A-for | 4-Lrev | 5L-Ifor | 6Irev |
| mut8 | cons1F | 2AVrev | 3AVfor | 4LLrev | 5L--for | cons6R |
| mut9 | cons1F | 2AIrev | 3AIfor | 4LLrev | 5L--for | cons6R |
| mut10 | cons1F | 2A-rev | 3A-for | 4LVrev | 5V--for | cons6R |
| mut11 | cons1F | 2A-rev | 3A-for | 4VLrev | 5LV-for | cons6R |
| mut12 | cons1F | 2A-rev | 3A-for | 4LLrev | 5LV-for | cons6R |
| mut13 | cons1F | 2AIrev | 3AIfor | 4LLrev | 5LV-for | cons6R |
| mut14 | cons1F | 2A-rev | 3A-for | 4LVrev | 5VV-for | cons6R |
| mut15 | cons1F | 2A-rev | 3A-for | cons4R | cons5F | cons6R |
| mut16 | cons1F | cons2R | cons3F | 4LLrev | 5L-Ifor | 6Irev |
| mut17 | cons1F | 2AVrev | 3AVfor | 4LLrev | 5LVIfor | 6Irev |
| mut18 | cons1F | 2AIrev | 3AIfor | cons4R | cons5F | cons6R |
| mut19 | cons1F | cons2R | cons3F | 4L-rev | cons5F | cons6R |

Protein Expression and Purification

The proteins containing the modules selected by the "rotamer sampling" method were expressed and purified as described in Example 1. Expression level of hydrophobic core mutants was approximately the same as for the proteins containing the original C type module. Proteins purified by immobilized metal-ion affinity chromatography (IMAC) in a single step, yielded approximately 100 mg of pure protein from 1 liter of bacterial culture.

Characterization of Selected Hydrophobic Core Mutants

The experimental comparison was carried out by circular dichroism (CD), size exclusion chromatography (SEC) and binding of ANS (1-anilino-naphthalene-8-sulfonate) as described in Example 1. Analytical size exclusion chromatography was carried out either on an Ettan LC system using a Superdex 200 PC 3.2/30 column (flow rate 70 μl/min) and on an ÄKTA explorer chromatography system using a Superdex 200 10/30 GL column (flow rate 0.5 ml/min) (GE Healthcare, Switzerland).

All the mutants share a similar CD spectrum with $YC_4A$, but are characterized by a general increase in mean residue ellipticity at 222 nm, indicating a higher percentage of $\alpha$ helical secondary structure. The increased elution volume of the mutants correlates well with a decreased ANS binding, indicating a higher compactness of the proteins (FIG. 7). mut1 represents the only outlier due to its dimeric form, while all the other mutants are monomers, as indicated by multi-angle light scattering (MALS). Some of the core mutants carry additional mutations, which were introduced during the gene synthesis (indicated in the description of FIG. 7). Most of these mutations are located in loops or at the surface of the helices, and are thus likely to have only small or no influence on the stability of the hydrophobic core; furthermore, they are present only in a single module out of four, reducing their overall contribution to protein properties. The mutants mut2, mut3, mut4, mut7, mut11, mut12 and mut13 show the best combination of low ANS binding and compactness, as judged by SEC, and were selected for further characterization by thermal denaturation. The mutant mut7 shows a significantly increased cooperativity during unfolding, compared to the $YC_4A$ and the other mutants. The internal module corresponding to mut7, which was named M type, contains 3 point mutations compared to the initial consensus (Table 3). The mutant mut7, renamed $YM_4A$, is a stable monomer at several salt and protein concentrations, like $YC_4A$; however, dimer formation was observed at pH 7 with high protein concentration (5 mg/ml). No sign of precipitation or degradation was detected in protein solutions stored for up to one month at 4° C. in the IMAC elution buffer. The biophysical characteristics of $YM_4A$ are indicated in Table 4.

NMR

Proteins for NMR studies were produced using *E. coli* strain M15 (Qiagen) containing the plasmid pREP4 growing in minimal medium with $^{15}N$-labeled ammonium chloride as the only nitrogen source. The medium was supplemented with trace metals, 150 μM thiamine and 30 μg/ml kanamycin. Expression and purification by IMAC and gel filtration were performed as described in Example 1. The buffers used for NMR measurements contained 20 mM deuterated Tris-HCl, 30 mM NaCl and pH of 6, 7, 8, 9, 10 or 11. $YC_4A$ and $YM_4A$ were concentrated to 0.6 mM for NMR measurements. Proton, nitrogen correlation maps were derived from [$^{15}N$,$^{1}H$]-HSQC experiments utilizing pulsed-field gradients for coherence selection and quadrature detection and incorporating the sensitivity enhancement element of Rance and Palmer Palmer A. G. et al., J. Mag. Reson. 93:151-70, 1991; Kay L. E. et al., J Am Chem Soc 114:10663-5, 1992). The $^{15}N\{^{1}H\}$-NOE data were measured using a proton-detected version of the $^{15}N\{^{1}H\}$ steady-state heteronuclear Overhauser effect. All experiments were recorded on a Bruker AV-700 MHz spectrometer equipped with a triple-resonance cryoprobe at 310K. Spectra were processed and analyzed in the spectrometer software TOPSPIN 1.3 and calibrated relatively to the water resonance at 4.63 ppm proton frequency, from which the $^{15}N$ scale was calculated indirectly.

Amide proton frequencies of $YC_4A$ are generally limited to the random-coil range (7.5-8.5 ppm), whereas many cross peaks of $YM_4A$ are located outside this range. Moreover, the line widths from signals of $YC_4A$ are slightly larger than from those of $YM_4A$. Increased line widths due to conformational exchange processes as well as limited signal dispersion are characteristic features of molten-globule states of proteins. Although no attempts have been made to assign the $^{15}N$,$^{1}H$ correlation map, $^{15}N$-$\{^{1}H\}$-NOE data were recorded to characterizing internal backbone dynamics and probe for increased rigidity of $YM_4A$. All amide moieties of $YM_4A$ are characterized by $^{15}N$-$\{^{1}H\}$-NOEs larger than 0.6, indicating well folded segments, whereas for $YC_4A$ all the values are smaller than 0.3, amongst them many with negative NOEs, indicating a large flexibility. NMR measurements confirm then the molten globule characteristics of $YC_4A$ and the native like properties of $YM_4A$.

Example 5

The example refers to a collection of designed armadillo repeat proteins with randomized residues (referred to as a library), which allows the selection of binders to a target peptide.

The armadillo repeat protein library is generated using Ny and Ca capping modules (described in Example 1) and three internal M type modules (described in Example 4) with randomized positions.

Synthesis of DNA Encoding the Designed Armadillo Repeat Proteins

A library was designed at the protein level comprising proteins containing Ny as N-terminal capping module, three internal M type modules with randomized positions and Ca as C-terminal capping module. The residues E, H, K, I, Q, R, T were allowed at position 4 of the M type module. The restriction was due to the steric constraints of position 4, which is also involved in formation of the hydrophobic core. All the residues except C, G and P were allowed at positions 30, 33, 36, 40, 41. Cysteines were excluded to avoid formation of disulfide bridges or protein dimerization. Glycine and proline were excluded because of their helix breaking propensity, due to the fact that all the positions except 41 are localized on α-helices. The protein sequences were back translated into the coding DNA sequences. However, position 41 in the M type DNA sequence is a randomized position and the corresponding codon cannot be used as cutting site for the type IIs restriction enzymes during combination of the modules (Example 1 and FIG. 4). The DNA sequence was then shifted by 6 base pairs to allow the use of the codon of a fixed position as cutting site. The same strategy was applied to the Ny and Ca DNA sequences to keep the correct reading frame and obtain the desired protein sequence. The DNA sequences used for library generation (NyLib, L, CaLib) are shown below.

```
NyLib (N-terminal capping module). DNA (SEQ ID NO: 95) and
protein sequence (SEQ ID NO: 120, which corresponds to
SEQ ID NO: 5 plus amino acids N and E). The overhangs
after digestion with BsaI and BpiI are underlined.
         BamHI
                 E  L  P  Q  M  T  Q  Q  L  N  S  D  D  M  Q  E  Q
   1 CCAGGGATCCGAACTGCCGCAGATGACCCAGCAGCTGAACTCTGACGACATGCAGGAACA
     GGTCCCTAGGCTTGACGGCGTCTACTGGGTCGTCGACTTGAGACTGCTGTACGTCCTTGT

                                                            BsaI
       L  S  A  T  V  K  F  R  Q  I  L  S  R  D  G  N  E
  61 GCTGTCTGCTACCGTTAAATTCCGTCAGATCCTGTCTCGTGATGGTAACGAATGAGACCT
     CGACAGACGATGGCAATTTAAGGCAGTCTAGGACAGAGCACTACCATTGCTTACTCTGGA

       KpnI

 121 TAGGGTACCAGGAA
     ATCCCATGGTCCTT

L (library module). DNA (SEQ ID NO: 96) and protein sequence
(see SEQ ID NO: 4). The randomized positions are indicated by
X in the protein sequence. The corresponding codons are
indicated by NNN.
         BamHI     BpiI
                            E  Q  X  Q  A  V  I  D  A  G  A  L  P
   1 CCAGGGATCCTAGGAAGACCTCGAACAANNNCAAGCTGTTATCGATGCTGGTGCTCTGCC
     GGTCCCTAGGATCCTTCTGGAGCTTGTTTAGGTTCGACAATAGCTACGACCACGAGACGG

       A  L  V  Q  L  L  S  S  P  N  E  K  I  L  K  X  A  L  X  A
  61 GGCTCTGGTTCAACTGCTGTCCTCTCCGAACGAGAAGATCCTGAAANNNGCTCTGNNNGC
     CCGAGACCAAGTTGACGACAGGAGAGGCTTGCTCTTCTAGGACTTTCTTCGAGACACCCG

                                           BsaI      KpnI
       L  X  N  I  A  X  X  G  N
 121 TCTGNNNAACATCGCTNNNNNNGGTAACGAATGAGACCTTAGGGTACCAGGAA
     AGACAGATTGTAGCGAAGACCACCATTGCTTACTCTGGAATCCCATGGTCCTT

CaLib (C-terminal capping module). DNA (SEQ ID NO: 97) and
protein sequence (SEQ ID NO: 121, which corresponds to
SEQ ID NO: 7 minus amino acid N). The stop codons at the
end of the coding sequence are indicated by *
         BamHI           BpiI
                                  E  Q  K  Q  A  V  K  E  A  G  A
   1 CCAGGGATCCTCTAGATAGGAAGACCTCGAACAGAAACAGGCTGTTAAAGAAGCTGGTGC
     GGTCCCTAGGATATCTATCCTTCTGGAGCTTGTCTTTGTCCGACAATTTCTTCGACCACG

       L  E  K  L  E  Q  L  Q  S  H  E  N  E  K  I  Q  K  E  A  Q
  61 TCTGGAGAAACTGGAACAGCTGCAGTCCCACGAGAACGAGAAGATCCAGAAAGAAGCTCA
     AGACCTCTTTGACCTTGTCGACGTCAGGGTGCTCTTGCTCTTCTAGGTCTTTCTTCGAGT

                                              KpnI
       E  A  L  E  K  Q  F  S  H  *  *
 121 GGAAGCTCTGGAGAAGCAGTTCTCCCACTAATGAGGTACCAGGAA
     CCTTCGAGACCTCTTCGTCAAGAGGGTGATTACTCCATGGTCCTT
```

The DNA molecules corresponding to the modules were synthesized starting from overlapping oligonucleotides, indicated in Table 2.

The oligonucleotides lib1F1, lib1F2 and lib1F3 correspond to the first of the six oligonucleotides used for assembly of the internal repeat module library (referred to as L-type module). At position 4, lib1F1 codes for the residues I and T, lib1F2 for E, K and Q, lib1F3 for H and R. These three oligonucleotides were mixed in molar ratio 3:2:2 to obtain the oligonucleotide mixture lib1F, used as a first oligonucleotide during assembly, containing the 7 different codons in equal amount. The oligonucleotide lib5F incorporates trinucleotides phosphoramidites (Virnekas B. et al., Nucleic Acids Res 22:5600-7, 1994) for the codons corresponding to the randomized positions. The trinucleotides phosphoramidites were provided by Glen Research (USA) and lib5F was synthesized by Metabion (Germany). Assembly PCR, ligation (between modules and with capping modules) and cloning were performed according to Example 1. Ny1F, Ny2R, Ny3R and Ny4libRbis were used for synthesis of the N-terminal capping module. Ca1libF, Ca2libR, Ca3F, Ca4R, Ca5F and Ca6R were used for synthesis of the C-terminal capping module. lib1F (3:2:2 lib1F1:lib1F2:lib1F3), lib2R, lib3F, lib4R, lib4R, lib5F and lib6R were used for synthesis of the internal repeat module library. libFor and lib6R were used for amplification of modules after directional ligation.

Expression of Unselected Library Members

Expression of single clones of the library was performed in 5 ml culture and cells were lysed by sonication as described in Example 1. All the unselected library member without deletions or truncations are soluble and with expression yield comparable to the designed armadillo repeat proteins described in the previous Examples.

Example 6

This example presents the selection of specific binding molecules from designed armadillo repeat protein libraries. Binders against SV40 nuclear localization sequence (NLS peptide, peptide sequence KKKRKV, SEQ ID NO:98) were selected using ribosome display (Hanes, J. and Plückthun, A., PNAS 94:4937-42, 1997). The initial library was assembled as described in Example 5, containing, on the protein level from the N-terminal to the C-terminal, 1 Ny module, 1 M module, 3 M modules with randomized positions, 1 M module and 1 Ca module. The M module directly following the N-terminal capping module Ny and the M module directly preceding the C-terminal capping module provide additional stability and reduced aggregation propensity of the library members. The binding of the selected clones toward specific (NLS peptide) and unspecific (NeutrAvidin and cro peptide) targets was assessed by crude extract ELISA indicating that NLS peptide binding armadillo repeat proteins were successfully selected (FIG. 8).

Selection of NLS Peptide Specific Armadillo Repeat Proteins by Ribosome Display

The selection of NLS peptide specific armadillo repeat proteins was performed by ribosome display (Hanes and Plückthun, loc. cit.) using the initial library of designed armadillo repeat proteins as described above and established protocols (Zahnd, C., Amstutz, P. and Plückthun, A, Nat Methods 4:269-79, 2007) with some minor modifications: (i) the translation was made for 15 minutes instead of 10 minutes, (ii) the Herculase II Fusion polymerase (Stratagene) was used in the RT PCR and PCR steps and (iii) the plasmid pRDVhisCAG was used instead of pRDV (GenBank accession number AY327136). The plasmid pRDVhisCAG is identical to pRDV, with the exception that the flag tag (nucleotide sequence CCATGGCGGA CTACAAAGAT GACGATGACA AA, SEQ ID NO:99) of the pRDV is replaced by an MRGS tag (nucleotide sequence TCATGCGAGG GTCGCATCAC CATCACCATC AC, SEQ ID NO:100). The codons for the corresponding N-terminal methionine residues are indicated in bold. Further, biotinylated NLS peptide (JPT, Berlin, Germany) immobilized using plastic bound NeutrAvidin (Pierce) was used as target for the selections, and a prepanning of the library (Zhand et al., loc. cit.) was performed on NeutrAvidin. Selected clones were subcloned in a bacterial expression vector based on pQE30 (Qiagen) for their cytoplasmic expression.

Selected Clones Bind Specifically to the NLS Peptide as Shown by Crude Extract ELISA Selected clones (cloned into the above mentioned expression vector and then transformed into *E. coli* XL1-Blue (Strategene)) were grown overnight at 37° C. in a 96-deep-well plate each in a single well containing 1 ml growth medium (2YT containing 1% glucose and 100 μg/ml ampicillin). One ml of fresh 2YT containing 50 μg/ml ampicillin was inoculated with 100 μl of the overnight culture in a fresh 96-deep-well plate. After incubation for 2 h at 37° C., expression was induced with IPTG (1 mM final concentration) and continued for 3 h. Cells were harvested, resuspended in 100 μl B-PERII (Pierce) and incubated for 15 min at room temperature with shaking. Then, 900 μl PBS-TB (8 mM $Na_2HPO_4$, 1.5 mM $KH_2PO_4$, 137 mM NaCl, 3 mM KCl, 0.2% BSA, 0.1% Tween 20, pH 7.4) were added and cell debris were removed by centrifugation. 100 μl of each lysed clone were applied to a well of a NeutrAvidin coated MaxiSorp plate containing either the NLS peptide or the unrelated cro peptide (PRTSSF, SEQ ID NO:101) immobilized via their biotin moiety or NeutrAvidin alone and incubated for 1 h at RT. After extensive washing with PBS-T (8 mM $Na_2HPO_4$, 1.5 mM $KH_2PO_4$, 137 mM NaCl, 3 mM KCl, 0.1% Tween 20, pH 7.4) the plate was developed using standard ELISA procedures using the monoclonal anti-RGS$(His)_4$ antibody (34650, Qiagen) as primary antibody and a polyclonal goat anti-mouse antibody conjugated with alkaline phosphatase (A3562, Sigma) as secondary reagent. Binding was then detected by using di-sodium 4-nitrophenyl phosphate (4NPP, Fluka) as a substrate for alkaline phosphatase. The color development was measured at 405 nm (FIG. 8).

Example 7

This Example presents a method for the selection of specific single modules and the generation of new specific designed armadillo repeat proteins from pre-selected modules. The method is based on designed armadillo repeat proteins already selected against defined targets and for which the correspondence between the single modules and the parts of the peptide recognized (for example a dipeptide) is known. Repeat modules recognizing specific dipeptides are used as flanking modules of unselected repeat module library L. The collection of designed armadillo repeat protein generated using this combination of modules is then selected for binding to a target peptide which contains the dipeptides recognized by the already selected repeat modules flanking the target dipeptide for which the repeat module library has to be selected. The central selected repeat module can be recovered from clones expressing the selected repeat proteins and stored as single specific repeat module for further use. The selected repeat modules can then be combined in a new repeat protein with predefined specificity.

Designed Armadillo Repeat Proteins for Selection of Single Modules

As an example, a collection of designed armadillo repeat proteins containing Ny and Ca as capping repeat modules and three internal M type modules is required for the binding of a hexapeptide, assuming that each internal repeat module recognizes a dipeptide.

Sequences of modules responsible for specific binding of dipeptides can be derived from previously selected designed armadillo repeat proteins. The specificity can be assessed using methods for the qualitative and quantitative determination of binding constants, in combination with the target peptide and mutated versions of the target peptide. These sequences are used to synthesize the first and the third internal modules (named pre-L and post-L), where an additional unique restriction site will be introduced at the DNA level without affecting the protein sequence. The DNA sequence coding for the complete protein is assembled according to Example 1 using NyL, pre-L, L-type module, post-L and CaL. NyL, L-type module and CaL are described in Example 5. The DNA sequence can then be inserted in a vector appropriate for the selection system of choice. After selection, the clones with higher affinity can be isolated, the plasmid containing the designed armadillo repeat protein purified and the internal selected repeat module from the repeat module library recovered after digestion with restriction enzyme recognizing the restriction site introduced. A PCR amplification using primers providing the missing part of the module will generate the DNA sequence of a selected repeat module in the library format.

The selected module can then be stored or used for the generation of new binders without additional selection steps. A general scheme of the methods is shown in FIG. 9. As an alternative to the recovery of the module DNA, the sequence can be obtained by sequencing and the module rebuilt from oligonucleotides as described in the previous Examples.

Designed Armadillo Repeat Proteins from Pre-Selected Modules

Selected repeat modules in the library format can be assembled as described in Example 1, using NyLib and CaLib (described in Example 5) as capping repeat modules. Due to the specific binding provided by the selected modules, the new protein should be able to recognize as target the peptide sequence that results as combination of the target dipeptides of the single modules (FIG. 10).

The invention claimed is:

1. A collection of armadillo repeat proteins, each armadillo repeat protein comprising at least one repeat domain comprising at least two consecutive repeat modules with an armadillo repeat sequence motif selected from the group consisting of SEQ ID NO: 103, SEQ ID NO: 105, SEQ ID NO: 107 and SEQ ID NO: 109.

2. The collection of claim 1, wherein said repeat domain further comprises an N-terminal capping module at the N-terminal end and/or a C-terminal capping module at the C-terminal end, wherein the N-terminal capping module and the C-terminal capping module each have an amino acid sequence different from any one of said repeat modules.

3. The collection of claim 2, wherein the N-terminal capping module comprises the sequence motif of SEQ ID NO: 5 and/or wherein the C-terminal capping module comprises the sequence motif of SEQ ID NO: 7.

4. The collection of claim 1, wherein said armadillo repeat proteins comprise repeat modules with the armadillo repeat sequence motif of SEQ ID NO: 103.

5. The collection of claim 4, wherein said armadillo repeat proteins comprise repeat modules with the armadillo repeat sequence motif of SEQ ID NO: 104.

6. The collection of claim 1, wherein said armadillo repeat proteins comprise repeat modules with the armadillo repeat sequence motif of SEQ ID NO: 105.

7. The collection of claim 6, wherein said armadillo repeat proteins comprise repeat modules with the armadillo repeat sequence motif of SEQ ID NO: 106.

8. The collection of claim 1, wherein said armadillo repeat proteins comprise repeat modules with the armadillo repeat sequence motif of SEQ ID NO: 107.

9. The collection of claim 8, wherein said armadillo repeat proteins comprise repeat modules with the armadillo repeat sequence motif of SEQ ID NO: 108.

10. The collection of claim 1, wherein said armadillo repeat proteins comprise repeat modules with the armadillo repeat sequence motif of SEQ ID NO: 109.

11. The collection of claim 10, wherein said armadillo repeat proteins comprise repeat modules with the armadillo repeat sequence motif of SEQ ID NO: 110.

12. The collection of claim 1, wherein amino acids at position 26 and 29 of said armadillo repeat sequence motif are each either lys or gin.

13. The collection of claim 3, wherein amino acids at position 26 and 29 of said armadillo repeat sequence motif are each either lys or gin.

14. An armadillo repeat protein from the collection according to claim 1, wherein the armadillo repeat protein is capable of binding a target molecule, and wherein said armadillo repeat protein is a synthetic armadillo repeat protein.

* * * * *

UNITED STATES PATENT AND TRADEMARK OFFICE

CERTIFICATE OF CORRECTION

PATENT NO. : 9,365,629 B2
APPLICATION NO. : 12/733836
DATED : June 14, 2016
INVENTOR(S) : Fabio Parmeggiani et al.

It is certified that error appears in the above-identified patent and that said Letters Patent is hereby corrected as shown below:

On the Title Page:

In item (75), lines 5-6,
"Michael Tobias Stumpp, Geroldswill (CH);" should read --Michael Tobias Stumpp, Geroldswil (CH);--.

In the Claims:

In claim 12, col. 120, line 31,
"gin" should read --gln--.

In claim 13, col. 120, line 34,
"gin" should read --gln--.

Signed and Sealed this
Sixteenth Day of August, 2016

Michelle K. Lee
*Director of the United States Patent and Trademark Office*